(12) United States Patent
Sanford et al.

(10) Patent No.: US 10,543,099 B2
(45) Date of Patent: Jan. 28, 2020

(54) TIBIAL PROSTHESIS

(71) Applicant: Zimmer, Inc., Warsaw, IN (US)

(72) Inventors: Adam H. Sanford, Los Angeles, CA (US); Brian D. Byrd, North Webster, IN (US); Ramesh Annayappa, Bangalore (IN)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 15/703,678

(22) Filed: Sep. 13, 2017

(65) Prior Publication Data

US 2018/0000601 A1 Jan. 4, 2018

Related U.S. Application Data

(63) Continuation of application No. 14/063,593, filed on Oct. 25, 2013, now Pat. No. 9,763,794, which is a continuation of application No. 13/189,328, filed on Jul. 22, 2011, now Pat. No. 8,628,580.

(60) Provisional application No. 61/367,374, filed on Jul. 24, 2010, provisional application No. 61/367,375, filed on Jul. 24, 2010.

(51) Int. Cl.
*A61F 2/38* (2006.01)
*A61F 2/30* (2006.01)

(52) U.S. Cl.
CPC ............ *A61F 2/389* (2013.01); *A61F 2/3836* (2013.01); *A61F 2002/30383* (2013.01); *A61F 2002/30387* (2013.01); *A61F 2002/30395* (2013.01); *A61F 2002/30401* (2013.01); *A61F 2002/30476* (2013.01); *A61F 2002/30576* (2013.01); *A61F 2002/30616* (2013.01); *A61F 2002/30883* (2013.01)

(58) Field of Classification Search
CPC ............ A61F 2/389; A61F 2002/30383; A61F 2002/30387
See application file for complete search history.

(56) References Cited

U.S. PATENT DOCUMENTS

| | | | |
|---|---|---|---|
| 3,774,244 | A | 11/1973 | Walker |
| 4,016,606 | A | 4/1977 | Murray et al. |
| 4,257,129 | A | 3/1981 | Volz |
| 4,340,978 | A | 7/1982 | Buechel et al. |

(Continued)

FOREIGN PATENT DOCUMENTS

| | | |
|---|---|---|
| AU | 2011343440 B2 | 4/2014 |
| AU | 2011286306 B2 | 10/2014 |

(Continued)

OTHER PUBLICATIONS

"Australian Application Serial No. 2011343440, First Examiner Report dated Feb. 17, 2014"; 3 pgs.

(Continued)

*Primary Examiner* — Christopher D. Prone
(74) *Attorney, Agent, or Firm* — Schwegman Lundberg & Woessner, P.A.

(57) ABSTRACT

A tibial prosthesis, and, particularly, a fixed bearing tibial prosthesis is disclosed that has a two-pronged securement mechanism. The securement mechanism may or may not be angled. Advantageously, the securement mechanism, working alone or in cooperation with other securement features, minimizes micromotion between the tibial tray and tibial bearing component.

20 Claims, 39 Drawing Sheets

(56) References Cited

U.S. PATENT DOCUMENTS

| | | |
|---|---|---|
| 4,501,266 A | 2/1985 | McDaniel |
| 4,568,348 A | 2/1986 | Johnson et al. |
| 4,714,474 A | 12/1987 | Brooks, Jr. et al. |
| 4,759,767 A | 7/1988 | Lacey |
| 4,769,040 A | 9/1988 | Wevers |
| 4,770,661 A | 9/1988 | Oh |
| 4,795,468 A | 1/1989 | Hodorek et al. |
| 4,822,365 A | 4/1989 | Walker et al. |
| 4,936,853 A * | 6/1990 | Fabian ............... A61F 2/389 623/20.15 |
| 4,944,757 A | 7/1990 | Martinez et al. |
| 4,950,298 A | 8/1990 | Gustilo et al. |
| 4,959,071 A | 9/1990 | Brown et al. |
| 4,963,152 A | 10/1990 | Hofmann et al. |
| 5,047,057 A | 9/1991 | Lawes |
| 5,047,058 A | 9/1991 | Roberts et al. |
| 5,059,216 A | 10/1991 | Winters |
| 5,061,271 A | 10/1991 | Van Zile |
| 5,071,438 A | 12/1991 | Jones et al. |
| 5,108,442 A | 4/1992 | Smith |
| 5,116,375 A | 5/1992 | Hofmann |
| 5,133,758 A | 7/1992 | Hollister |
| 5,137,536 A | 8/1992 | Koshino |
| 5,147,405 A | 9/1992 | Van Zile |
| 5,171,283 A | 12/1992 | Pappas et al. |
| 5,192,328 A | 3/1993 | Winters |
| 5,197,488 A | 3/1993 | Kovacevic |
| 5,219,362 A | 6/1993 | Tuke et al. |
| 5,236,461 A | 8/1993 | Forte |
| 5,246,459 A | 9/1993 | Elias |
| 5,271,737 A | 12/1993 | Baldwin et al. |
| 5,275,603 A | 1/1994 | Ferrante et al. |
| 5,282,861 A | 2/1994 | Kaplan |
| 5,282,868 A | 2/1994 | Bahler |
| 5,282,870 A | 2/1994 | Moser et al. |
| 5,290,313 A | 3/1994 | Heldreth |
| 5,310,480 A | 5/1994 | Vidueira |
| 5,326,361 A | 7/1994 | Hollister |
| 5,344,460 A | 9/1994 | Turanyi et al. |
| 5,344,461 A | 9/1994 | Phlipot |
| 5,360,016 A | 11/1994 | Kovacevic |
| 5,364,402 A | 11/1994 | Mumme et al. |
| 5,370,699 A * | 12/1994 | Hood ............... A61F 2/3886 623/20.28 |
| 5,387,239 A | 2/1995 | Bianco et al. |
| 5,387,240 A | 2/1995 | Pottenger et al. |
| 5,395,401 A | 3/1995 | Bahler |
| 5,405,396 A | 4/1995 | Heldreth et al. |
| 5,413,604 A | 5/1995 | Hodge |
| 5,413,605 A | 5/1995 | Ashby et al. |
| 5,425,775 A | 6/1995 | Kovacevic et al. |
| 5,458,637 A | 10/1995 | Hayes |
| 5,470,354 A | 11/1995 | Hershberger et al. |
| 5,489,311 A | 2/1996 | Cipolletti |
| 5,507,820 A | 4/1996 | Pappas |
| 5,549,688 A | 8/1996 | Ries et al. |
| 5,556,433 A | 9/1996 | Gabriel et al. |
| 5,571,194 A | 11/1996 | Gabriel |
| 5,609,639 A | 3/1997 | Walker |
| 5,609,641 A | 3/1997 | Johnson et al. |
| 5,609,643 A | 3/1997 | Colleran et al. |
| 5,609,645 A | 3/1997 | Vinciuerra |
| 5,613,970 A | 3/1997 | Houston et al. |
| 5,656,785 A | 8/1997 | Trainor et al. |
| 5,658,341 A | 8/1997 | Delfosse |
| 5,658,342 A | 8/1997 | Draganich et al. |
| 5,658,344 A | 8/1997 | Hurlburt |
| 5,683,470 A | 11/1997 | Johnson et al. |
| 5,702,463 A | 12/1997 | Pothier et al. |
| 5,702,464 A | 12/1997 | Lackey et al. |
| 5,733,292 A | 3/1998 | Gustilo et al. |
| 5,755,801 A | 5/1998 | Walker et al. |
| 5,755,802 A | 5/1998 | Gerber |
| 5,776,200 A | 7/1998 | Johnson et al. |
| 5,782,925 A | 7/1998 | Collazo et al. |
| 5,824,100 A | 10/1998 | Kester et al. |
| 5,824,102 A | 10/1998 | Buscayret |
| 5,824,103 A | 10/1998 | Williams et al. |
| 5,871,539 A | 2/1999 | Pappas |
| 5,871,541 A | 2/1999 | Gerber |
| 5,871,543 A | 2/1999 | Hofmann |
| 5,871,545 A | 2/1999 | Goodfellow et al. |
| 5,879,394 A | 3/1999 | Ashby et al. |
| 5,906,643 A | 5/1999 | Walker |
| 5,911,723 A | 6/1999 | Ashby et al. |
| 5,928,286 A | 7/1999 | Ashby et al. |
| 5,964,808 A | 10/1999 | Blaha et al. |
| 5,968,099 A | 10/1999 | Badorf et al. |
| 5,976,147 A | 11/1999 | LaSalle et al. |
| 6,004,351 A | 12/1999 | Tomita et al. |
| 6,004,352 A | 12/1999 | Buni |
| 6,010,534 A | 1/2000 | O'neil et al. |
| 6,013,103 A | 1/2000 | Kaufman et al. |
| 6,039,764 A | 3/2000 | Pottenger et al. |
| 6,068,658 A | 5/2000 | Insall et al. |
| 6,074,425 A | 6/2000 | Pappas |
| 6,080,195 A | 6/2000 | Colleran et al. |
| 6,090,144 A | 7/2000 | Letot et al. |
| 6,102,954 A | 8/2000 | Albrektsson et al. |
| 6,102,955 A | 8/2000 | Mendes et al. |
| 6,123,729 A | 9/2000 | Insall et al. |
| 6,126,692 A | 10/2000 | Robie et al. |
| 6,143,034 A | 11/2000 | Burrows |
| 6,197,064 B1 | 3/2001 | Haines et al. |
| 6,203,576 B1 | 3/2001 | Afriat et al. |
| 6,206,927 B1 | 3/2001 | Fell et al. |
| 6,210,443 B1 | 4/2001 | Marceaux et al. |
| RE37,277 E | 7/2001 | Baldwin et al. |
| 6,258,127 B1 | 7/2001 | Schmotzer |
| 6,306,172 B1 | 10/2001 | O'Neil et al. |
| 6,325,828 B1 | 12/2001 | Dennis et al. |
| 6,379,388 B1 | 4/2002 | Ensign et al. |
| 6,406,497 B2 | 6/2002 | Takei et al. |
| 6,413,279 B1 | 7/2002 | Metzger et al. |
| 6,428,577 B1 | 8/2002 | Evans |
| 6,436,145 B1 | 8/2002 | Miller |
| 6,491,726 B2 | 12/2002 | Pappas |
| 6,506,215 B1 | 1/2003 | Letot et al. |
| 6,506,216 B1 | 1/2003 | McCue et al. |
| 6,558,426 B1 | 5/2003 | Masini |
| 6,607,559 B2 | 8/2003 | Ralph et al. |
| 6,623,526 B1 | 9/2003 | Lloyd |
| 6,632,225 B2 | 10/2003 | Sanford et al. |
| 6,660,039 B1 | 12/2003 | Evans et al. |
| 6,702,821 B2 | 3/2004 | Bonutti |
| 6,709,461 B2 | 3/2004 | O'neil et al. |
| 6,743,258 B1 | 6/2004 | Keller |
| 6,755,864 B1 | 6/2004 | Brack et al. |
| 6,770,078 B2 | 8/2004 | Bonutti |
| 6,869,448 B2 | 3/2005 | Tuke |
| 6,923,832 B1 | 8/2005 | Sharkey et al. |
| 6,942,670 B2 | 9/2005 | Heldreth et al. |
| 6,953,479 B2 | 10/2005 | Carson et al. |
| 6,974,481 B1 | 12/2005 | Carson |
| 6,986,791 B1 | 1/2006 | Metzger |
| 7,025,788 B2 | 4/2006 | Metzger et al. |
| 7,060,074 B2 | 6/2006 | Rosa et al. |
| 7,081,137 B1 | 7/2006 | Servidio |
| 7,083,652 B2 | 8/2006 | McCue et al. |
| 7,153,326 B1 | 12/2006 | Metzger |
| 7,160,330 B2 | 1/2007 | Axelson, Jr. et al. |
| 7,189,262 B2 | 3/2007 | Hayes, Jr. et al. |
| 7,261,740 B2 | 8/2007 | Tuttle et al. |
| 7,264,635 B2 | 9/2007 | Suguro |
| 7,294,149 B2 | 11/2007 | Hozack et al. |
| 7,309,362 B2 | 12/2007 | Yasuda et al. |
| 7,309,363 B2 | 12/2007 | Dietz |
| 7,326,252 B2 | 2/2008 | Otto et al. |
| 7,351,263 B2 | 4/2008 | Afriat |
| 7,364,581 B2 | 4/2008 | Michalowicz |
| 7,412,897 B2 | 8/2008 | Crottet et al. |
| 7,413,577 B1 | 8/2008 | Servidio |
| 7,442,196 B2 | 10/2008 | Fisher et al. |
| 7,445,639 B2 | 11/2008 | Metzger et al. |

(56) References Cited

U.S. PATENT DOCUMENTS

| | | |
|---|---|---|
| 7,488,330 B2 | 2/2009 | Stad |
| 7,497,874 B1 | 3/2009 | Metzger et al. |
| 7,513,912 B2 | 4/2009 | Hayes, Jr. et al. |
| 7,544,211 B2 | 6/2009 | Rochetin |
| 7,547,327 B2 | 6/2009 | Collazo |
| 7,575,602 B2 | 8/2009 | Amirouche et al. |
| 7,578,821 B2 | 8/2009 | Fisher et al. |
| 7,585,328 B2 | 9/2009 | Haas |
| 7,587,945 B2 | 9/2009 | Crottet et al. |
| 7,591,854 B2 | 9/2009 | Wasielewski |
| 7,625,407 B2 | 12/2009 | Akizuki |
| 7,628,818 B2 | 12/2009 | Hazebrouck et al. |
| 7,632,283 B2 | 12/2009 | Heldreth |
| 7,632,314 B2 | 12/2009 | Dietz |
| 7,635,390 B1 | 12/2009 | Bonutti |
| 7,678,152 B2 | 3/2010 | Suguro et al. |
| 7,695,519 B2 | 4/2010 | Collazo |
| 7,695,520 B2 | 4/2010 | Metzger et al. |
| 7,776,085 B2 | 8/2010 | Bernero et al. |
| 7,837,691 B2 | 11/2010 | Cordes et al. |
| 7,850,698 B2 | 12/2010 | Straszheim-Morley et al. |
| 8,012,216 B2 | 9/2011 | Metzger |
| 8,065,927 B2 | 11/2011 | Crottet et al. |
| 8,141,437 B2 | 3/2012 | Amirouche et al. |
| 8,197,549 B2 | 6/2012 | Amirouche et al. |
| 8,211,041 B2 | 7/2012 | Fisher et al. |
| 8,245,583 B2 | 8/2012 | Stein |
| 8,491,589 B2 | 7/2013 | Fisher et al. |
| 8,506,571 B2 | 8/2013 | Chana et al. |
| 8,568,486 B2 | 10/2013 | Wentorf et al. |
| 8,574,304 B2 | 11/2013 | Wentorf et al. |
| 8,591,594 B2 | 11/2013 | Parisi et al. |
| 8,603,101 B2 | 12/2013 | Claypool et al. |
| 8,613,775 B2 | 12/2013 | Wentorf et al. |
| 8,628,580 B2 | 1/2014 | Sanford et al. |
| 8,690,954 B2 | 4/2014 | Parisi et al. |
| 8,758,444 B2 | 6/2014 | Wentorf et al. |
| 8,764,838 B2 | 7/2014 | Parisi et al. |
| 8,764,840 B2 | 7/2014 | Sanford et al. |
| 8,858,643 B2 | 10/2014 | Parisi et al. |
| 8,932,298 B2 | 1/2015 | Colquhoun et al. |
| 8,932,365 B2 | 1/2015 | Parisi et al. |
| 8,979,847 B2 | 3/2015 | Belcher et al. |
| 9,011,459 B2 | 4/2015 | Claypool et al. |
| 9,072,607 B2 | 7/2015 | Parisi et al. |
| 9,149,206 B2 | 10/2015 | Claypool et al. |
| 9,186,255 B2 | 11/2015 | Parisi |
| 9,192,480 B2 | 11/2015 | Wentorf et al. |
| 9,204,970 B2 | 12/2015 | Parisi et al. |
| 9,283,082 B2 | 3/2016 | Sanford et al. |
| 9,295,557 B2 | 3/2016 | Wentorf et al. |
| 9,295,558 B2 | 3/2016 | Parisi et al. |
| 9,308,096 B2 | 4/2016 | Wentorf et al. |
| 9,314,343 B2 | 4/2016 | Parisi et al. |
| 9,381,090 B2 | 7/2016 | Wentorf et al. |
| 9,427,337 B2 | 8/2016 | Claypool et al. |
| 9,492,290 B2 | 11/2016 | Claypool et al. |
| 9,539,116 B2 | 1/2017 | Claypool |
| 9,592,133 B2 | 3/2017 | Toler et al. |
| 9,597,090 B2 | 3/2017 | Claypool et al. |
| 9,655,728 B2 | 5/2017 | Parisi et al. |
| 9,655,729 B2 | 5/2017 | Parisi et al. |
| 9,763,794 B2 | 9/2017 | Sanford et al. |
| 9,763,807 B2 | 9/2017 | Claypool et al. |
| 9,788,954 B2 | 10/2017 | Parisi et al. |
| 9,861,490 B2 | 1/2018 | Wentorf et al. |
| 9,901,331 B2 | 2/2018 | Toler et al. |
| 9,918,844 B2 | 3/2018 | Sanford et al. |
| 9,925,050 B2 | 3/2018 | Parisi et al. |
| 10,010,330 B2 | 7/2018 | Claypool et al. |
| 10,188,530 B2 | 1/2019 | Claypool et al. |
| 10,195,041 B2 | 2/2019 | Wentorf et al. |
| 10,265,181 B2 | 4/2019 | Wentorf et al. |
| 10,278,827 B2 | 5/2019 | Drury et al. |
| 2001/0047210 A1 | 11/2001 | Wolf |
| 2002/0058997 A1 | 5/2002 | O'connor et al. |
| 2002/0072802 A1 | 6/2002 | O'Neil et al. |
| 2002/0120340 A1 | 8/2002 | Metzger et al. |
| 2002/0161448 A1 | 10/2002 | Hayes, Jr. et al. |
| 2003/0055509 A1 | 3/2003 | Mccue et al. |
| 2004/0019382 A1 | 1/2004 | Amirouche et al. |
| 2004/0034432 A1 | 2/2004 | Hughes et al. |
| 2004/0059340 A1 | 3/2004 | Serra et al. |
| 2004/0064191 A1 | 4/2004 | Wasielewski |
| 2004/0122441 A1 | 6/2004 | Muratsu |
| 2004/0153066 A1 | 8/2004 | Coon et al. |
| 2004/0162620 A1 | 8/2004 | Wyss |
| 2004/0167537 A1 | 8/2004 | Errico et al. |
| 2004/0186582 A1 | 9/2004 | Yasuda et al. |
| 2004/0204765 A1 | 10/2004 | Fenning et al. |
| 2004/0225368 A1 | 11/2004 | Plumet et al. |
| 2004/0236429 A1 | 11/2004 | Ensign et al. |
| 2004/0243244 A1 | 12/2004 | Otto et al. |
| 2004/0267371 A1 | 12/2004 | Hayes, Jr. et al. |
| 2005/0055102 A1 | 3/2005 | Tornier et al. |
| 2005/0096747 A1 | 5/2005 | Tuttle et al. |
| 2005/0143831 A1 | 6/2005 | Justin et al. |
| 2005/0143832 A1 | 6/2005 | Carson |
| 2005/0177170 A1 | 8/2005 | Fisher et al. |
| 2005/0197710 A1 | 9/2005 | Naegerl |
| 2005/0209701 A1 | 9/2005 | Suguro et al. |
| 2005/0209702 A1 | 9/2005 | Todd et al. |
| 2005/0246030 A1 | 11/2005 | Yao |
| 2005/0267485 A1 | 12/2005 | Cordes et al. |
| 2005/0267584 A1 | 12/2005 | Burdulis et al. |
| 2005/0278035 A1 | 12/2005 | Wyss et al. |
| 2006/0004460 A1 | 1/2006 | Engh et al. |
| 2006/0020343 A1 | 1/2006 | Ek |
| 2006/0030945 A1 | 2/2006 | Wright |
| 2006/0052782 A1 | 3/2006 | Morgan et al. |
| 2006/0069436 A1 | 3/2006 | Sutton et al. |
| 2006/0089653 A1 | 4/2006 | Auger et al. |
| 2006/0142869 A1 | 6/2006 | Gross |
| 2006/0161259 A1 | 7/2006 | Cheng et al. |
| 2006/0184176 A1 | 8/2006 | Straszheim-Morley et al. |
| 2006/0189864 A1 | 8/2006 | Paradis et al. |
| 2006/0190087 A1 | 8/2006 | O'Connor et al. |
| 2006/0195195 A1 | 8/2006 | Burstein et al. |
| 2006/0111726 A1 | 10/2006 | Felt et al. |
| 2006/0224244 A1 | 10/2006 | Thomas et al. |
| 2006/0265080 A1 | 11/2006 | Mcminn |
| 2007/0010890 A1 | 1/2007 | Collazo |
| 2007/0123992 A1 | 5/2007 | Sanford |
| 2007/0129808 A1 | 6/2007 | Justin et al. |
| 2007/0135926 A1 | 6/2007 | Walker |
| 2007/0185581 A1 | 8/2007 | Akizuki et al. |
| 2007/0198022 A1 | 8/2007 | Lang et al. |
| 2007/0233269 A1 | 10/2007 | Steines et al. |
| 2007/0234819 A1 | 10/2007 | Amirouche et al. |
| 2007/0239165 A1 | 10/2007 | Amirouche |
| 2008/0021566 A1 | 1/2008 | Peters et al. |
| 2008/0051908 A1 | 2/2008 | Angibaud et al. |
| 2008/0091271 A1 | 4/2008 | Bonitati et al. |
| 2008/0091272 A1 | 4/2008 | Aram et al. |
| 2008/0091273 A1 | 4/2008 | Hazebrouck |
| 2008/0103603 A1 | 5/2008 | Hintermann |
| 2008/0114462 A1 | 5/2008 | Guidera et al. |
| 2008/0119938 A1 | 5/2008 | Oh |
| 2008/0119940 A1 | 5/2008 | Otto et al. |
| 2008/0161918 A1 | 7/2008 | Fankhauser et al. |
| 2008/0167722 A1 | 7/2008 | Metzger et al. |
| 2008/0215156 A1 | 9/2008 | Duggal et al. |
| 2008/0243258 A1 | 10/2008 | Sancheti |
| 2008/0281426 A1 | 11/2008 | Fitz et al. |
| 2008/0288080 A1 | 11/2008 | Sancheti |
| 2008/0300689 A1 | 12/2008 | McKinnon et al. |
| 2008/0300690 A1 | 12/2008 | Burstein et al. |
| 2009/0005708 A1 | 1/2009 | Johanson et al. |
| 2009/0036992 A1 | 2/2009 | Tsakonas |
| 2009/0043395 A1 | 2/2009 | Hotokebuchi et al. |
| 2009/0082873 A1 | 3/2009 | Hazebrouck et al. |
| 2009/0088862 A1 | 4/2009 | Thomas et al. |
| 2009/0125114 A1 | 5/2009 | May et al. |
| 2009/0149963 A1 | 6/2009 | Sekel |

(56) References Cited

U.S. PATENT DOCUMENTS

| | | |
|---|---|---|
| 2009/0149964 A1 | 6/2009 | May et al. |
| 2009/0204221 A1 | 8/2009 | Walker |
| 2009/0204222 A1 | 8/2009 | Burstein et al. |
| 2009/0210066 A1 | 8/2009 | Jasty |
| 2009/0222103 A1 | 9/2009 | Fitz et al. |
| 2009/0259314 A1 | 10/2009 | Linder-ganz et al. |
| 2009/0264894 A1 | 10/2009 | Wasielewski |
| 2009/0265013 A1 | 10/2009 | Mandell |
| 2009/0287310 A1 | 11/2009 | Fisher et al. |
| 2009/0306786 A1 | 12/2009 | Samuelson |
| 2009/0306787 A1 | 12/2009 | Crabtree et al. |
| 2009/0319047 A1 | 12/2009 | Walker |
| 2009/0319048 A1 | 12/2009 | Shah et al. |
| 2009/0319049 A1 | 12/2009 | Shah et al. |
| 2009/0326663 A1 | 12/2009 | Dun |
| 2009/0326665 A1 | 12/2009 | Wyss et al. |
| 2009/0326666 A1 | 12/2009 | Wyss et al. |
| 2009/0326668 A1 | 12/2009 | Dun |
| 2010/0010494 A1 | 1/2010 | Quirno |
| 2010/0016976 A1 | 1/2010 | Siebel |
| 2010/0016977 A1 | 1/2010 | Masini |
| 2010/0016978 A1 | 1/2010 | Williams et al. |
| 2010/0016979 A1 | 1/2010 | Wyss et al. |
| 2010/0036499 A1 | 2/2010 | Pinskerova |
| 2010/0036500 A1 | 2/2010 | Heldreth et al. |
| 2010/0063594 A1 | 3/2010 | Hazebrouck et al. |
| 2010/0063595 A1 | 3/2010 | Dietz |
| 2010/0076563 A1 | 3/2010 | Otto et al. |
| 2010/0082111 A1 | 4/2010 | Thomas |
| 2010/0100011 A1 | 4/2010 | Roche |
| 2010/0100189 A1 | 4/2010 | Metzger |
| 2010/0100191 A1 | 4/2010 | May et al. |
| 2010/0125339 A1 | 5/2010 | Earl et al. |
| 2010/0152858 A1 | 6/2010 | Lu et al. |
| 2010/0191341 A1 | 7/2010 | Byrd |
| 2010/0198275 A1 | 8/2010 | Chana et al. |
| 2010/0222890 A1 | 9/2010 | Barnett et al. |
| 2010/0249660 A1 | 9/2010 | Sherman et al. |
| 2010/0249789 A1 | 9/2010 | Rock et al. |
| 2010/0262253 A1 | 10/2010 | Cipolletti et al. |
| 2010/0286788 A1 | 11/2010 | Komistek |
| 2010/0305708 A1 | 12/2010 | Lang |
| 2010/0329530 A1 | 12/2010 | Lang et al. |
| 2011/0022179 A1 | 1/2011 | Andriacchi et al. |
| 2011/0029091 A1 | 2/2011 | Bojarski et al. |
| 2011/0040387 A1 | 2/2011 | Ries et al. |
| 2011/0082558 A1 | 4/2011 | Kim et al. |
| 2011/0082559 A1 | 4/2011 | Hartdegen et al. |
| 2011/0087332 A1 | 4/2011 | Bojarski et al. |
| 2011/0100011 A1 | 5/2011 | Staffend |
| 2011/0125278 A1 | 5/2011 | Bercovy et al. |
| 2011/0144760 A1 | 6/2011 | Wong et al. |
| 2011/0251695 A1 | 10/2011 | Lenz et al. |
| 2012/0022658 A1 | 1/2012 | Wentorf |
| 2012/0022659 A1 | 1/2012 | Wentorf |
| 2012/0022660 A1 | 1/2012 | Wentorf |
| 2012/0035735 A1 | 2/2012 | Sanford et al. |
| 2012/0035737 A1 | 2/2012 | Sanford |
| 2012/0095563 A1 | 4/2012 | Sanford et al. |
| 2012/0101585 A1 | 4/2012 | Parisi et al. |
| 2012/0158152 A1 | 6/2012 | Claypool et al. |
| 2012/0179069 A1 | 7/2012 | Amirouche |
| 2012/0185054 A1 | 7/2012 | Maloney et al. |
| 2012/0232429 A1 | 9/2012 | Fischer et al. |
| 2012/0290088 A1 | 11/2012 | Amirouche et al. |
| 2012/0310246 A1 | 12/2012 | Belcher et al. |
| 2012/0323336 A1 | 12/2012 | Parisi et al. |
| 2013/0013076 A1 | 1/2013 | Fisher et al. |
| 2013/0024001 A1 | 1/2013 | Wentorf et al. |
| 2013/0079671 A1 | 3/2013 | Stein et al. |
| 2013/0096567 A1 | 4/2013 | Fisher et al. |
| 2013/0102929 A1 | 4/2013 | Haight et al. |
| 2013/0103038 A1 | 4/2013 | Fischer et al. |
| 2013/0131816 A1 | 5/2013 | Parisi et al. |
| 2013/0131817 A1 | 5/2013 | Parisi et al. |
| 2013/0131818 A1 | 5/2013 | Parisi et al. |
| 2013/0131819 A1 | 5/2013 | Parisi et al. |
| 2013/0131820 A1 | 5/2013 | Wentorf et al. |
| 2013/0173010 A1 | 7/2013 | Irwin |
| 2013/0283378 A1 | 9/2013 | Claypool et al. |
| 2013/0261504 A1 | 10/2013 | Claypool et al. |
| 2013/0261757 A1 | 10/2013 | Claypool et al. |
| 2013/0261758 A1 | 10/2013 | Claypool et al. |
| 2014/0025175 A1 | 1/2014 | Wentorf et al. |
| 2014/0025176 A1 | 1/2014 | Wentorf |
| 2014/0025177 A1 | 1/2014 | Wentorf et al. |
| 2014/0052268 A1 | 2/2014 | Sanford et al. |
| 2014/0052269 A1 | 2/2014 | Claypool et al. |
| 2014/0156015 A1 | 6/2014 | Parisi et al. |
| 2014/0163687 A1 | 6/2014 | Parisi et al. |
| 2014/0249641 A1 | 9/2014 | Wentorf et al. |
| 2014/0257505 A1 | 9/2014 | Parisi et al. |
| 2014/0257506 A1 | 9/2014 | Sanford et al. |
| 2014/0296859 A1 | 10/2014 | Claypool et al. |
| 2015/0005890 A1 | 1/2015 | Parisi et al. |
| 2015/0088140 A1 | 3/2015 | Toler et al. |
| 2015/0190243 A1 | 7/2015 | Claypool et al. |
| 2015/0282936 A1 | 10/2015 | Parisi et al. |
| 2015/0320564 A1 | 11/2015 | Parisi et al. |
| 2015/0359642 A1 | 12/2015 | Claypool et al. |
| 2016/0038294 A1 | 2/2016 | Parisi et al. |
| 2016/0045322 A1 | 2/2016 | Parisi et al. |
| 2016/0135959 A1 | 5/2016 | Sanford et al. |
| 2016/0158019 A1 | 6/2016 | Grey et al. |
| 2016/0184107 A1 | 6/2016 | Parisi et al. |
| 2016/0287397 A1 | 10/2016 | Wentorf |
| 2016/0324647 A1 | 11/2016 | Claypool et al. |
| 2017/0079801 A1 | 3/2017 | Drury et al. |
| 2017/0143324 A1 | 5/2017 | Toler et al. |
| 2017/0156736 A1 | 6/2017 | Claypool et al. |
| 2018/0000602 A1 | 1/2018 | Wentorf et al. |
| 2018/0000612 A1 | 1/2018 | Claypool et al. |
| 2018/0021143 A1 | 1/2018 | Parisi et al. |
| 2018/0021144 A1 | 1/2018 | Parisi et al. |
| 2018/0085225 A1 | 3/2018 | Wentorf et al. |
| 2018/0256346 A1 | 9/2018 | Byrd et al. |

FOREIGN PATENT DOCUMENTS

| | | |
|---|---|---|
| CA | 2190029 A1 | 11/1995 |
| CH | 687584 A5 | 1/1997 |
| CN | 1087506 A | 6/1994 |
| CN | 1174498 A | 2/1998 |
| CN | 1179709 A | 4/1998 |
| CN | 1440262 A | 9/2003 |
| CN | 1549695 A | 11/2004 |
| CN | 2768715 Y | 4/2006 |
| CN | 1780594 A | 5/2006 |
| CN | 1874738 A | 12/2006 |
| CN | 101214175 A | 7/2008 |
| CN | 101288597 A | 10/2008 |
| CN | 101347359 A | 1/2009 |
| CN | 201175391 Y | 1/2009 |
| CN | 101361684 A | 2/2009 |
| CN | 101401750 A | 4/2009 |
| CN | 101426453 A | 5/2009 |
| CN | 101522136 A | 9/2009 |
| CN | 101646392 A | 2/2010 |
| CN | 101658446 A | 3/2010 |
| CN | 101683289 A | 3/2010 |
| CN | 101711701 A | 5/2010 |
| CN | 101795643 A | 8/2010 |
| CN | 101835441 A | 9/2010 |
| CN | 102018584 A | 4/2011 |
| CN | 102048594 A | 5/2011 |
| CN | 102058448 A | 5/2011 |
| CN | 102917670 A | 2/2013 |
| CN | 103118634 A | 5/2013 |
| CN | 103118635 A | 5/2013 |
| CN | 103118636 A | 5/2013 |
| CN | 103370025 A | 10/2013 |
| CN | 103379880 A | 10/2013 |
| CN | 104066402 A | 9/2014 |
| CN | 104093380 A | 10/2014 |

(56) References Cited

FOREIGN PATENT DOCUMENTS

| | | |
|---|---|---|
| CN | 104135969 A | 11/2014 |
| CN | 104203160 A | 12/2014 |
| CN | 104379094 A | 2/2015 |
| CN | 104736105 A | 6/2015 |
| CN | 105055052 A | 11/2015 |
| CN | 105167889 A | 12/2015 |
| CN | 2856070 C | 7/2016 |
| CN | 103118634 B | 8/2016 |
| CN | 103118636 B | 8/2016 |
| CN | 104093380 B | 8/2016 |
| CN | 103370025 B | 11/2016 |
| CN | 106073949 A | 11/2016 |
| CN | 106214292 A | 12/2016 |
| CN | 108135701 A | 6/2018 |
| CN | 106073949 B | 12/2018 |
| EP | 0021421 A1 | 1/1981 |
| EP | 0327495 A2 | 8/1989 |
| EP | 0340919 A1 | 11/1989 |
| EP | 340919 A1 | 11/1989 |
| EP | 0372811 A1 | 6/1990 |
| EP | 0306744 B1 | 4/1992 |
| EP | 0495340 A1 | 7/1992 |
| EP | 0636353 A1 | 2/1995 |
| EP | 0672397 A1 | 9/1995 |
| EP | 0552950 B1 | 9/1996 |
| EP | 0536457 B1 | 1/1997 |
| EP | 0642328 B1 | 12/1998 |
| EP | 0592750 B1 | 1/1999 |
| EP | 0903125 A1 | 3/1999 |
| EP | 0956836 A1 | 11/1999 |
| EP | 0956836 B1 | 11/1999 |
| EP | 1025818 A2 | 8/2000 |
| EP | 1097679 A1 | 5/2001 |
| EP | 0709074 B1 | 12/2002 |
| EP | 1327424 A1 | 7/2003 |
| EP | 1378216 A2 | 1/2004 |
| EP | 1477143 A1 | 11/2004 |
| EP | 1568336 A1 | 8/2005 |
| EP | 1719478 A2 | 11/2006 |
| EP | 1722721 A1 | 11/2006 |
| EP | 1354571 B1 | 6/2007 |
| EP | 1396240 B1 | 4/2008 |
| EP | 1604623 B1 | 6/2008 |
| EP | 1996122 A1 | 12/2008 |
| EP | 0927009 B1 | 1/2009 |
| EP | 2011455 A1 | 1/2009 |
| EP | 1696835 B1 | 2/2009 |
| EP | 1132063 A2 | 9/2009 |
| EP | 1591082 B1 | 9/2009 |
| EP | 2140838 A2 | 1/2010 |
| EP | 2143403 A1 | 1/2010 |
| EP | 2237177 A1 | 10/2010 |
| EP | 1555962 B1 | 2/2011 |
| EP | 2319460 A1 | 5/2011 |
| EP | 2324799 A2 | 5/2011 |
| EP | 2335654 A1 | 6/2011 |
| EP | 2347733 A1 | 7/2011 |
| EP | 0689808 B1 | 9/2012 |
| EP | 2595573 A1 | 5/2013 |
| EP | 2782525 A1 | 10/2014 |
| EP | 2830543 A1 | 2/2015 |
| EP | 2830544 A1 | 2/2015 |
| EP | 2830544 B1 | 9/2016 |
| EP | 2918235 B1 | 1/2017 |
| EP | 3111894 B1 | 12/2018 |
| FR | 2736819 A1 | 1/1997 |
| FR | 2747914 A1 | 10/1997 |
| FR | 2778332 A1 | 11/1999 |
| FR | 2788964 A1 | 8/2000 |
| FR | 2824260 A1 | 11/2002 |
| FR | 2852819 A1 | 10/2004 |
| FR | 2926719 A1 | 7/2009 |
| GB | 225347 A | 12/1924 |
| GB | 2253147 A | 9/1992 |
| GB | 2345446 A | 7/2000 |
| IN | 7145DELNP2014 A | 4/2015 |
| JP | 61247449 | 11/1986 |
| JP | 62270153 A | 11/1987 |
| JP | 06203576 A | 7/1994 |
| JP | 0928998 A | 11/1997 |
| JP | 09511668 A | 11/1997 |
| JP | 2000000255 A | 1/2000 |
| JP | 2000245758 A | 9/2000 |
| JP | 2003516183 A | 5/2003 |
| JP | 2004166802 A | 6/2004 |
| JP | 2004254811 A | 9/2004 |
| JP | 3734270 B2 | 1/2006 |
| JP | 2007054488 A | 3/2007 |
| JP | 2007509709 A | 4/2007 |
| JP | 2007222616 A | 9/2007 |
| JP | 2009082713 A | 4/2009 |
| JP | 20092456192 | 10/2009 |
| JP | 2010188051 A | 9/2010 |
| JP | 2010240406 A | 10/2010 |
| JP | 2011092738 A | 5/2011 |
| JP | 2012500667 A | 1/2012 |
| JP | 2012531265 A | 12/2012 |
| JP | 2015512307 A | 4/2013 |
| JP | 2013535276 A | 9/2013 |
| JP | 2013536005 A | 9/2013 |
| JP | 2013536006 A | 9/2013 |
| JP | 2013536007 A | 9/2013 |
| JP | 2014505517 A | 3/2014 |
| JP | 2014508554 A | 4/2014 |
| JP | 2014239900 A | 12/2014 |
| JP | 2015502203 A | 1/2015 |
| JP | 2015504333 A | 2/2015 |
| JP | 2015504759 A | 2/2015 |
| JP | 2015513966 A | 5/2015 |
| JP | 2015231566 A | 12/2015 |
| JP | 2016028729 A | 3/2016 |
| JP | 5980341 B2 | 8/2016 |
| JP | 2016195841 A | 11/2016 |
| JP | 2017221732 A | 12/2017 |
| WO | WO-9305729 A2 | 4/1993 |
| WO | WO-9409725 A1 | 5/1994 |
| WO | WO-9514444 A1 | 6/1995 |
| WO | WO-9514446 A1 | 6/1995 |
| WO | WO-9530389 A1 | 11/1995 |
| WO | WO-9535074 A1 | 12/1995 |
| WO | WO-9934755 A1 | 7/1999 |
| WO | WO-0141680 A1 | 6/2001 |
| WO | WO-200141680 A1 | 6/2001 |
| WO | WO-03099106 A2 | 12/2003 |
| WO | WO-2004058108 A1 | 7/2004 |
| WO | WO-2005037147 A1 | 4/2005 |
| WO | WO-2005051240 A1 | 6/2005 |
| WO | WO-2005122967 A1 | 12/2005 |
| WO | WO-2006058057 A2 | 6/2006 |
| WO | WO-2006092167 A1 | 9/2006 |
| WO | WO-2007108804 A1 | 9/2007 |
| WO | WO-2007109641 A2 | 9/2007 |
| WO | WO-2007119173 A2 | 10/2007 |
| WO | WO-2009029631 A1 | 3/2009 |
| WO | WO-2009088236 A2 | 7/2009 |
| WO | WO-2009088238 A2 | 7/2009 |
| WO | WO-2009105495 A1 | 8/2009 |
| WO | WO-2010001010 A1 | 1/2010 |
| WO | WO-2010008803 A2 | 1/2010 |
| WO | WO-2010011590 A1 | 1/2010 |
| WO | WO-2010022272 A1 | 2/2010 |
| WO | WO-2010023062 A2 | 3/2010 |
| WO | WO-2010045537 A1 | 4/2010 |
| WO | WO-2011043955 A1 | 4/2011 |
| WO | WO-2011063123 A2 | 5/2011 |
| WO | WO-2011071979 A2 | 6/2011 |
| WO | WO-2011072235 A2 | 6/2011 |
| WO | WO-2011110865 A2 | 9/2011 |
| WO | WO-2012004580 A1 | 1/2012 |
| WO | WO-20120460 A1 | 2/2012 |
| WO | WO-2012018563 A1 | 2/2012 |
| WO | WO-2012018564 A1 | 2/2012 |
| WO | WO-2012018565 A1 | 2/2012 |
| WO | WO-2012018566 A1 | 2/2012 |

(56) References Cited

FOREIGN PATENT DOCUMENTS

| WO | WO-2012018567 A1 | 2/2012 |
|---|---|---|
| WO | WO-2012082628 A1 | 6/2012 |
| WO | Wo-2012083280 A1 | 6/2012 |
| WO | WO-2012112698 A2 | 8/2012 |
| WO | WO-2013013094 A1 | 1/2013 |
| WO | WO-2013074142 A1 | 5/2013 |
| WO | WO-2013074143 A1 | 5/2013 |
| WO | WO-2013074144 A1 | 5/2013 |
| WO | WO-2013074145 A1 | 5/2013 |
| WO | WO-2013077919 A1 | 5/2013 |
| WO | WO-2013115849 A1 | 8/2013 |
| WO | WO-201314895 A1 | 10/2013 |
| WO | WO-2013148960 A1 | 10/2013 |
| WO | WO-2017053196 A1 | 3/2017 |
| WO | WO-2018165442 A1 | 9/2018 |

OTHER PUBLICATIONS

"Australian Application Serial No. 2011343440, Response filed Mar. 21, 2014 to Office Action dated Feb. 17, 2014", 1 pg.
"Australian Application Serial No. 2013238046, First Examiner Report dated Nov. 26, 2015", 2 pgs.
"Australian Application Serial No. 2013238046, Response filed Feb. 2, 2016 to First Examiner Report dated Nov. 26, 2015", 1 pg.
"Australian Application Serial No. 2013238054, First Examiner Report dated Oct. 17, 2016", 4 pgs.
"Australian Application Serial No. 2013238054, Response filed Jan. 18, 2017 to First Examiner Report dated Oct. 17, 2016", 9 pgs.
"Australian Application Serial No. 2015238820, First Examination Report dated May 30, 2017", 3 pgs.
"Australian Application Serial No. 2015238820, Response filed Jul. 12, 2017 to First Examination Report dated May 30, 2017", 12 pgs.
"Australian Application Serial No. 2017251736, First Examiners Report dated Oct. 31, 2017", 2 pgs.
"Canadian Application Serial No. 2,806,326, Response Filed Mar. 20, 2019 to Examiner Rule 30(2) Requisition dated Sep. 20, 2018", 4 pgs.
"Canadian Application Serial No. 2,821,927, Office Action dated Jan. 25, 2018", 6 pgs.
"Canadian Application Serial No. 2,821,927, Response filed Jul. 18, 2018 to Office Action dated Jan. 25, 2018", 10 pgs.
"Canadian Application Serial No. 2,821,927, Voluntary Amendment dated Jun. 14, 2013", 7 pgs.
"Canadian Application Serial No. 2,824,527, Office Action dated Mar. 17, 2014", 2 pgs.
"Canadian Application Serial No. 2,824,527, Response filed Sep. 17, 2014 to Office Action dated Mar. 17, 2014", 14 pgs.
"Canadian Application Serial No. 2,856,070, Preliminary Amendment filed May 25, 2015", 27 pgs.
"Canadian Application Serial No. 2,868,825, Office Action dated Dec. 27, 2018", 3 pgs.
"Canadian Application Serial No. 2,956,119, Response Filed May 27, 2019 to Examiner's Rule 30(2) Requisition dated Sep. 27, 2018", 7 pgs.
"Canadian Application Serial No. 2,989,184, Response filed Apr. 1, 2019 to Office Action dated Oct. 1, 2018", 10 pgs.
"Chinese Application Serial No. 201180067430.X, Office Action dated Aug. 28, 2014", (W/ English Translation), 8 pgs.
"Chinese Application Serial No. 201180067430.X, Response filed Jan. 4, 2015 to Office Action dated Sep. 26, 2014", (W/ English Translation), 14 pgs.
"Chinese Application Serial No. 201180067757.7, Office Action dated Mar. 2, 2015", (W/ English Translation), 18 pgs.
"Chinese Application Serial No. 201180067757.7, Office Action dated Jun. 1, 2016", (W/ English Translation), 10 pgs.
"Chinese Application Serial No. 201180067757.7, Office Action dated Nov. 16, 2015", (W/ English Translation), 17 pgs.
"Chinese Application Serial No. 201180067757.7, Response filed Jan. 27, 2016 to Office Action dated Nov. 16, 2015", (W/ English Translation of Claims), 12 pgs.

"Chinese Application Serial No. 201180067757.7, Response filed Jul. 10, 2015 to Office Action dated Mar. 2, 2015", (W/ English Translation), 13 pgs.
"Chinese Application Serial No. 201180067757.7, Response filed Aug. 11, 2016 to Office Action dated Jun. 1, 2016", (W/ English Translation of Claims), 9 pgs.
"Chinese Application Serial No. 201180067757.7, Voluntary Amendment dated Feb. 14, 2014", (W/ English Translation of Claims), 8 pgs.
"Chinese Application Serial No. 201280067481.7, Office Action dated Sep. 30, 2015", (W/ English Translation), 7 pgs.
"Chinese Application Serial No. 201380028572.4, Office Action dated Aug. 13, 2015", (W/ English Translation), 16 pgs.
"Chinese Application Serial No. 201380028683.5, Office Action dated Jun. 27, 2016", (W/ English Translation), 8 pgs.
"Chinese Application Serial No. 201380028683.5, Office Action dated Nov. 4, 2015", (W/ English Translation), 16 pgs.
"Chinese Application Serial No. 201380028683.5, Office Action dated Dec. 30, 2016", W/ English Translation), 4 pgs.
"Chinese Application Serial No. 201380028683.5, Response filed Feb. 8, 2017 to Office Action dated Dec. 30, 2016", W/ English Translation), 13 pgs.
"Chinese Application Serial No. 201380028683.5, Response filed Mar. 18, 2016 to Office Action dated Nov. 4, 2015", W/ English Translation of Claims), 11 pgs.
"Chinese Application Serial No. 201380028683.5, Response filed Sep. 6, 2016 to Office Action dated Jun. 27, 2016", (W/ English Translation of Claims), 11 pgs.
"Chinese Application Serial No. 201510394094.X, Office Action dated May 24, 2017", (W/ English Translation), 11 pgs.
"Chinese Application Serial No. 201510394094.X, Office Action dated Aug. 30, 2016", W/ English Translation), 14 pgs.
"Chinese Application Serial No. 201510394094.X, Office Action dated Nov. 3, 2017", W/ English Translation), 10 pgs.
"Chinese Application Serial No. 201510394094.X, Response filed Jan. 16, 2017 to Office Action dated Aug. 30, 2016", W/ English Translation of Claims), 11 pgs.
"Chinese Application Serial No. 201510394094.X, Response filed Jan. 18, 2018 to Office Action dated Nov. 3, 2017", (W/ English Claims), 10 pgs.
"Chinese Application Serial No. 201510394094.X, Response filed Jul. 10, 2017 to Office Action dated May 24, 2017", W/ English Translation), 10 pgs.
"Chinese Application Serial No. 201680061268.3, Office Action dated Apr. 24, 2019", W/ English Translation, 11 pgs.
"Complete Knee Solution Surgical Technique for the CR-Flex Fixed Bearing Knee", Zimmer Nexgen, (2003), 22 pgs.
"European Application Serial No. 11802835.6, Communication Pursuant to Article 94(3) EPC dated Dec. 11, 2017", 4 pgs.
"European Application Serial No. 11802835.6, Response filed Apr. 23, 2018 to Office Action dated Dec. 11, 2017", 16 pgs.
"European Application Serial No. 11808493.8, Communication Pursuant Article 94(3) EPC dated Dec. 7, 2015", 4 pgs.
"European Application Serial No. 11808493.8, Examination Notification Art. 94(3) dated Feb. 20, 2015", 6 pgs.
"European Application Serial No. 11808493.8, Response filed Feb. 26, 2014 to Communication pursuant to Rules 161(1) and 162 EPC dated Aug. 16, 2013", 14 pgs.
"European Application Serial No. 11808493.8, Response filed Apr. 18, 2016 to Communication Pursuant to Article 94(3) EPC dated Dec. 7, 2015", 15 pgs.
"European Application Serial No. 11808493.8, Response filed Jul. 2, 2015 to Examination Notification Art, 94(3) dated Feb. 20, 2015", 13 pgs.
"European Application Serial No. 12718882.9, Communication Pursuant to Article 94(3) EPC dated Dec. 1, 2015", 11 pgs.
"European Application Serial No. 12718882.9, Response filed Feb. 10, 2015 to Communication Pursuant to Rules 161(1) and 162 EPC dated Jul. 31, 2014", 11 pgs.
"European Application Serial No. 12718882.9, Response filed Apr. 11, 2016 to Communication Pursuant to Article 94(3) EPC dated Dec. 1, 2015", 12 pgs.

(56) References Cited

OTHER PUBLICATIONS

"European Application Serial No. 12718883.7, Communication Pursuant to Article 94(3) EPC dated Feb. 2, 2015", 4 pgs.
"European Application Serial No. 12718883.7, Communication Pursuant to Rules 161(1) and 162 EPC dated Jul. 31, 2014", 2 pgs.
"European Application Serial No. 12718883.7, Intention to Grant dated May 20, 2016", 5 pgs.
"European Application Serial No. 12718883.7, Response filed Feb. 10, 2015 to Communication Pursuant to Rules 161(1) and 162 EPC dated Jul. 31, 2014", 16 pgs.
"European Application Serial No. 12718883.7, Response filed Apr. 12, 2016 to Communication Pursuant to Article 94(3) EPC dated Dec. 2, 2015", 30 pgs.
"European Application Serial No. 12719236.7, Response filed Feb. 9, 2015 to Communication Pursuant to Rules 161(1) and 162 EPC dated Jul. 30, 2014", 10 pgs.
"European Application Serial No. 12719236.7, Decision to Grant dated Feb. 18, 2016", 3 pgs.
"European Application Serial No. 12719236.7, Office Action dated Aug. 27, 2015", 7 pgs.
"European Application Serial No. 12720352.9, Response filed Feb. 9, 2015 to Communication Pursuant to Rules 161(1) and 162 EPC dated Jul. 30, 2014", 10 pgs.
"European Application Serial No. 12756058.9, Communication Pursuant to Article 94(3) EPC dated Feb. 18, 2019", 4 pgs.
"European Application Serial No. 13716636.9, CommunicationPursuant to Article 94(3) EPC dated Nov. 16, 2015", 4 pgs.
"European Application Serial No. 13716636.9, Communication Pursuant to Article 94(3) EPC dated Nov. 17, 2016", 4 pgs.
"European Application Serial No. 13716636.9, Communication Pursuant to Article 94(3) EPC dated Jun. 6, 2016", 5 pgs.
"European Application Serial No. 13716636.9, Communication pursuant to Rules 161(1) and 162 EPC dated Dec. 12, 2014", 2 pgs.
"European Application Serial No. 13716636.9, Response filed Mar. 24, 2016 to Communication Pursuant to Article 94(3) EPC dated Nov. 16, 2015", 18 pgs.
"European Application Serial No. 13716636.9, Response filed Mar. 27, 2017 to Communication Pursuant to Article 94(3) EPC dated Nov. 17, 2016", 15 pgs.
"European Application Serial No. 13716636.9, Response filed Jun. 22, 2015 to Communication pursuant to Rules 161(1) and 162 EPC dated Feb. 12, 2014", 10 pgs.
"European Application Serial No. 13716636.9, Response filed Oct. 17, 2016 to Communication Pursuant to Article 94(3) EPC dated Jun. 6, 2016", 5 pgs.
"European Application Serial No. 14190180.1, Extended European Search Report dated Sep. 24, 2015", 8 pgs.
"European Application Serial No. 16156228.5, Extended European Search Report dated May 11, 2017", 5 pgs.
"European Application Serial No. 16183635.8, Extended European Search Report dated Jun. 30, 2017", 9 pgs.
"European Application Serial No. 16183635.8, Response filed Mar. 27, 2018 to Extended European Search Report dated Jun. 30, 2017", 8 pgs.
"European Application Serial No. 16770657.1, Communication Pursuant to Article 94(3) EPC dated May 20, 2019", 3 pgs.
"European Application Serial No. 17157909.7, Extended European Search Report dated Jul. 17, 2018", 7 pgs.
"European Application Serial No. 17157909.7, Response Filed Feb. 15, 2019 to Extended European Search Report dated Jul. 17, 2018", 37 pgs.
"European Application Serial No. 17168095.2, Response Filed Jan. 17, 2019 Extended European Search Report dated Jun. 8, 2018", 29 pgs.
"European Application Serial No. 17168308.9, Response Filed Jan. 17, 2019 to Extended European Search Report dated Jun. 13, 2018", 24 pgs.
"Gender Solutions Natural Knee Flex System: Because Men and Women are Different", Zimmer, Inc., (2007, 2009), 6 pg.
"Gender Solutions Natural Knee Flex System: Surgical Technique", Zimmer, Inc., (2007, 2008, 2009), 36 pgs.
"Indian Application Serial No. 1544/DELNP/2013, Office Action dated May 21, 2019", w/ English translation, 10 pgs.
"International Application Serial No. PCT/US2011/064435, International Preliminary Report on Patentability dated Jun. 27, 2013", 9 pgs.
"International Application Serial No. PCT/US2011/064435, Search Report dated Jun. 21, 2012", 5 pgs.
"International Application Serial No. PCT/US2011/064435, Written Opinion dated Jun. 21, 2012". 7 pgs.
"International Application Serial No. PCT/US2011/065683, International Preliminary Report on Patentability dated Jun. 27, 2013", 11 pgs.
"International Application Serial No. PCT/US2011/065683, International Search Report dated Apr. 24, 2012", 12 pgs.
"International Application Serial No. PCT/US2011/065683, Written Opinion dated Apr. 24, 2012", 10 pgs.
"International Application Serial No. PCT/US2012/035679, International Preliminary Report on Patentability dated May 30, 2014", 8 pgs.
"International Application Serial No. PCT/US2012/035679, International Search Report dated Jun. 8, 2012", 4 pgs.
"International Application Serial No. PCT/US2012/035679, Written Opinion dated Jun. 8, 2012", 7 pgs.
"International Application Serial No. PCT/US2012/035680, International Preliminary Report on Patentability dated May 30, 2014", 13 pgs.
"International Application Serial No. PCT/US2012/035680, Search Report dated Oct. 9, 2012", 7 pgs.
"International Application Serial No. PCT/US2012/035680, Written Opinion dated Oct. 9, 2012", 11 pgs.
"International Application Serial No. PCT/US2012/035683, International Preliminary Report on Patentability dated May 30, 2014", 9 pgs.
"International Application Serial No. PCT/US2012/035683, International Search Report and Written Opinion dated Jun. 5, 2012", 12 pgs.
"International Application Serial No. PCT/US2012/035684, International Preliminary Report on Patentability dated May 30, 2014", 14 pgs.
"International Application Serial No. PCT/US2012/035684, International Search Report dated Aug. 8, 2012", 9 pgs.
"International Application Serial No. PCT/US2012/035684, Written Opinion dated Jun. 8, 2012", pgs.
"International Application Serial No. PCT/US2013/034286, International Preliminary Report on Patentability dated Oct. 9, 2014", 8 pgs.
"International Application Serial No. PCT/US2013/034286, International Search Report dated Jun. 25, 2013", 6 pgs.
"International Application Serial No. PCT/US2013/034286, Written Opinion dated Jun. 25, 2013", 6 pgs.
"International Application Serial No. PCT/US2013/034293, International Preliminary Report on Patentability dated Oct. 9, 2014", 9 pgs.
"International Application Serial No. PCT/US2013/034293, International Search Report dated Jun. 25, 2013", 6 pgs.
"International Application Serial No. PCT/US2013/034293, Written Opinion dated Jun. 25, 2013", 7 pgs.
"Intramedullary Instrumentation Surgical Technique for the NexGen Cruciate Retaining & Legacy Posterior Stabilized Knee", Zimmer, Inc. Nexgen Complete Knee Solution, 97-5973-102, Rev, 1, (1995,1997,1998), 36 pgs.
"Japanese Application Serial No. 2013-544655, Office Action dated Mar. 8, 2016", (W/ English Translation), 8 pgs.
"Japanese Application Serial No. 2013-544655, Office Action dated Sep. 29, 2015", (W/ English Translation), 7 pgs.
"Japanese Application Serial No. 2013-544655, Response filed Jan. 4, 2016 to Office Action dated Sep. 29, 2015", (English Translation of Claims), 14 pgs.
"Japanese Application Serial No. 2013-544655, Response filed Jul. 14, 2016 to Office Action dated Mar. 8, 2016", (w/ English Translation of Claims), 13 pgs.

(56) References Cited

OTHER PUBLICATIONS

"Japanese Application Serial No. 2013-544858, Request for Examination filed Feb. 4, 2014", (With English Translation), 14 pgs.
"Japanese Application Serial No. 2014-121515, Notice of Reasons for Rejection dated Jan. 5, 2016", W/ English Translation), 9 pgs.
"Japanese Application Serial No. 2014-121515, Office Action dated Jun. 2, 2015", (W/ English Translation), 10 pgs.
"Japanese Application Serial No. 2014-121515, Response filed May 11, 2016 to Notice of Reasons for Rejection mailed Jan. 5, 2016", (W/ English Translation of Claims), 11 pgs.
"Japanese Application Serial No. 2014-121515, Response filed Aug. 20, 2015 to Office Action dated Jun. 2, 2015", W/ English Translation of Claims), 6 pgs.
"Japanese Application Serial No. 2014-542297, Office Action dated May 31, 2016", (W/ English Translation of Claims), 6 pgs.
"Japanese Application Serial No. 2014-542297, Office Action dated Jun. 30, 2015", W/ English Translation), 10 pgs.
"Japanese Application Serial No. 2014-542297, Office Action dated Nov. 24, 2015", (W/ English Translation), 10 pgs.
"Japanese Application Serial No. 2014-542297, Response filed Feb. 23, 2016 to Office Action dated Feb. 24, 2015", (W/ English Translation of Claims), 15 pgs.
"Japanese Application Serial No. 2014-542297, Response filed Jun. 8, 2016 to Office Action dated May 31, 2016", W/ English Translation of Claims), 14 pgs.
"Japanese Application Serial No. 2014-542297, Response filed Sep. 28, 2015 to Office Action dated Jun. 30, 2015", W/ English Translation of Claims), 16 pgs.
"Japanese Application Serial No. 2015-503563, Office Action dated Dec. 20, 2016", (W/ English Translation), 10 pgs.
"Japanese Application Serial No. 2015-503563, Response Filed Mar. 13, 2017 to Office Action dated Dec. 20, 2016", W/ English Translation), 9 pgs.
"Japanese Application Serial No. 2016-145390, Office Action dated Apr. 25, 2017", (W/ English Translation), 5 pgs.
"Japanese Application Serial No. 2016-145390, Response filed Jul. 3, 2017 to Office Action dated Apr. 25, 2017", (W/ English Translation of Claims), 16 pgs.
"Legacy Implant Options", Nexgen Complete Knee Solution, (2002), 8 pgs.
"MIS Minimally Invasive Solution, The MIG Unicompartmental Knee Minimally Invasive Surgical Technique", Zimmer, Inc. Nexgen Complete Knee Solution, 97-5791-02, (Aug. 14, 2008), 27 pgs.
"Multi-Reference 4-in-1 Femoral Instrumentation Surgical Technique for NexGen Cruciate Retaining & NexGen Legacy Posterior Stabilized Knees", Zimmer, Inc. Nexgen Complete Knee Solution, 97-5973-402 Rev. 1, (1998, 2000), 18 pgs.
"Natural-Knee II Primary System Surgical Technique", Zimmer, Inc., (2005), 48 pgs.
"Nexgen Complete Knee Solution for the Legacy Knee LPS-Flex Fixed Bearing Knee", Zimmer Surgical Technique, 97-5964-102-00, (2004, 2007), 12 pgs.
"NexGen Complete Knee Solution, Intramedullary Instrumentation Surgical Technique for the NexGen Cruciate Retaining & Legacy Posterior Stabilized Knee", Zimmer, Inc., (1995, 1997, 1998), 1-33.
"NexGen Implant Options Surgeon-Specific", Zimmer Inc., (2000), 16 pgs.
"NexGen LPS Fixed Knee: Surgical Technique", Zimmer Inc., (2002, 2008), 44 pgs.
"NexGen LPS-Flex Mobile and LPS-Mobile Bearing Knees", Zimmer, Inc., (2007, 2008), 4 pgs.
"Primary/Revision Surgical Technique for NexGen Rotating Hinge Knee (RHK)", Zimmer, Inc, Nexgen Complete Knee Solution, 9-5880-02, (2002), 116 pgs.
"Revision Instrumentation Surgical Technique for Legacy Knee Constrained Condylar Knee", Zimmer, Inc. Nexgen Complete Knee Solution, 97-5994-202, (2001), 61 pgs.

"Surgical Technique for Cruciate Retaining Knees and Revision Instrumentation Surgical Technique for Cruciate Retaining Augmentable Knees", Zimmer, Inc. Nexgen Complete Knee Solution, 97-5970-202, (2002), 130 pgs.
"Surgical Technique for the Legacy Knee LPS-Flex Fixed Bearing Knee", Zimmer, Inc, Nexgen Complete Knee Solution, 97-5964-02, Rev. 1, (2000, 2002), 15 pgs.
"Surgical Technique for the Legacy Posterior Stabilized Knees", Zimmer, Inc, Nexgen Complete Knee Solution, 97-5996-02, (2002), 43 pgs.
"Surgical Technique—Nexgen Complete Knee Solution for the Legacy Knee LPS-Flex Fixed Bearing Knee", Zimmer, Inc., (2004, 2007), 12 pgs.
"The Zimmer Institute Surgical Technique MIS Quad-Sparing Surgical Technique for Total Knee Arthroplasty", NExGen Complete Knee Solution, (2004), 55 pgs.
"Zimmer MIS Intramedullary Instrumentation Surgical Technique for NexGen Cruciate Retaining & NexGen Legacy Posterior Stabilized Knees", printed 2005, 2009, Zimmer, Inc., (2009), 45 pgs.
"Zimmer Nexgen Cruciate Retaining (CR) and Legacy Knee Posterior Stabilized (LPS) Trabecular Metal Monoblock Tibias", Zimmer, Inc Surgical Technique Addendum, 97-725334, Rev, 3, (2004), 11 pgs.
"Zimmer NexGen CR-Flex and LPS-Flex Knees Surgical Technique with posterior Referencing Instrumentation.", Zimmer Inc., (2010, 2011), 48 pgs.
"Zimmer NexGen LCCK Surgical Technique for use with Lock 4-in-1 Instrumentation", Zimmer, Inc.; copyright 2009, 2010, 2011, (May 2011), 52 pgs.
"Zimmer NexGen MIS Modular Tibial Plate and Keel Cemented Surgical Technique", Zimmer Inc., (2006, 2011), 26 pgs.
"Zimmer NexGen MIS Tibial Component", Brochure-97-5950-001-00 7.5mm, (2005, 2006), 8 pgs.
"Zimmer NexGen MIS Tibial Component Cemented Surgical Technique", Zimmer, Inc, #97-5950-002-00 Rev,1 1.5ML, (2005), 14 pgs.
"Zimmer NexGen MIS Tibial Component Cemented Surgical Technique", Zimmer Inc., (2005, 2006, 2008, 2009, 2010), 16 pgs.
"Zimmer NexGen Trabecular Metal Augments—Abbreviated Surgical Technique", Zimmer, Inc., (2004, 2006), 6 pgs.
"Zimmer NexGen Trabecular Metal Augments Surgical Technique for LCCK & Rotating Hing Knee Trabecular Metal Augments", Zimmer, Inc. 97-5448-02, Rev. 1, (2004), 6 pgs.
"Zimmer NexGen Trabecular Metal Primary Patella Surgical Technique", Zimmer. Inc., 97-7255-112-00, (2005), 10 pgs.
"Zimmer NexGen Trabecular Metal Tibial Tray", Surgical Technique, Zimmer, Inc., (2007, 2009), 16 pgs.
"Zimmer Patient Specific Instruments", Surgical Techniques for NexGen Complete Knee Solution Zimmer, Inc., (2010), 16 pgs.
Hofmann, Aaron A et al., "Posterior Stabilization in Total Knee Arthroplasty with Use of an Ultracongruent Polyethylene", The Journal of Arthroplasty vol. 15, No. 5, (2000), 576-583.
Partovi, Hamid, "Flow-Through Latch and Edge-Triggered Flip-Flop Hybrid Elements", Proceedings of the IEEE International Solid-State Circuits Conference, Digital of Technical Papers and Slide Supplement, NexGen Inc. Milpitas, CA, (1996), 40 pgs.
"Persona "Medial Congruent Articular Surface" System Overview", Zimmer, Inc., (2015), 6 pgs.
"Persona "The Personalized Knee System"", Medial Congruent Sales Training, Zimmer, Inc., (Jul. 2015), 53 pgs.
"Persona "The Personalized Knee System" Medial Congruent Advanced Bearings", Zimmer, Inc., (2015), 2 pgs.
"Persona "The Personalized Knee System" Medial Congruent Articular Surface Design Rationale", Zimmer, Inc., (2015), 20 pgs.
"Persona "The Personalized Knee System" Persona Medial Congruent", Mar. 24-28, 2015 at the American Academy of Orthopaedic Surgeons (AAOS) Annual Meeting., (Mar. 2015), 1 pg.
"Persona "The Personalized Knee System" Surgical Technique", Zimmer, Inc., (2015), 72 pgs.
"Persona Medial Congruent Articular Surface", Sales Training, Zimmer Biomet, (Jan. 2016), 71 pgs.

(56) References Cited

OTHER PUBLICATIONS

Freeman, M.A.R., et al., "The Movement of the Knee Studied by Magnetic Resonance Imaging", Advanced Bearings—Clinical Orthopedics & Related Research 2003, (2003), 1 pg.

Siggelkow, Eik, et al., "Impact of Tibia Bearing Surface and Femoral Component Design on Flexion Kinematics During Lunge", Mar. 28-31, 2015 at the Orthopaedic Research Society (ORS) Annual Meeting (Poster #1645), (Mar. 2015), 1 pg.

Siggelkow, Eik, et al., "Impact of Tibia Bearing Surface Design on Deep Knee Bend Kinematics", Mar. 24-28, 2015 at the AAOS Conference (Poster #P142), (Mar. 2015), 1 pg.

* cited by examiner

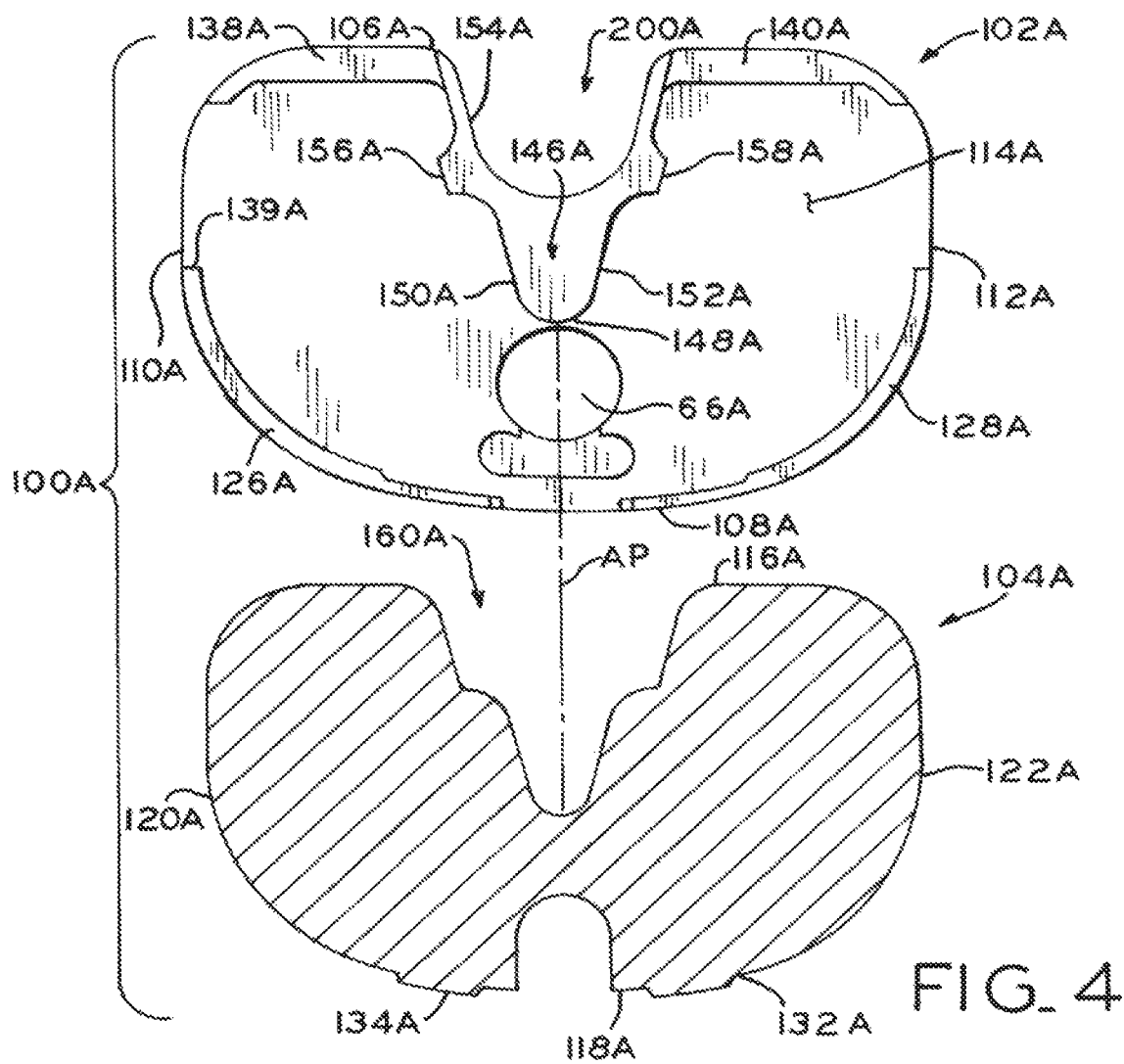
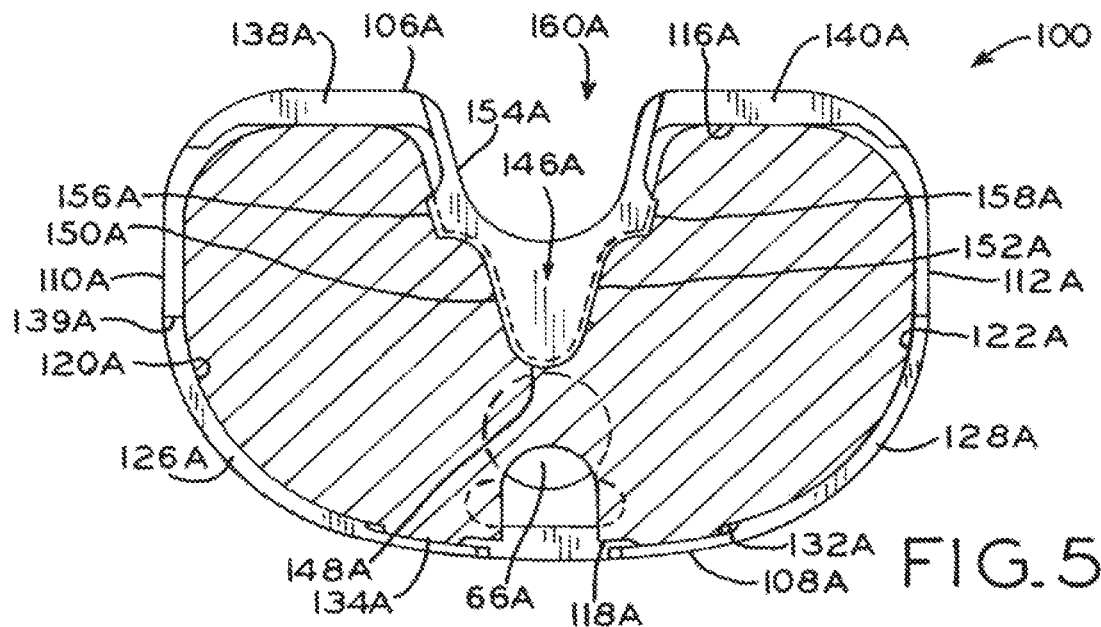

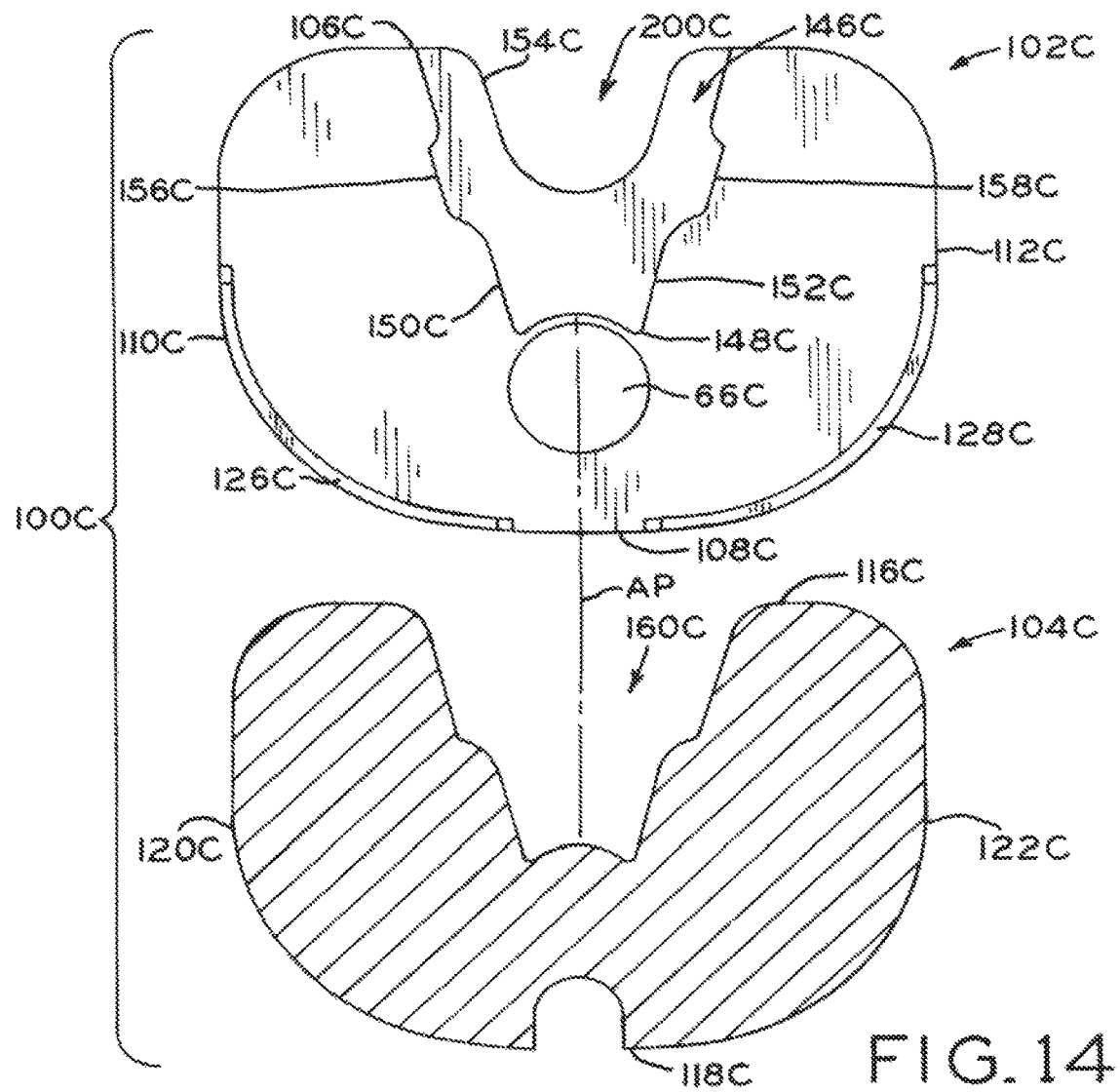
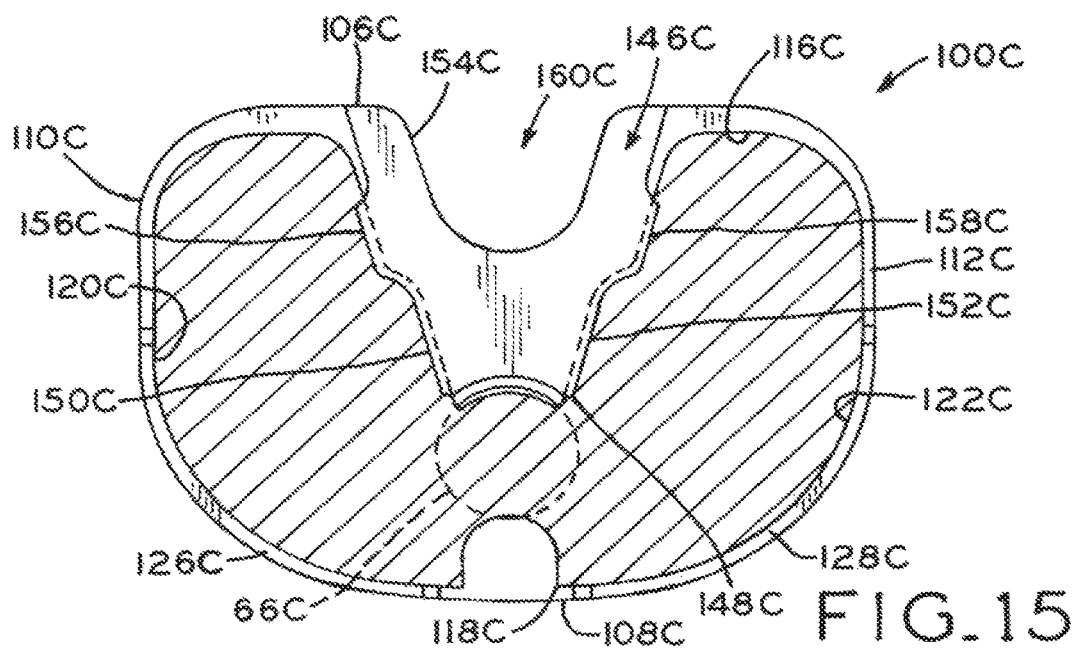
FIG. 14
FIG. 15

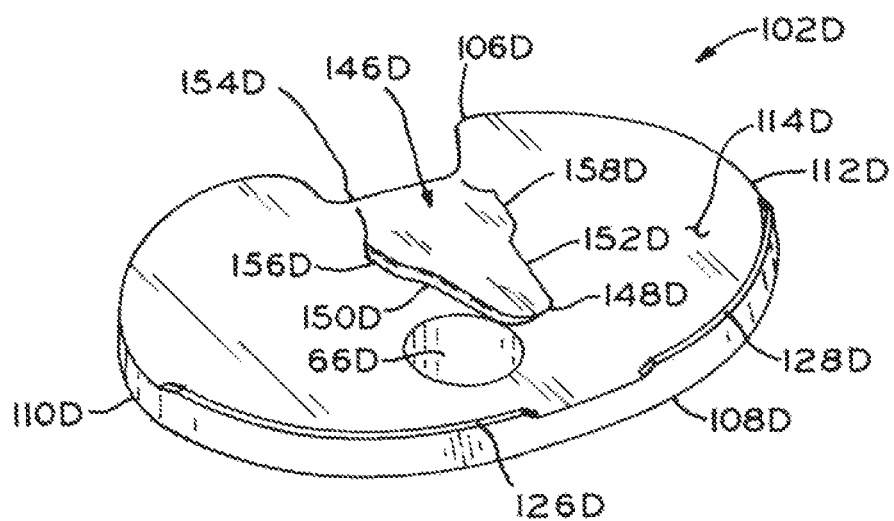
FIG_17
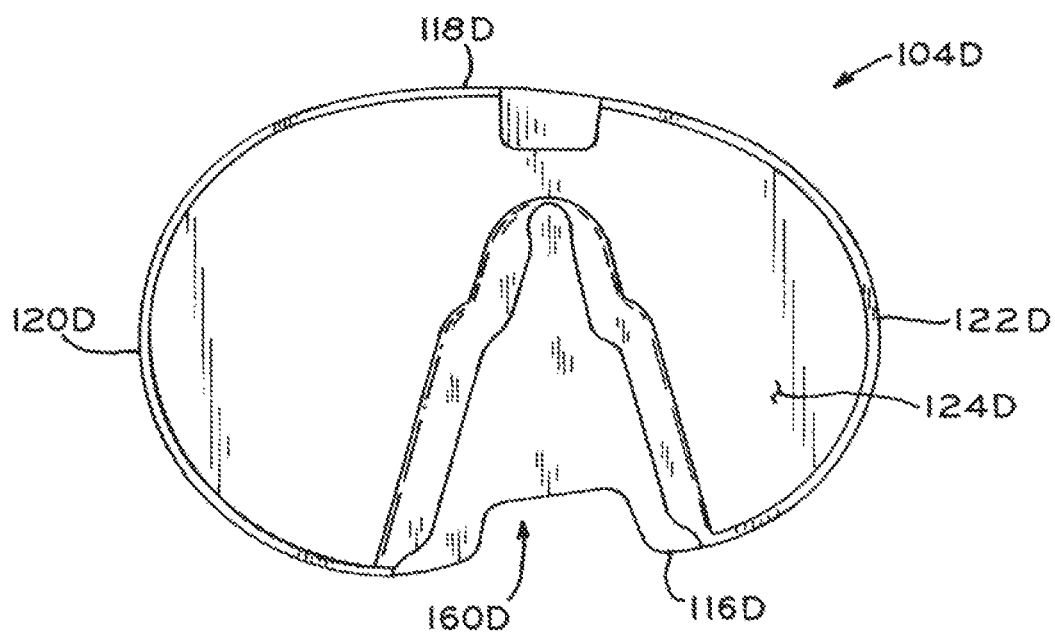
FIG_18

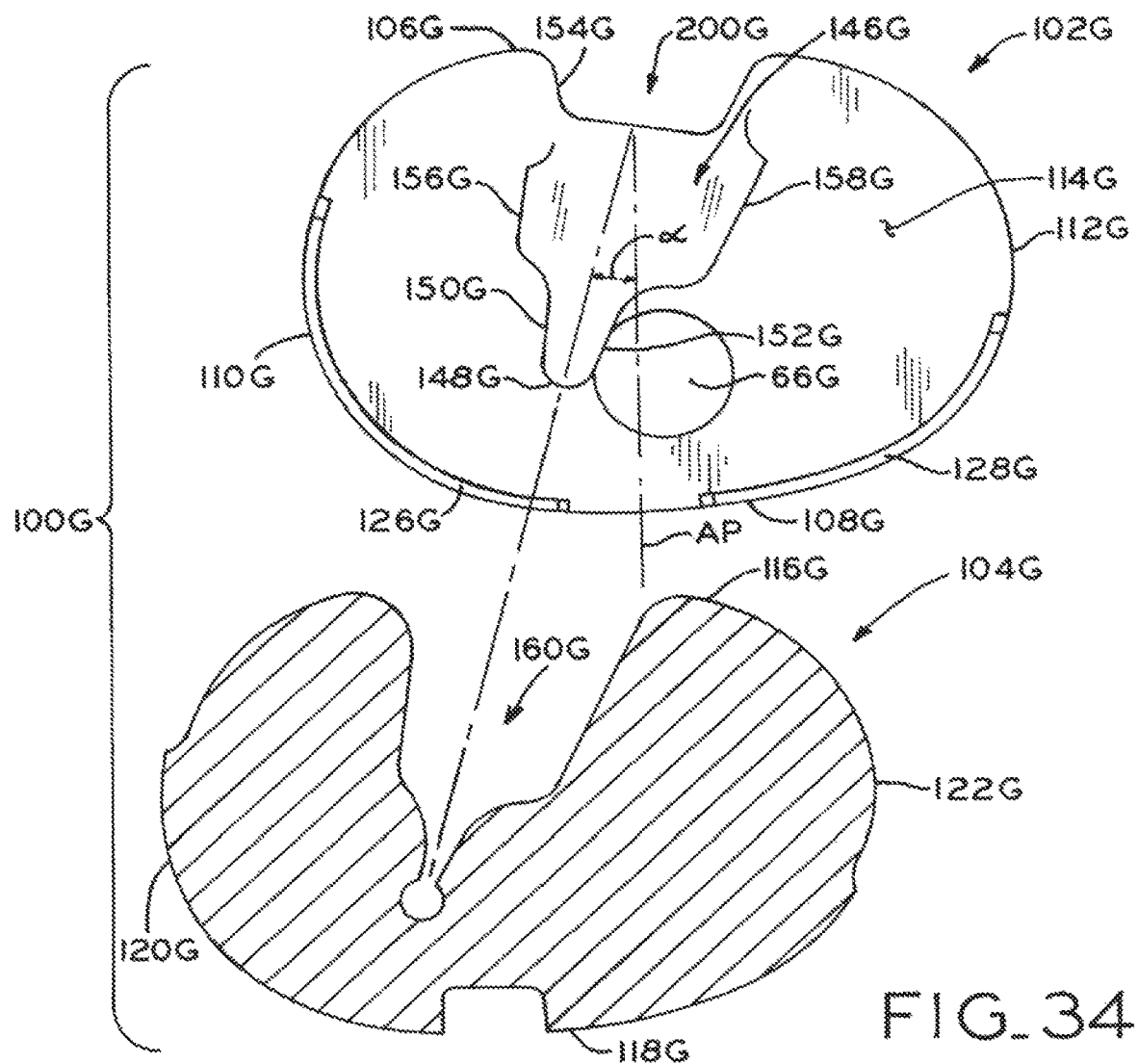
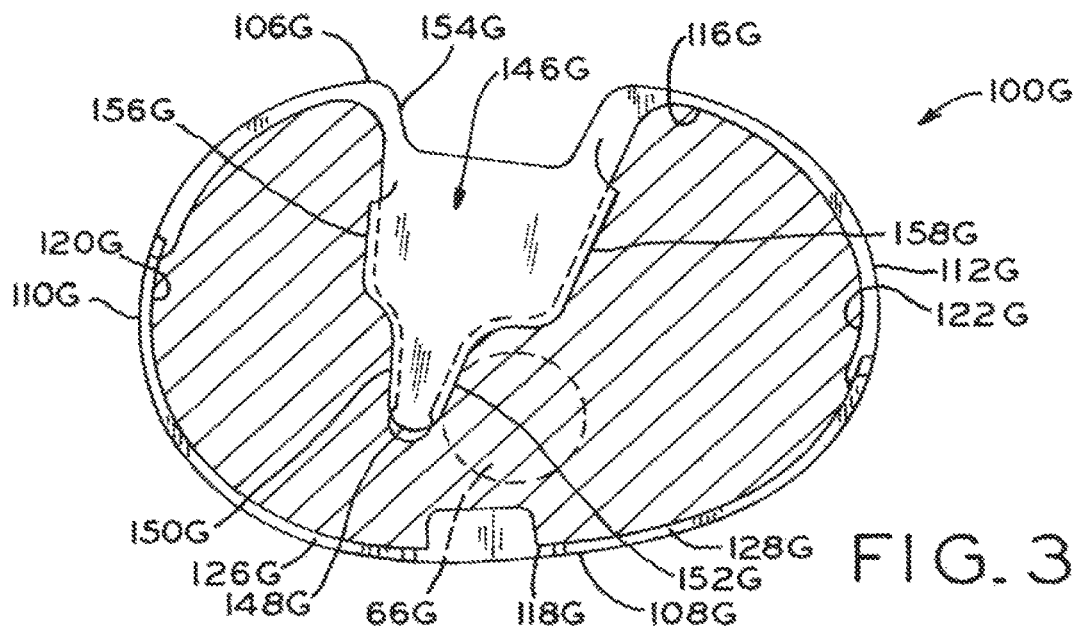
FIG. 34
FIG. 35

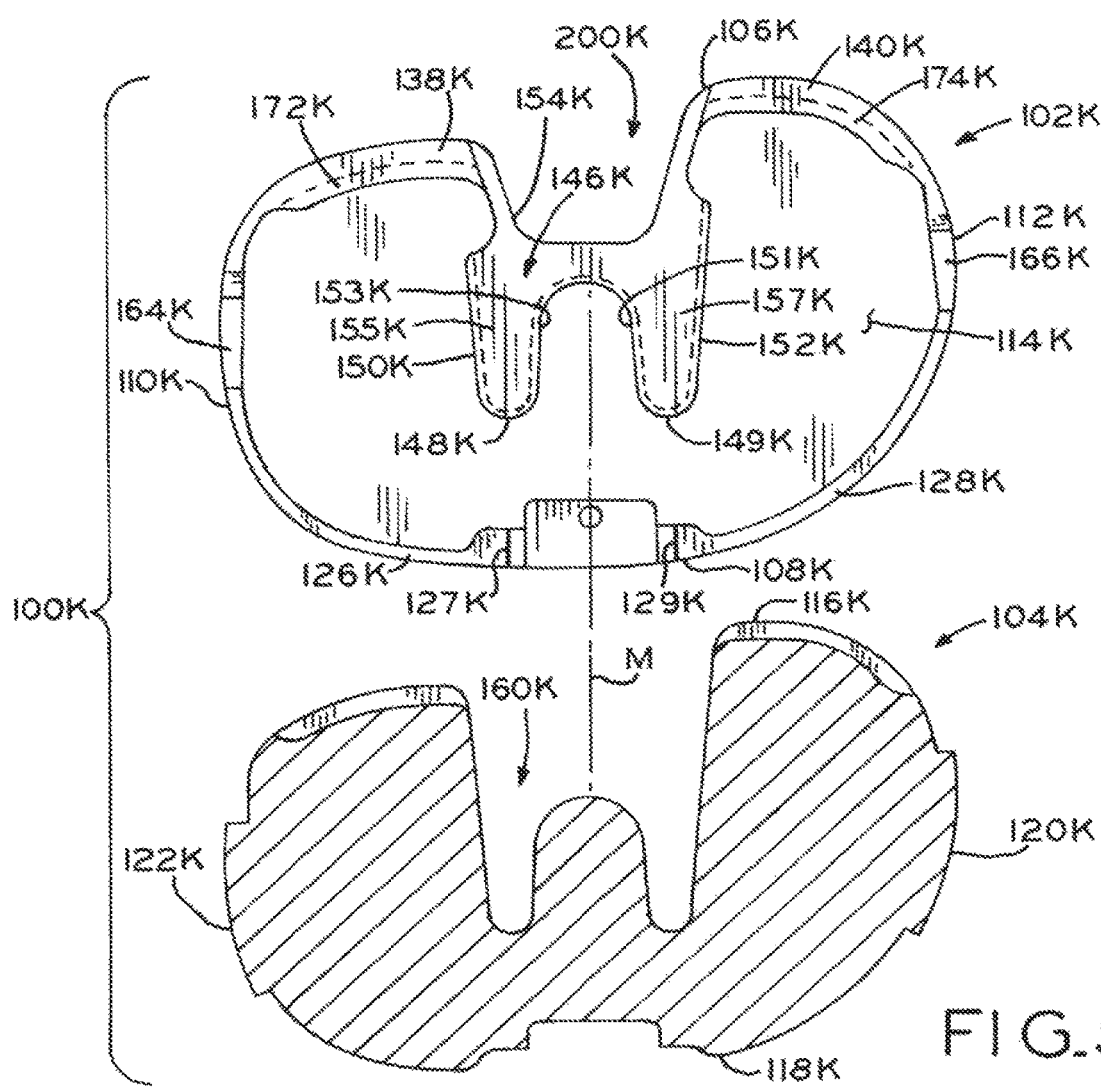
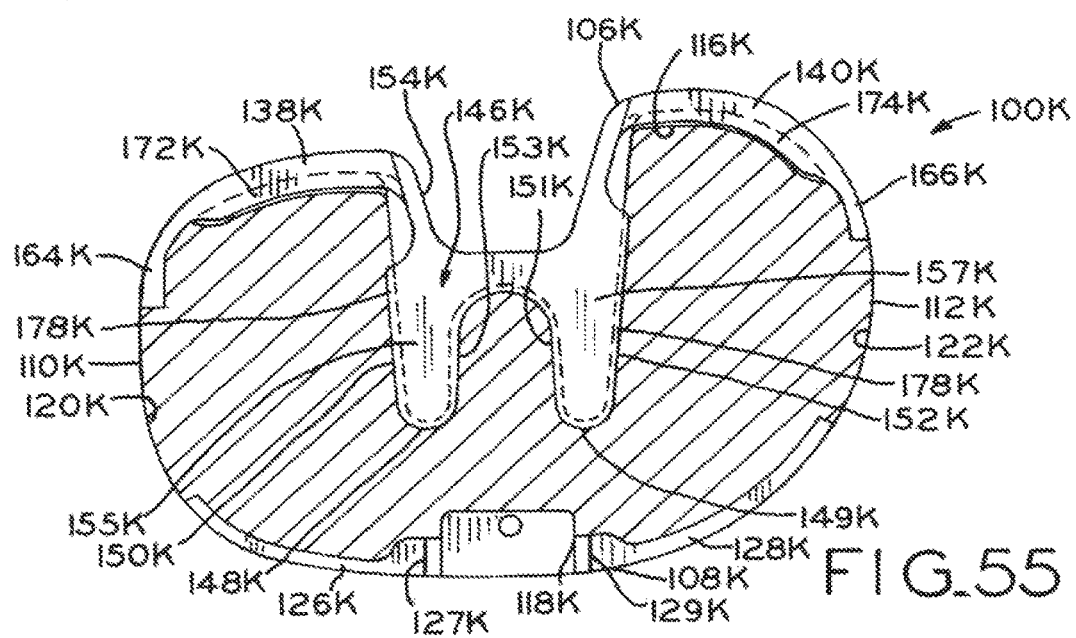

TIBIAL PROSTHESIS

CROSS-REFERENCE TO RELATED APPLICATIONS

This application is a continuation of U.S. patent application Ser. No. 14/063,593, filed Oct. 25, 2013, now issued as U.S. Pat. No. 9,763,794, which is a continuation of U.S. patent application Ser. No. 13/189,328, filed Jul. 22, 2011, now issued as U.S. Pat. No. 8,628,580, which claims the benefit under Title 35 U.S.C. § 119(e) of U.S. Provisional Patent Application Ser. No. 61/367,374, filed on Jul. 24, 2010 and entitled TIBIAL PROSTHESIS, and U.S. Provisional Patent Application Ser. No. 61/367,375, filed on Jul. 24, 2010 and entitled TIBIAL PROSTHESIS, the entire disclosures of which are hereby expressly incorporated by reference herein.

BACKGROUND

1. Field of the Invention

The present invention relates to orthopedic prostheses and, particularly, to proximal tibial prostheses.

2. Description of the Related Art

Orthopedic prostheses are commonly utilized to repair and/or replace damaged bone and tissue in the human body. For example, a knee prosthesis may be implanted during a total knee arthroplasty to replace damaged or destroyed bone in the tibia and/or femur and to recreate the natural, anatomical articulation of the knee joint. The knee prosthesis may include a femoral prosthesis shaped to replicate one or both of the natural femoral condyles. After resecting the distal end of the femur, one side of the femoral prosthesis is secured to the femur and the opposing side of the femoral prosthesis is configured for articulation against a tibial prosthesis.

A tibial prosthesis may include a first bearing component having a concave articular portion configured for articulation with the femoral prosthesis. The bearing component of the tibial prosthesis may be secured to a tibial tray. The tibial tray has a side secured to the bone stock of a resected proximal tibia. By securing the bearing component of the tibial prosthesis to the tibial tray to prevent translation and/or rotation of the bearing component relative to the tibial tray, a fixed bearing tibial prosthesis is created. The bearing component of the tibial prosthesis may be made from a polymeric material to facilitate articulation with the femoral component, while the tibial tray of the tibial prosthesis may be made from a metallic material to provide sufficient strength and rigidity to the tibial prosthesis. The femoral prosthesis and the tibial prosthesis seek to replicate the natural anatomical articulation of the knee joint.

SUMMARY

The present disclosure relates to a tibial prosthesis, and, particularly, a fixed bearing tibial, prosthesis having a two-pronged securement mechanism. The securement mechanism may or may not be angled. Advantageously, the securement mechanism, working alone or in cooperation with other securement features, minimizes micromotion between the tibial tray and tibial bearing component.

As used herein, "micromotion" refers to the small motions that may exist between prosthesis components, such as between tibial trays 102A-102L and bearing components 104A-104L respectively, upon application of force. Such small motions may occur as a result of material deformation in one or both of the interacting components, or may result from slight spaces or clearances therebetween, for example. Micromotion is distinguished from "mobile bearing" applications, which experience relatively larger motions as a tibial bearing articulates with respect to a tibial tray (such as by sliding or rotating) along a desired motion path.

As used herein, a "fixed bearing" tibial prosthesis is a prosthesis in which a bearing component is seated atop the tibial tray in a final, locked position. In this locked position, lift-off of the bearing component from the tibial tray as well as transverse movement of the bearing component relative to the tibial tray is prevented during natural articulation of the knee. While some micromotion may exist between the tibial bearing component and tibial tray in a fixed bearing prosthesis, no such motion occurs by design along a designated path.

A locking mechanism may be employed to fix the bearing component to the tibial tray, thereby creating a fixed bearing prosthesis. Such as a mechanism may including a dovetail boss on the tibial tray cooperating with a corresponding notch on a bearing component, a peripheral rail of the tibial tray cooperating with a corresponding recessed portion of the bearing component, a pair of anterior wedges projecting from an anterior edge of the bearing component that cooperate with an undercut within an anterior peripheral rail of the tibial tray, or any combination of these devices. Locking mechanisms of the present disclosure may also dictate the insertion trajectory of the bearing component relative to the tibial tray.

The dovetail boss of the present disclosure assists with locking a bearing component onto the tibial tray and also guides insertion of the bearing component into engagement with the tibial tray. Each boss has a pair of sides, one of which faces a lateral edge of the tibial tray and the other of which faces a medial edge of the tibial tray. In certain embodiments, the boss cooperates with a secondary locking mechanism to prevent lift-off of the bearing component from the tibial tray well as transverse movement of the bearing component relative to the tibial tray. The boss may have a sufficient anteroposterior length and/or mediolateral width to provide sufficient resistance to lift-off and lateral, movement of the bearing component while eliminating the need for a secondary locking mechanism between the bearing component and the tibial tray.

While a boss may assist as a locking mechanism to lock a bearing component onto a respective tibial tray, the boss may also assist with the orientation of the trajectory for insertion of the bearing component atop the tibial tray during knee surgery. For example, a boss may be angled, or canted, with respect to a reference axis. Alternatively, the boss may not be angled, or not be canted, with respect to the reference axis such that the boss follows a trajectory paralleling the reference axis.

As used herein, "reference axis" refers to a generally anterior-posterior axis that is parallel to a sagittal plane, i.e., a plane that centrally separates a body into right and left halves. Alternatively, the "reference axis" may be an axis, described in detail below, which links the medial one-third of the tibial tubercle with a geometric center of an attachment area between posterior cruciate ligament ("PCL") and the tibia.

Further, angled bosses may be configured to allow for an anterior-medial insertion of a bearing component onto and later attachment to a tibial tray of the tibial prosthesis. For the purposes of this document, "anterior-medial insertion" means insertion along a path from a starting point displaced anteriorly and medially from the desired final position of the implant.

The bearing component may be inserted along an anterior-medial insertion path and urged into a fixed position with the tibial tray along a single anterior-medial insertion trajectory. A locking mechanism engages as the bearing component is urged into the fixed position to lock the bearing component to the tibial tray. Fixation is completed when the bearing component is at the end of its travel and is fixed to the tibial tray to form a fixed-bearing tibial prosthesis. Such an anterior-medial insertion trajectory is additionally described in related U.S. patent application Ser. No. 13/189,324, entitled TIBIAL PROSTHESIS and filed on the same day as this present disclosure, the entire disclosure of which is expressly incorporated by reference herein.

The sides of the boss may be angled relative to an offset axis that is angled about 8 to 10 degrees from an axis parallel to the sagittal plane, though offset axis angles ranging from between about 0 to 90 degrees are contemplated. For instance, a lateral side and a medial side of the boss may each be angled relative to the offset axis at a lateral side angle and a medial side angle, respectively. The lateral side and medial side angles may range from about 5 degrees to 10 degrees, though angles ranging from between about 0 degrees to 15 degrees are contemplated. Also contemplated is an angle as small as 0, 1, 2, 3, 4, 5, 6, or 7 degrees or as great as 8, 9, 10, 11, 12, 13, 14, or 15 degrees, or may be my degree valued within any range defined by any of the foregoing values. Each side may be parallel to or angled with respect to the offset axis at a same or different angle from the other side. The geometry of this alternative tibial boss allows an anterior-medially inserted bearing component to be urged into a final, fixed, position along an anterior-medial insertion trajectory corresponding to the angle of the elongated sides of the tibial tray boss to complete seating of the bearing component atop the tibial tray. Advantageously, this anterior-medial insertion facilitates avoidance of the extensor mechanism of the knee during the implantation of the bearing component.

Referring back to the peripheral rail locking mechanism discussed above, the peripheral rail may include a pair of anterior rails. In certain embodiments, the peripheral rail may include posterior rails extending around the posterior periphery of the tibial tray. These posterior rails may also extend into medial and lateral edges of the tibial tray. Any of the peripheral rails may include undercuts, such that the peripheral rails are received into a corresponding internal groove of a respective bearing component. Alternatively, any of the peripheral rails may include "containment rails" which superiorly project from a support surface of a tibial tray and have a substantially straight edge for abutment against a corresponding edge of the bearing component after the bearing component has been seated onto the tibial tray. A "boss rail" may be provided, extending away from the periphery and rising superiorly from the support surface of the tibial tray. The peripheral rails may be of substantially the same thickness or may vary in thickness.

While certain embodiments of this disclosure include a posterior-medial edge of both a tibial tray and a bearing component that is symmetric with a posterior-lateral edge of the tibial tray and bearing component, the above-referenced edges may be asymmetric with each other. Any of the embodiments of the present disclosure may include posterior-medial and posterior-lateral edges that are either symmetric or asymmetric.

In one form thereof, the present disclosure provides a tibial prosthesis, comprising: a bearing component comprising: at least one concave articulating surface; a distal surface opposite the concave articulating surface; a peripheral wall extending between the articulating surface and the distal surface, the peripheral wall having an anterior bearing edge, an opposing posterior bearing edge, a lateral bearing edge and an opposing medial bearing edge; and a notch formed in the distal surface, the notch defining a bearing undercut; and a tibial tray comprising: a support surface capable of supporting the bearing component, the support surface defining an anterior tray edge, an opposing posterior tray edge, a lateral tray edge and an opposing medial tray edge; a two-pronged boss including a medial prong having a medially facing side and a laterally facing side, and a lateral prong having a medially facing side and a laterally facing side; and a tray undercut extending along the medial tray edge, the posterior tray edge, the lateral tray edge, the medially facing side and the laterally facing side of the medial prong, and the medially facing side and the laterally facing side of the lateral prong; the tray undercut cooperating with the bearing undercut to define an interference fit.

In another form thereof, the present disclosure provides a tibial tray comprising: a support surface capable of supporting the bearing component the support surface defining an anterior tray edge, an opposing posterior tray edge, a lateral tray edge and an opposing medial tray edge; and a two-pronged boss including a medial prong having a medially facing side and a laterally facing side, and a lateral prong having a medially facing side and a laterally facing side, the medial prong spaced from the lateral prong, the medially facing side of the medial prong convergent with the laterally facing side of the lateral prong toward the anterior edge.

In another form thereof, the present disclosure provides a tibial prosthesis for replacing at least part of a natural knee of a body, the body defining a sagittal plane which centrally separates the body into right and left halves, the tibial prosthesis comprising: a bearing component comprising: at least one concave articulating surface; a distal surface opposite the concave articulating surface; and a notch formed in the distal surface, the notch defining a longitudinal axis, the longitudinal axis defining an offset axis angle relative to the sagittal plane, the offset axis angle ranging from greater than zero degrees to about 90 degrees; and a tibial tray comprising: a support surface capable of supporting the bearing component, the support surface having a lateral edge and a medial edge opposite the lateral edge, and a boss having an a longitudinal axis, the longitudinal axis angled with respect to the sagittal plane, the boss lockingly engageable with the notch along the offset axis angle to lock the tibial tray to the bearing component.

BRIEF DESCRIPTION OF THE DRAWINGS

The above-mentioned and other features and advantages of this disclosure, and the manner of attaining them, will become more apparent and the invention itself will be better understood by reference to the following descriptions of embodiments of the invention taken in conjunction with the accompanying drawings, wherein:

FIG. 4 is a proximal plan, partial sectional view of the tibial prosthesis showing a straight insertion, along a general anterior-posterior axis parallel to a sagittal plane, of the bearing component onto the tibial tray of the first embodiment;

FIG. 5 is a proximal plan, partial sectional view of the tibial prosthesis of FIG. 4, with the bearing component fully seated on the tibial tray;

FIG. 14 is a proximal plan, partial sectional view of the tibial prosthesis showing a straight insertion, along a general anterior-posterior axis parallel to a sagittal plane, of the bearing component onto the tibial tray of the third embodiment;

FIG. 15 is a proximal plan, partial sectional view of the tibial prosthesis of FIG. 14, with the bearing component fully seated on the tibial tray;

FIG. 17 is a anterior perspective view of the tibial tray of the fourth embodiment;

FIG. 18 is a distal plan view of the bearing component of the fourth embodiment;

FIG. 34 is a proximal plan, partial sectional view of the tibial prosthesis showing an anterior-medial insertion at an angle of the bearing component onto the tibial tray of the seventh embodiment;

FIG. 35 is a proximal plan, partial sectional view of the tibial prosthesis of FIG. 34, with the bearing component fully seated on the tibial tray;

FIG. 54 is a proximal plan, partial sectional view of the tibial prosthesis showing a straight insertion, along an anatomic home axis, of the bearing component onto the tibial tray of the eleventh embodiment;

FIG. 55 is a proximal plan, partial sectional view of the tibial prosthesis of FIG. 54, with the bearing component fully seated on the tibial tray;

Corresponding reference characters indicate corresponding parts throughout the several views. The exemplifications set out herein illustrate exemplary embodiments of the invention, and such exemplifications are not to be construed as limiting the scope of the disclosure in any manner.

DETAILED DESCRIPTION

The present disclosure relates to a tibial prosthesis, and, particularly, a fixed bearing tibial prosthesis including a tibial tray for securement to the proximal tibia for a knee prosthesis. With the fixed bearing tibial prosthesis, a bearing component is seated atop the tibial tray in a final, locked position in which lift-off of the bearing component from the tibial tray as well as lateral movement of the bearing component relative to the tibial tray is prevented during natural articulation of the knee via a mechanism locking the bearing component to the tibial tray. The locking mechanism may include a dovetail boss on the tibial tray cooperating with a corresponding notch on a bearing component, a peripheral rail of the tibial tray cooperating with a corresponding recessed portion of the bearing component, a pair of anterior wedges projecting from an anterior edge of the bearing component that cooperate with an undercut within an anterior peripheral rail of the tibial tray, or any combination of these devices. Locking mechanisms of the present disclosure may also dictate the insertion trajectory of the bearing component relative to the tibial tray.

The boss may assist with the orientation of the trajectory for insertion of the bearing component atop the tibial tray during knee surgery. For example, a boss may be angled, or canted, with respect to a reference axis. Alternatively, the boss may not be angled, or not be canted, with respect to the reference axis such that the boss follows a trajectory paralleling the reference axis. As noted above, the reference axis may be a generally anterior-posterior axis that is parallel to a sagittal plane, i.e., a plane that centrally separates a body into right and left halves.

Alternatively, the reference axis may be a "home axis." In the context of patient anatomy, "home axis" M (FIG. 57) refers to a generally anteroposterior axis extending from posterior point $C_P$ to an anterior point $C_A$, in which anterior point $C_A$ is disposed on tubercle B and medially spaced from tubercle peak $P_T$ by an amount equal to W/6 (i.e., point $C_A$ lies on the "medial third" of the anterior tibial tubercle).

Figure 57:
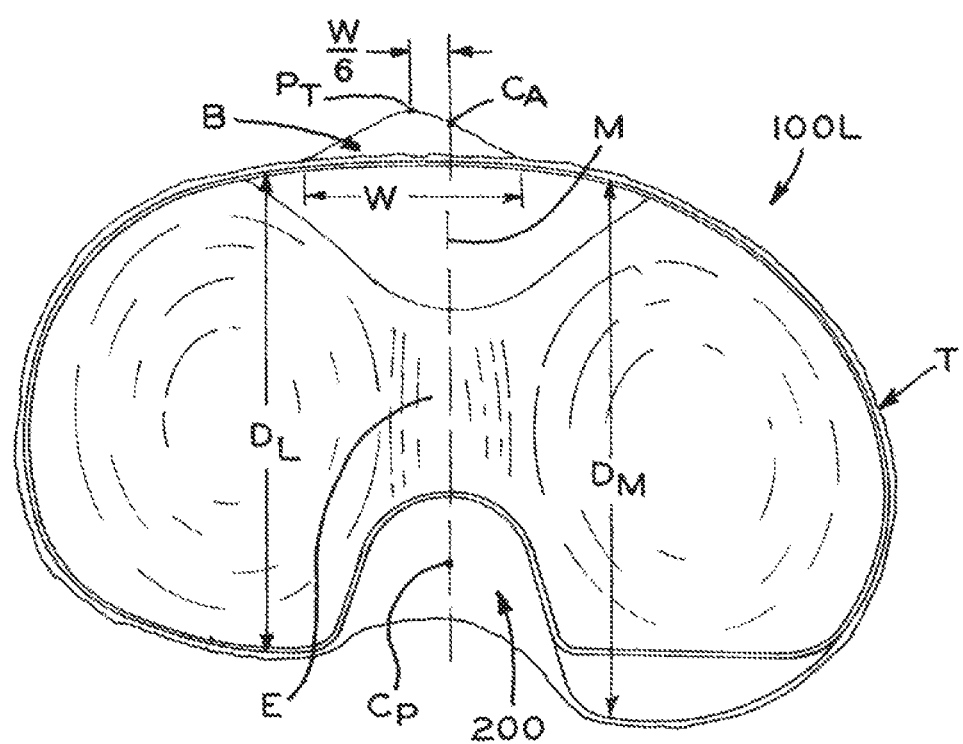
FIG. 57 is a top plan view of a resected proximal tibial surface.
Figure 58:
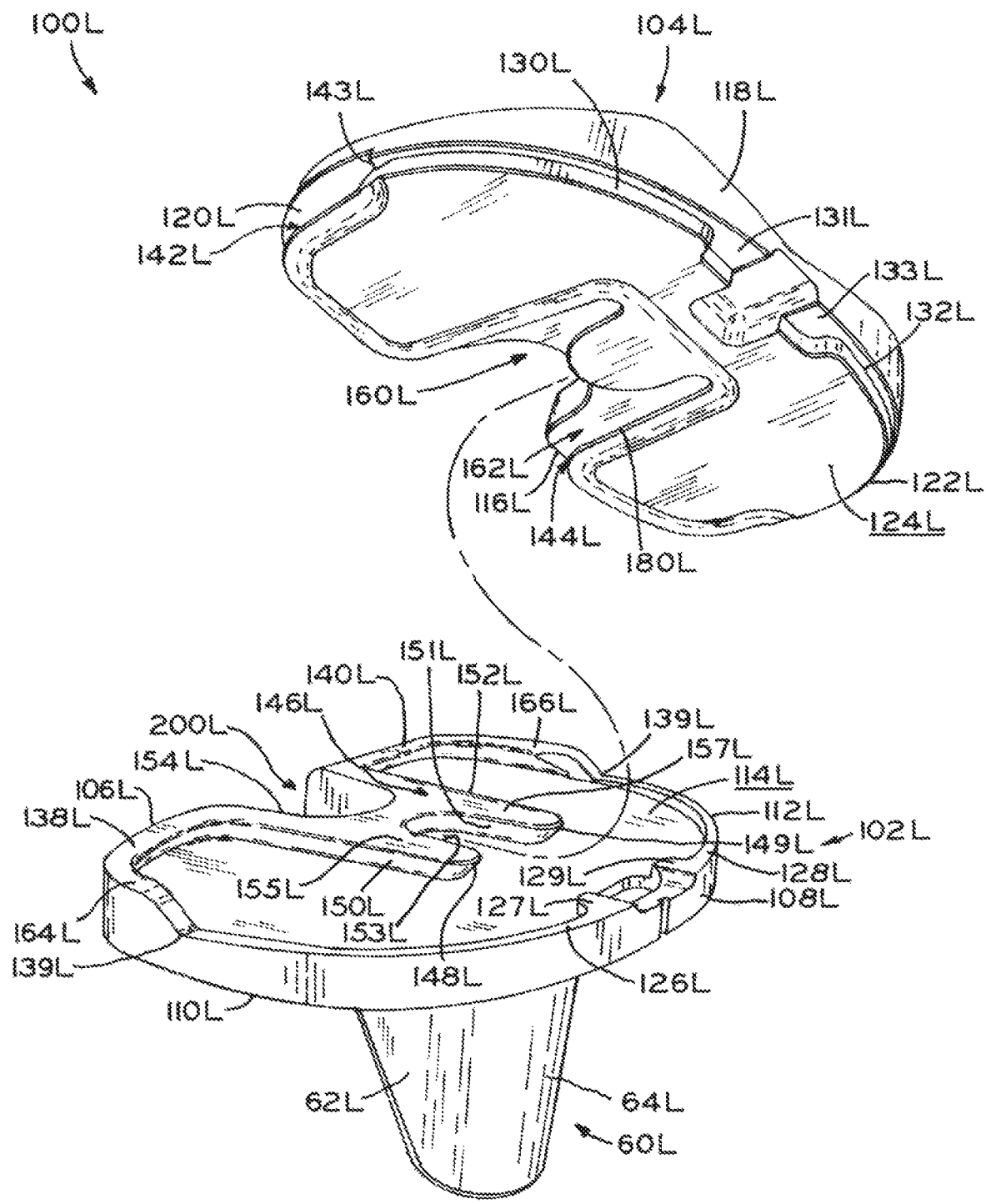
FIG. 58 is an exploded anterior perspective view of a tibial prosthesis made in accordance with an exemplary twelfth embodiment of the present invention, including a bearing component and a tibial tray.

In the context of a prosthesis, such as tibial tray 102L, described below, "home axis" M refers to an axis oriented with respect to tibial fray 102L such that the component home axis M of tibial tray 102L is aligned with home axis M of tibia T after implantation of tibial tray 102L in a proper rotational and spatial orientation (as shown in FIG. 57). In the illustrative embodiments shown, for example, in FIGS. 57-62 and in detail described below, home axis M bisects PCL cutout 200L at the posterior edge 154L of tibial tray 102L (FIG. 61), and bisects anterior edge 108L of tibial tray 102L. It is contemplated that home axis M may be oriented to other baseplate features, it being understood home axis M of tibial tray 102L is positioned such that that proper alignment and orientation of tibial tray 102L upon tibia T (FIG. 57) positions the home axis M of tibial tray 102L coincident with home axis M of tibia T.

Certain embodiments of this disclosure include a posterior-medial edge of both a tibial tray and a bearing component that is symmetric with respect to the posterior-lateral edge of the tibial tray and bearing component. However, other embodiments include tibial tray and bearing components that have asymmetric medial and lateral compartments. Exemplary asymmetric tibial prostheses are disclosed in U.S. patent application Ser. Nos. 13/189,336, 13/189,338 and 13/189,339, each entitled ASYMMETRIC TIBIAL COMPONENTS FOR A KNEE PROSTHESIS and filed on even date herewith, the entire disclosures of which are hereby expressly incorporated herein by reference. Any of the embodiments of the present disclosure may include posterior-medial and posteriorlateral edges that are either symmetric or asymmetric.

To implant a tibial prosthesis including a tibial tray and a bearing component, the proximal portion of a patent's tibia is resected to provide a substantially flat surface for receipt of the tibial tray. Once the proximal tibia, is resected, the tibial tray may be positioned on the proximal tibia in a location and orientation that maximizes coverage of the resected tibial surface while avoiding or minimizing overhang beyond the resected surface. With the tibial baseplate secured, the bearing component may be inserted onto the tibial, tray via an incision made to access a knee during surgery. Minimally invasive surgical techniques and associated implant components may be used.

The knee prostheses of the present disclosure may include tibial trays having canted bosses or bosses that are not canted with respect to the reference axis (described above). Knee prostheses including tibial trays having canted bosses and associated methods of insertion within the present disclosure desirably allow for implantation of a bearing component for securement atop an implanted tibial tray along an anterior-medial insertion path; advantageously, such implantation avoids the extensor mechanism of the knee.

Figure 56:
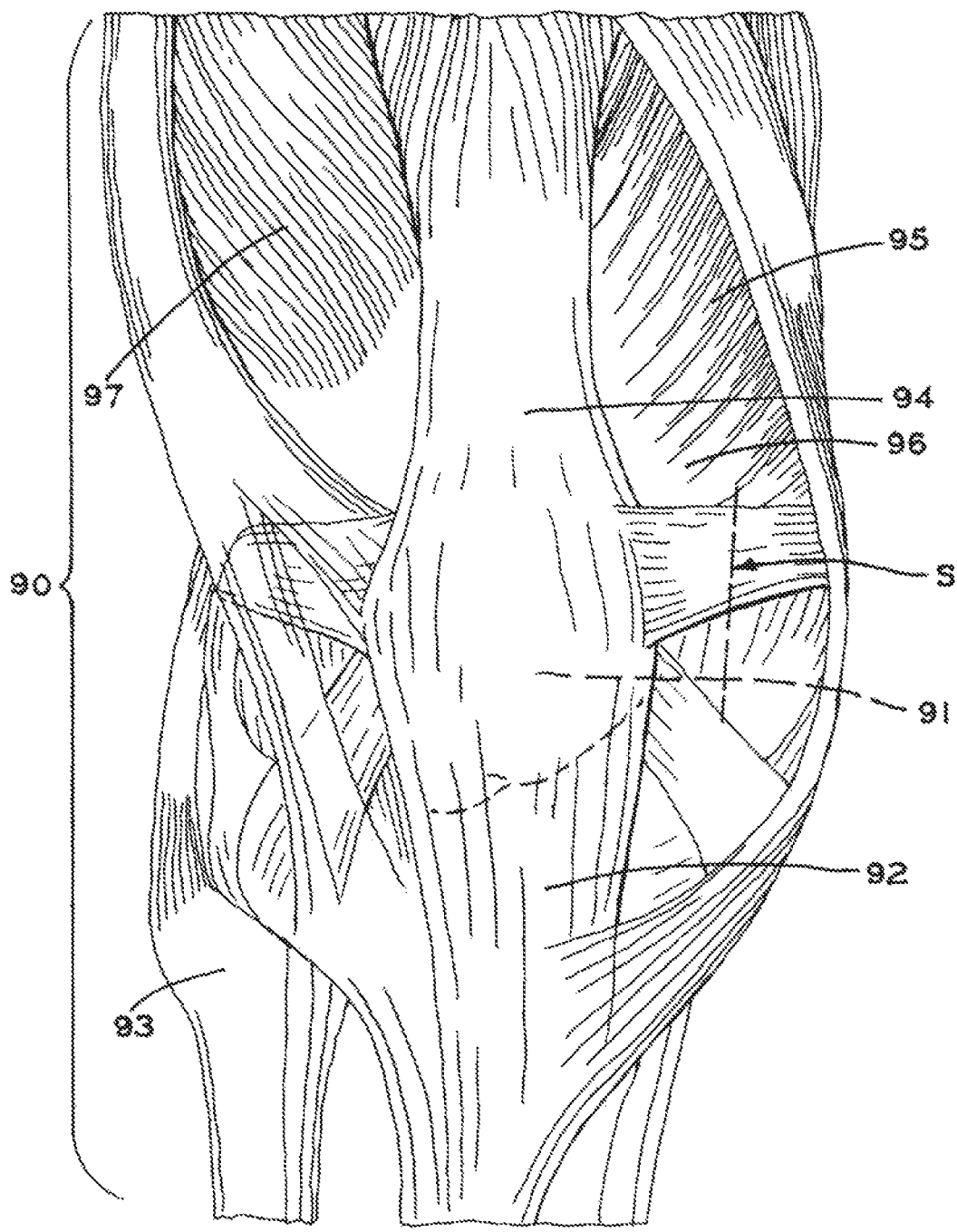
FIG. 56 is an anatomical view of a right knee showing the extensor mechanism of the knee and an exemplary incision made to access the knee.

FIG. 56 shows an anatomical view of the extensor mechanism of the knee, which is a complex interaction of knee muscles, ligaments, and tendons that stabilize the patellofemoral joint made up of the patella 91 and distal end of the femur (not shown). Fibula 93 is located at a lateral side of the tibia (not shown). Included among the extensor mechanism muscles are the front thigh muscles of the knee, or quadriceps, that insert into patella 91 and act to extend the knee and control, side-to-side movement of patella 91. The quadriceps include the rectus femoris (not shown), quadriceps tendon 94, and vastus medialis 95. Vastus medialis 95 includes vastus medialis obliquus 96 and vastus lateralis 97. FIG. 56 further shows an example of incision S made to access the knee, though other types and positions of incisions are contemplated within the scope of this disclosure for the purpose of accessing the knee and implanting a tibial prosthesis.

Alternatively, the exemplary first through fifth and tenth through twelfth embodiments of the present disclosure include tibial trays having bosses that are not canted with respect to an axis parallel to the sagittal plane that centrally divides a body into left and right halves. In particular, the first through fifth exemplary embodiments, as described in greater detail below, provide for bearing components positioned atop respective tibial trays along a generally anterior-posterior axis that is parallel to the sagittal plane. However, the sixth through ninth exemplary embodiments of this present disclosure include tibial trays having bosses that are canted with respect to the generally anterior-posterior axis and bearing components positioned atop the respective tibial trays.

All of the disclosed embodiments include Posterior Cruciate Ligament ("PCL") cutouts that are oriented at a posterior edge of both the bearing components and the tibial trays of the present disclosure and have an axis that is aligned with a reference axis. However, it is contemplated that a prosthesis in accordance with the present disclosure may be made for a design in which the posterior cruciate ligament is resected during surgery, such as "posterior stabilized" (PS) or "ultra congruent" (UC) designs. The PS and UC designs may exclude the PCL cutout in the bearing component 14, thereby obviating the need for any corresponding PCL cutout in the tibial baseplate. Thus, continuous material may instead occupy the area of the PCL cutouts.

The PCL cutouts of the first through ninth exemplary embodiments have axes aligned with a generally anterior-posterior axis parallel to the sagittal plane. Further, bosses of tibial trays extending from the PCL cutouts are canted or not canted with respect to the generally anterior-posterior axis. However, as another example, the tenth, through twelfth embodiments, as described in greater detail below, provide for bearing components positioned atop respective tibial trays including PCL cutouts having axes aligned with anatomic home axis M. The tibial trays further have bosses that are not canted with respect to anatomic home axis M. During implantation, the bearing component is urged along this "home axis" for seating upon the tibial tray.

The boss of the tibial tray may optionally be elongated towards the anterior of the tibial tray. Additionally or alternatively, the boss may be elongated in directions both towards a medial, edge and a lateral edge of the tibial tray. Further, the bearing component of the above embodiments may include anterior wedges, or tabs, that project from an anterior edge of the bearing component. The anterior wedges of the bearing component, and additionally or alternatively, the elongated boss of the tibial tray may allow for sufficient resistance to lift-off of the bearing component while eliminating the need for a secondary locking mechanism between the bearing component and the tibial tray.

For purposes of this disclosure, any of the disclosed embodiments may include bearing components positioned atop respective tibial trays along either a generally anterior-posterior axis or anatomic home axis M. Additionally, any of the disclosed embodiments may have bosses on the tibial trays that are canted or non-canted with respect to a general anterior-posterior axis or anatomic home axis M, and bosses that are elongated in any direction. Further, any of the bosses of the tibial trays of the embodiments within this present disclosure may be offset or not offset from a centralized axis between an anterior edge and a posterior edge of the tibial tray. Moreover, any of the disclosed embodiments within this present disclosure may include anteriorly positioned wedges projecting torn an anterior edge of a respective bearing component to allow for additional locking securement of the bearing component atop the tibial tray.

The first through ninth embodiments further include symmetric posterior edges adjacent to a PCL cutout in both a tibial tray and respective bearing component, while the tenth through twelfth embodiments disclose an asymmetry of the medial posterior edge and the lateral posterior edge of the respective tibial tray and bearing components. The disclosed symmetry or asymmetry of the posterior edges adjacent the PCL cutout however, may be included in any of the embodiments of the present disclosure.

The embodiments of this present disclosure farther provide for peripheral rails along the periphery of the respective tibial trays that are undercut, for example, through posterior edges of the tibial tray, with a 45° undercut tool, though alternative tooling may be used such as a 60° undercut tool to allow for increased height of the rails. The above mentioned undercut tools may also provide undercuts for the dovetail bosses or other peripherally positioned rails of the tibial trays in any of the disclosed embodiments. Undercuts are inclusive of dovetails, but also include any structure or profile on a first part which, when slidingly mated with a corresponding structure or profile on a second part, serves to prevent the first part from moving relative to the second part along a direction normal to the sliding direction. In the context of knee prostheses, undercuts assist with preventing rotational micromotion of a bearing component that is seated atop a respective tibial tray and with preventing axial liftoff of the bearing component superiorly.

Alternatively, or additionally, a peripheral rail may include posterior, anterior, medial, and lateral edges having a containment rail that does not include an undercut feature but rather has a substantially straight edge projecting proximally from a support surface of the tibial tray. Such containment rails advantageously resist rotation of the bearing component atop the tibial tray. The peripheral rails may additionally be sloped and slightly thicker from anterior to posterior ends. Any of the embodiments of the present disclosure may lack or, alternatively, utilize a peripheral rail having any or all of posterior, anterior, medial and lateral edges that may either be undercut or in the form of a containment rail.

Figure 1:
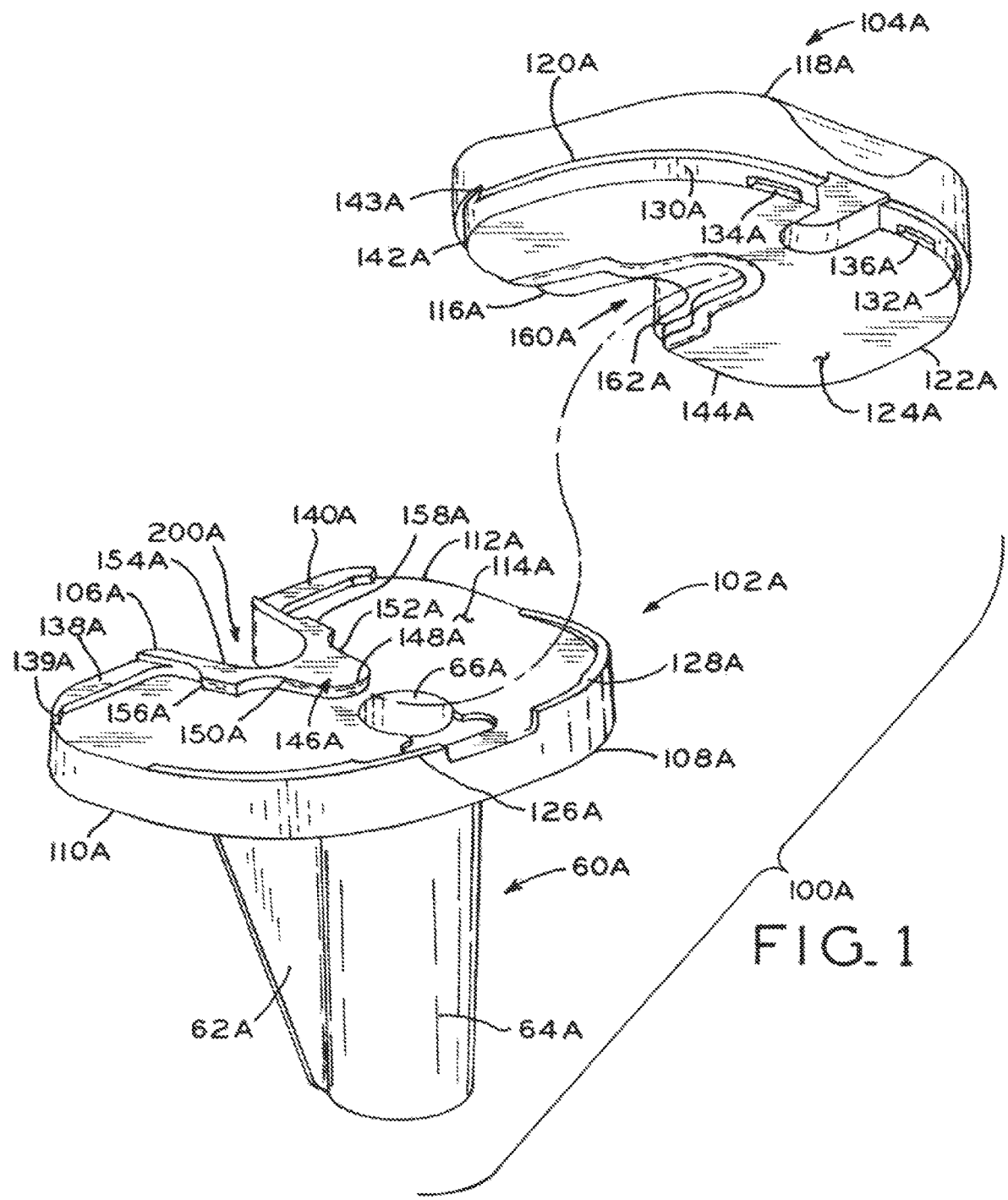
FIG. 1 is an exploded anterior perspective view of a tibial prosthesis made in accordance with an exemplary first embodiment of the present invention, including a bearing component and a tibial tray.
Figure 2:
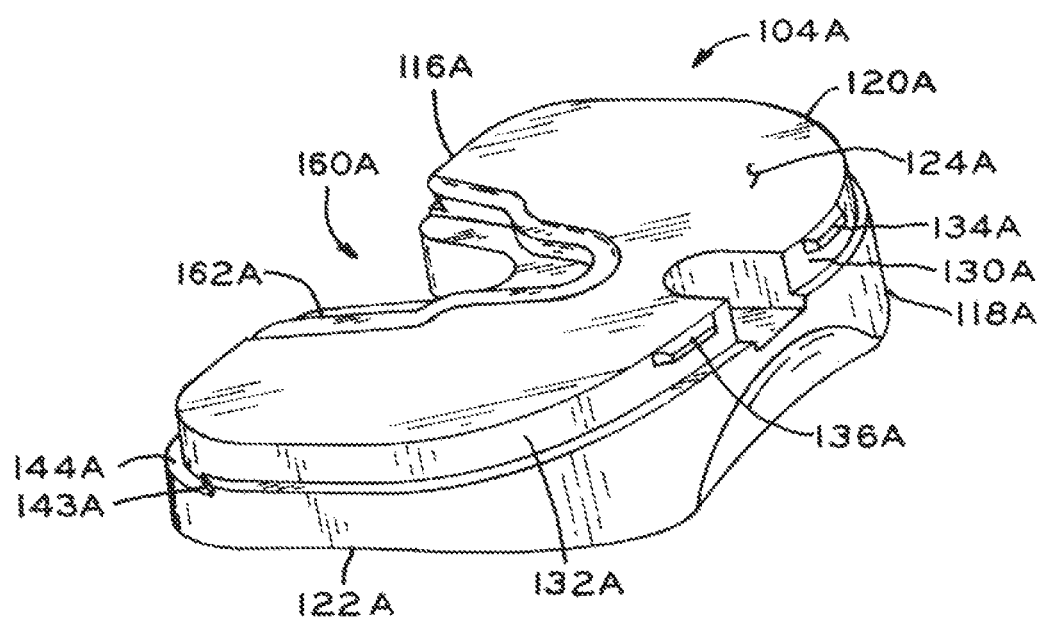
FIG. 2 is a lateral perspective view of the hearing component of the first embodiment from a distal to proximal aspect.
Figure 3:
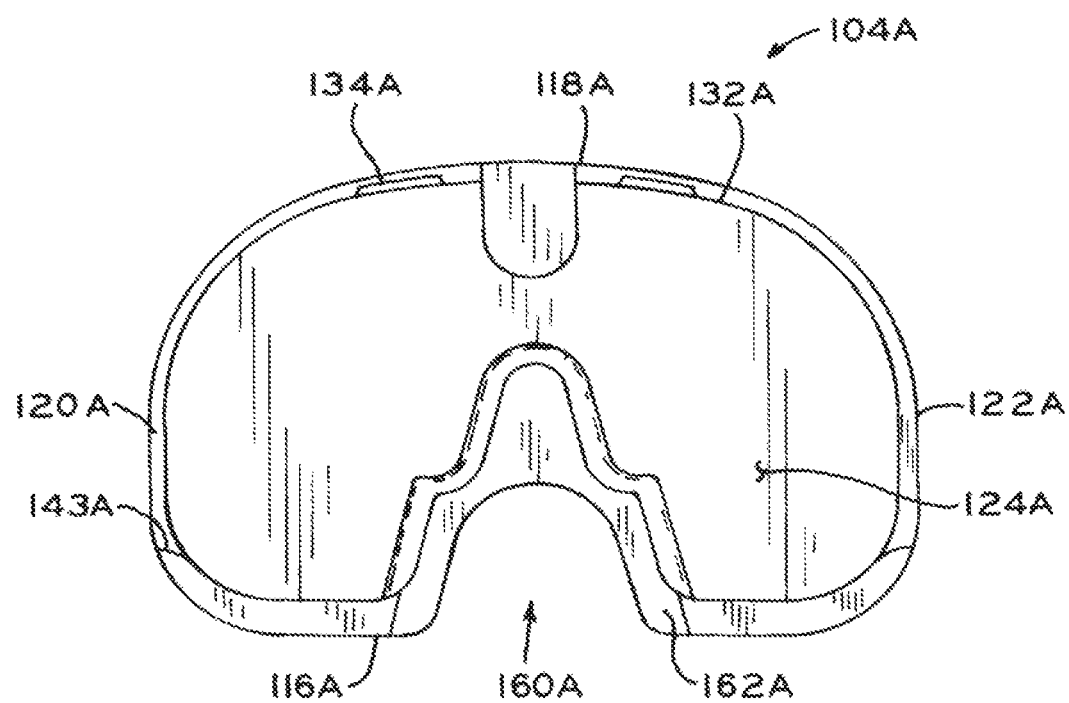
FIG. 3 is a distal plan view of the bearing component of the first embodiment.
Figure 6:
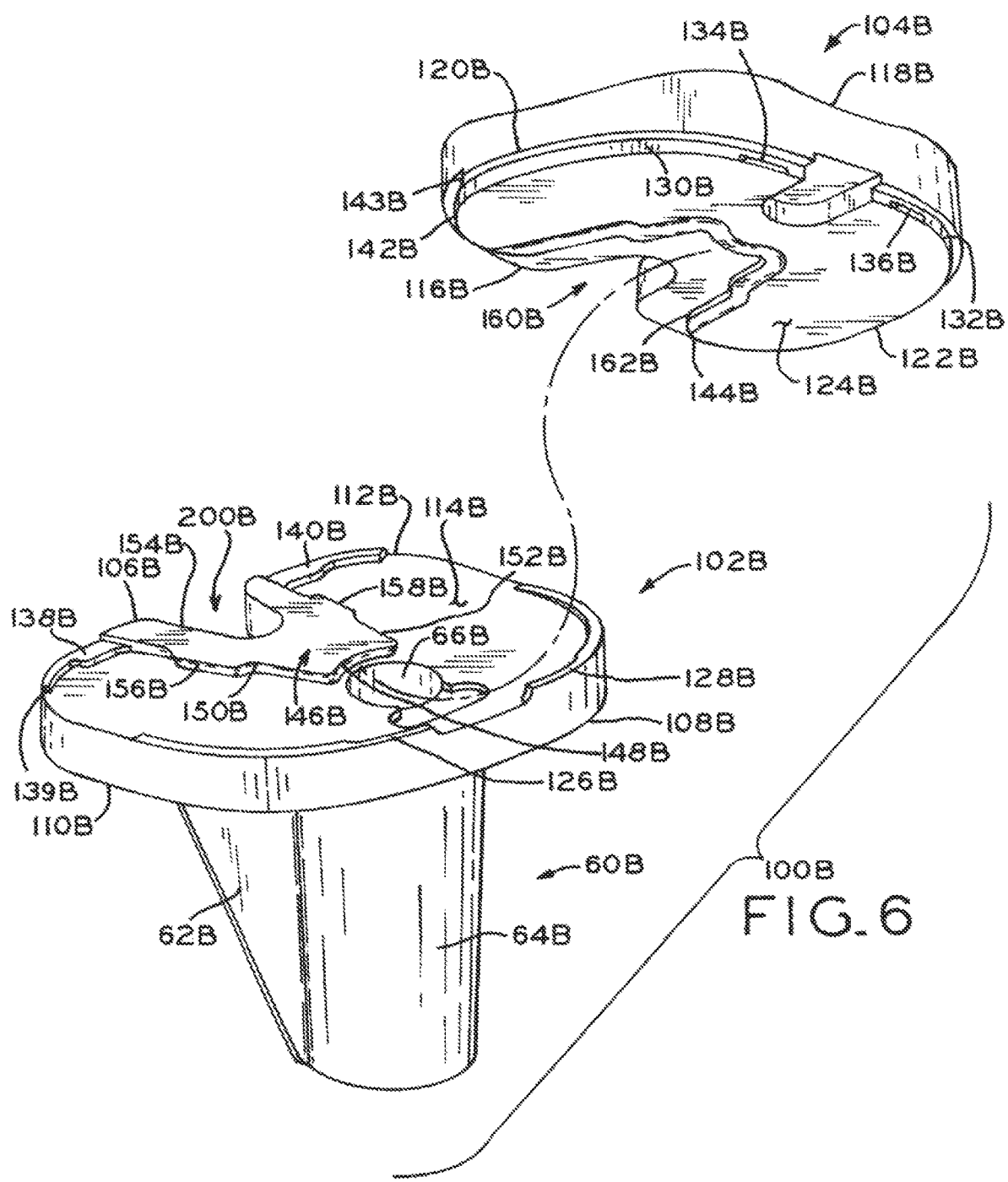
FIG. 6 is an exploded anterior perspective view of a tibial prosthesis made in accordance with an exemplary second embodiment of the present invention, including a bearing component and a tibial tray.
Figure 7:
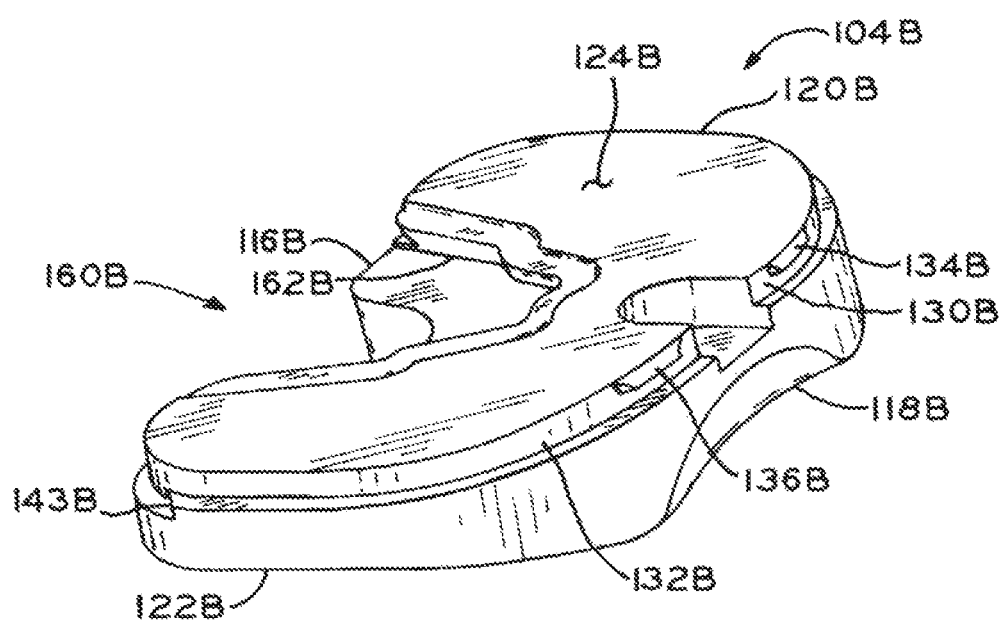
FIG. 7 is a lateral perspective view of the bearing component of the second embodiment from a distal to proximal aspect.
Figure 8:
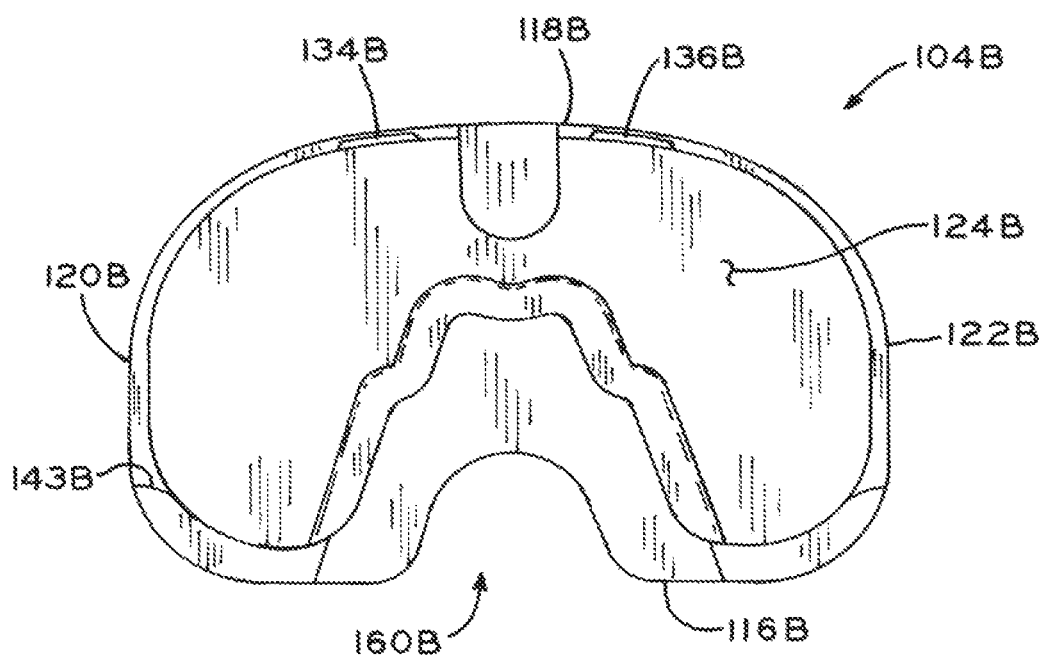
FIG. 8 is a distal plan view of the bearing component of the second embodiment.
Figure 9:
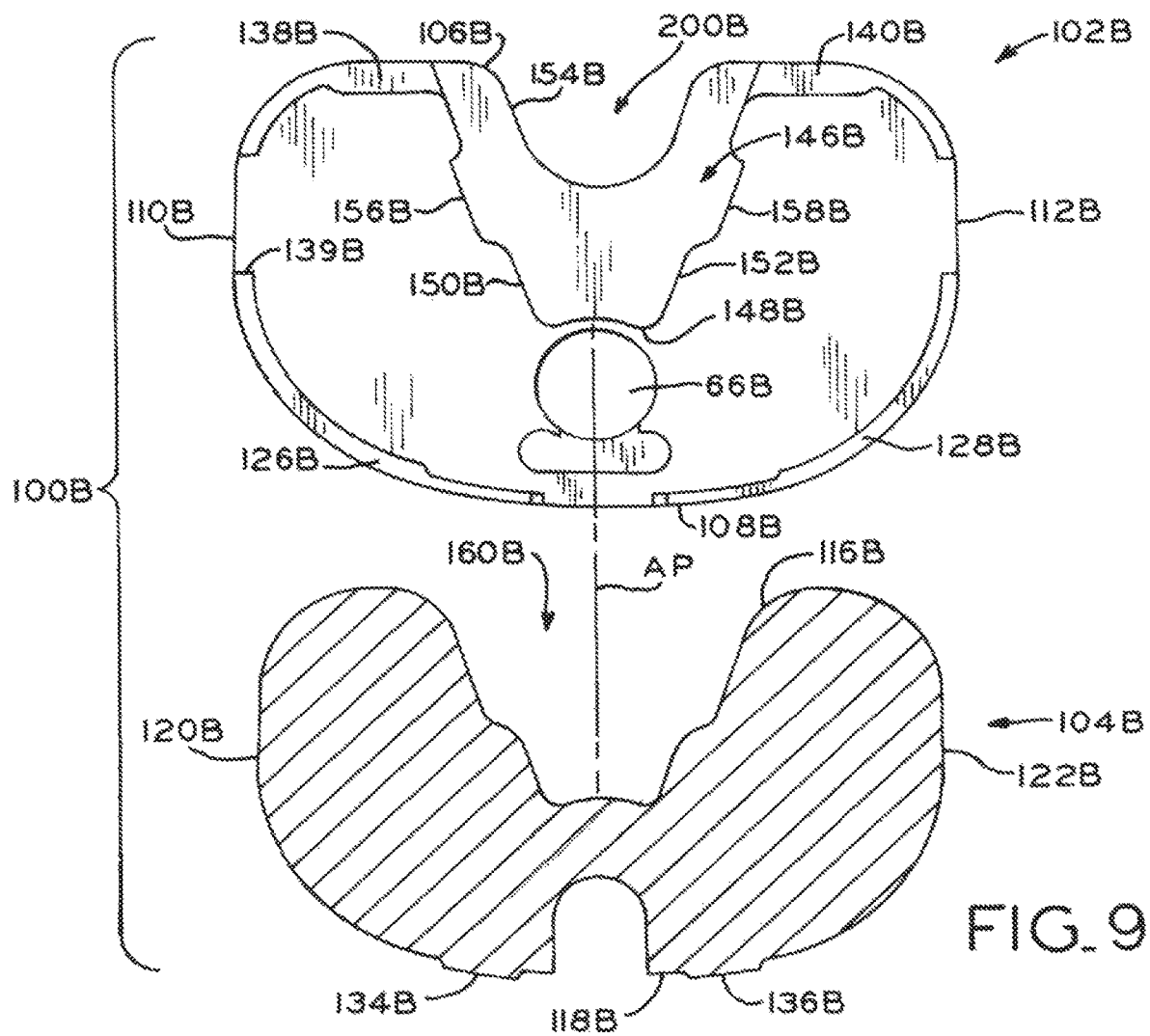
FIG. 9 is a proximal plan, partial sectional view of the tibial prosthesis showing a straight insertion, along a general anterior-posterior axis parallel to a sagittal plane, of the bearing component onto the tibial tray of the second embodiment.

The disclosed embodiments include a tibial tray having a tibial stem including a stem fin and a stem shaft distally extending from an optional aperture of each tibial tray and projecting into the tibia. For example, as shown in FIG. 1 of an exemplary first embodiment, tibial stem 60A includes stem fin 62A and stem shaft 64A distally extending from optional aperture 66A of each tibial tray and projecting into the tibia (not shown). Alternatively, a tibial tray may not include astern shaft.

Turning now to the drawings, reference numbers for the stem, stem fin, stem shaft, and aperture elements where illustrated utilize the same numerical reference number combined with different letters to distinguish the exemplary embodiment (i.e., stem 60A, 60B, 60C, etc. correspond to the first, second, and third exemplary embodiments, etc.). For the purposes of this disclosure, a reference numeral followed by A-L corresponds to a similar feature between the exemplary first through twelfth embodiments, respectively. Structures of one embodiment are similar to structures of another embodiment, with reference numbers in respective Figures referring to analogous structures shown in analogous figures except where described otherwise.

FIG. 1 illustrates a first embodiment, for example, with tibial prosthesis 100A including tibial tray 102A and bearing component 104A. As the second through eleventh embodiments similarly include a tibial prosthesis including a tibial tray and bearing components, these features are numbered in a respectively similarly increasing alpha-numeric scheme as described above (i.e., the second embodiment includes tibial prosthesis 100B and the twelfth embodiment includes tibial prosthesis 100L).

Other common elements between the twelve described exemplary embodiments follow a similar reference number labeling scheme. For example, the first embodiment, as illustrated in FIG. 1, includes tibial, tray 102A having posterior edge 106A, anterior edge 108A, medial edge 110A, lateral edge 112A, and a support such as support surface 114A. Support surface 114A may be capable of supporting bearing component 104A and may directly or indirectly communicate with bearing component 104A. When the communication is indirect, other components may be positioned between bearing component 104A and the support of tibial tray 102A. Further, bearing component 104A includes a peripheral wall defining posterior edge 116A, anterior edge 118A, medial edge 120A, lateral edge 122A, and distal surface 124A. Tibial trays and bearing components of the other exemplary left knee embodiments include similarly labeled elements, where present, per the exemplary scheme outlined above. Right knee applications are illustrated in FIGS. 46-62 and differ from the left knee embodiments by having an opposite lateral and medial numbering scheme. For example, tibial trays 102J and 102K each have medial edges 112J and 112K, respectively, and lateral edges 110J and 110K, respectively. Further, bearing components 104J and 104K each have medial, edges 122J and 122K, respectively, and lateral edges 120J and 120K, respectively.

While the exemplary embodiments of the present disclosure are shown and described herein with specific reference to a left knee application, unless stated otherwise, the associated tibial prostheses may also be configured for use in a right knee application and vice-versa. Right and left knee configurations are minor images of one another about a sagittal plane, and it is contemplated that all aspects of the prostheses described herein are equally applicable to a left- or right-knee configuration. Moreover, it will be appreciated that the principles of the present disclosure are also applicable to other mammalian, joints, such as the human hip, shoulder, elbow, ankle, and the like.

Any tibial prosthesis of the present disclosure may include a bearing component having at least one concave articulating surface configured for articulation against opposing condyles of a femur or femoral prosthesis (not shown). Further, any of the embodiments described within the present disclosure may include an optional tibial eminence E (FIG. 57) protruding from a proximal surface of the bearing component and positioned between a pair of opposed, articulating surfaces of the bearing component.

FIGS. 1-5 illustrate an exemplary first embodiment. As shown in FIGS. 1, 4, and 5, tibial tray 102A includes a pair of anterior rails 126A and 128A, with anterior rail 126A positioned along medial edge 110A and anterior rail 128A positioned along lateral edge 112A. Lateral anterior rail 128A and medial anterior rail 126A both include anterior portions that are thinner than portions extending towards lateral edge 112A and medial edge 110A, respectively. When bearing component 104A is affixed to tibial tray 102A, the pair of anterior rails 126A and 128A are respectively received within a pair of anterior rail recesses 130A and 132A (FIGS. 1 and 2) formed within anterior edge 118A of bearing component 104A. Further, the pair of anterior rails 126A and 128A are recessed at their interior faces to create thinner portions sized to receive a respective pair of anterior wedges 134A and 136A (FIGS. 1, 2, and 3) of bearing component 104A.

Advantageously, the reception of anterior wedges 134A and 136A within the pair of anterior rails 126A and 128A, respectively, allows for a locking mechanism sufficient to resist a force attempting to lift bearing component 104A off from tibial tray 102A. Further, the reception of anterior rails 126A and 128A into anterior rail recesses 130A and 132A, respectively fill any gaps between the walls forming each of the respective anterior rails and anterior rail recesses and assist to prevent anterior movement of bearing component 104A once it is seated atop tibial tray 102A in a final locked position (FIG. 5).

As illustrated in FIGS. 1, 4, and 5, tibial tray 102A further includes a pair of posterior rails 138A and 140A. Rails 138A and 140A are received into posterior rail recesses 142A and 144A formed in posterior edge 116A of bearing component 104A. The reception of posterior rails 138A and 140A into posterior rail recesses 142A and 144A fill any gaps between the walls forming each of the respective posterior rails and posterior rail recesses and assist to prevent posterior movement of hearing component 104A once it is seated atop tibial tray 102A in a final locked position (FIG. 5). The posterior rail undercuts further assist with prevention of posterior lift-off of bearing component 104A from tibial tray 102A.

Referring back to FIG. 1, tibial tray 102A additionally includes boss 146A having anterior end 148A, medial side 150A, lateral side 152A, and posterior end 154A. Anterior end 148A, medial side 150A, and lateral side 152A form a U-shape with anterior end 148A of the U-shape positioned posteriorly of aperture 66A. Medial side 150A and lateral side 152A further include winged portions 156A and 158A, respectively. Bearing component 104A includes a corresponding notch 160A sized for receipt of boss 146A. Notch 160A has recessed indent 162A sized for receipt of the walls forming anterior end 148A, medial side 150A, and lateral side 152A of boss 146A. The walls may be undercut or, alternatively, may form a substantially straight edge projecting superiorly from support surface 114A of tibial tray 102A. Posterior end 154A of boss 146A forms PCL cutout 200A of tibial tray 102A.

The PCL cutout is positioned along a general anterior-posterior axis parallel to the sagittal plane, such as axis AP in FIG. 4. Boss 146A defines a central longitudinal axis that extends along axis AP such that boss 146A is not canted, or angled, with respect to the sagittal plane.

The reception of the walls forming anterior edge 148A, medial edge 150A, and lateral edge 152A of boss 146A within recessed indent 162A of notch 160A prevents posterior movement of bearing component 104A once it is seated atop tibial tray 102A in a final locked position. A boss of any shape and a correspondingly shaped notch that receives the boss are within the scope of this disclosure.

After tibial tray 102A is positioned within a knee through an incision made to provide access to the knee during surgery, bearing component 104A is inserted atop tibial tray 102A. Particularly, bearing component 104A is inserted through the incision to an initial reception position where a posterior end of notch 160A of bearing component 104A receives anterior end 148A of boss 146A of tibial tray 102A. Recessed indent 162A of notch 160A progressively receives the anterior, medial, and lateral walls forming boss 146A as bearing component 104A is inserted onto tibial tray 102A along axis AP. Medial and lateral sides 150A and 152A of boss 146A are positioned substantially parallel to the sagittal plane and axis AP.

Notch 160A is congruent with and slightly larger than boss 146A. Alternatively, at the location of wings 156A and 158A, notch 160A may be slightly undersized such that wings 156A and 158A cause deformation while securing bearing component 104A into place. Additionally, at the location of sides 150A and 152A, notch 160A may be slightly undersized such that sides 150A and 152A cause deformation while securing bearing component 104A in place. Such sizing of notch 160A, so that it is undersized in comparison with corresponding portions of boss 146A, may be present in any of the embodiments of this disclosure. Recessed indent 162A receives the above-mentioned walls of boss 146A.

Posterior rails 138A and 140A may have a stepped end, such as stepped end 139A, that is congruent with a stepped end, such as stepped end 143A, of posterior rails recesses 142A and 146A after bearing component 104A is assembled to tibial tray 102A. Further, as bearing component 104A is inserted over tibial tray 102A, bearing component 104A is inserted over anterior rails 126A and 128A of tibial tray 102A to engage in a final snap-fit connection with anterior rails 126A and 128A. Alternatively, anterior rails 126A and 128A may include a pair of extended perimeter ends from which a pair of rails project. Bearing component 104A may then include a pair of internal grooves having a thickness for receipt of the respective pair of rails such that the pair of rails have a corresponding thickness that substantially fill the grooves.

If boss 146A has walls which are undercut, the corresponding undercut walls of recessed indent 162A of notch 160A experience elastic deformation due to the insertion of bearing component 104A over anterior rails 126A and 128A of tibial tray 102A as distal surface 124A is separated from support surface 114A of tibial tray 102A. Similarly due to such insertion, if posterior rails 138A and 140A are undercut, posterior rail recesses 142A and 146A experience elastic deformation while receiving posterior rails 138A and 140A, respectively. Such elastic deformation is further described in U.S. patent application Ser. No. 13/189,324, entitled TIBIAL PROSTHESIS, incorporated by reference above.

For either an undercut boss rail or undercut peripheral rails, the deformation that occurs as described above cooperates with functional forces generated by the interaction of the mating portions of bearing component 104A and tibial tray 102A to increase resistance to movement of bearing component 102A along axis AP (FIG. 4) as such movement progresses. When the movement along axis AP has reached the end of its travel, recesses 130A, 132A of anterior edge 118A of bearing component 104A pass anterior rails 126A and 128A of tibial tray 102A. As recesses 130A, 132A fall into abutting engagement with anterior rails 126A, 128A, bearing component 104A snaps into a firm connection created by the operation of anterior edge 118A abutting an interior side of anterior rails 126A and 128A, and by anterior wedges 134A and 136A abutting anterior rails 126A and 128A, respectively. In this final seated position, bearing component 104A is locked to tibial tray 102A to form a fixed bearing prosthesis.

FIGS. 6-10 illustrate an exemplary second embodiment. The exemplary second embodiment includes a pair of anterior rails 126B and 128B (FIG. 6) that are received by respective anterior rail recesses 130B and 132B (FIG. 7) of bearing component 104B, and that receive anterior wedges 134B and 136B (FIG. 8) of bearing component 104B, similar to the manner described in the exemplary first embodiment. Further, the exemplary second embodiment includes posterior rails 138B and 140B, and posterior rail recesses 142B and 144B that receive posterior rails 138B and 140B, respectively, that are similar to those described above with respect to the first embodiment. Similarly, the walls forming boss 146B may be undercut or alternatively may form a substantially straight edge projecting superiorly from support surface 114A of tibial tray 102A.

Figure 10:
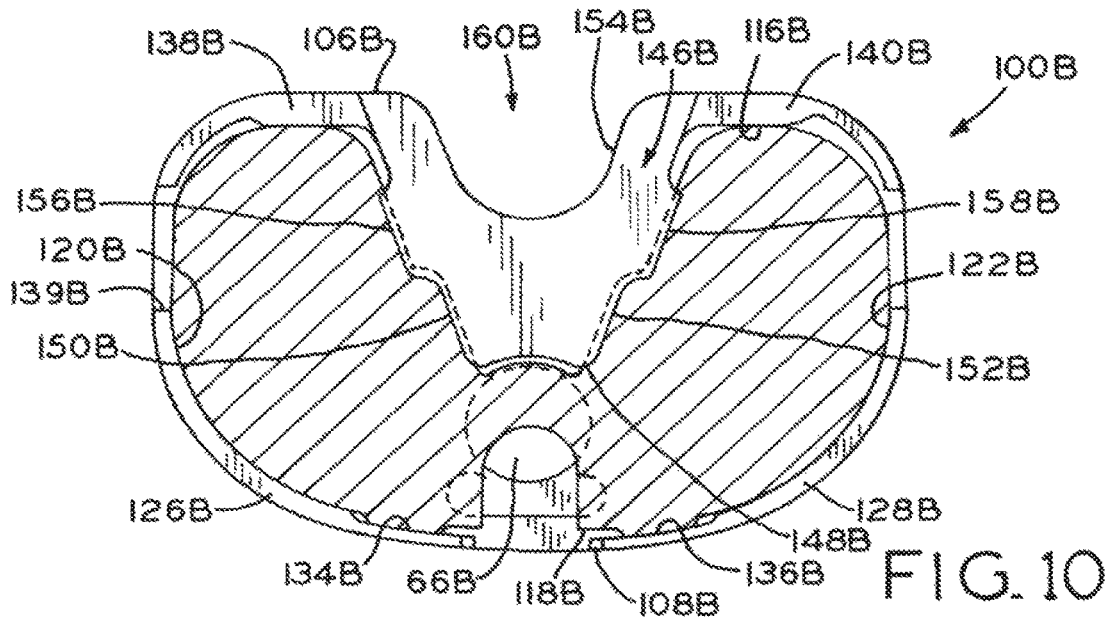
FIG. 10 is a proximal plan, partial sectional view of the tibial prosthesis of FIG. 9, with the bearing component fully seated on the tibial tray.

While boss 146B of tibial tray 102B is similarly received into corresponding notch 160B of bearing component 104B, anterior end 148B, medial side 150B and lateral side 152B of boss 146B form a shape different from that of the exemplary first embodiment. Boss 146B includes posterior end 154B forming a PCL cutout for tibial tray 102B, similar to boss 154A shown in FIG. 1. However, anterior end 148B, while still positioned posterior to aperture 66B, is slightly more elongated than in boss 146A of the first embodiment. Further, medial side 150B and lateral side 152B are elongated to provide boss 146B with a width sufficient to prevent or minimize rotational micromotion and lift-off of bearing component 104B atop tibial tray 102B in a final seated position (FIG. 10). The method of insertion of bearing component 104B atop tibial tray 102B along axis AP (FIG. 9) is otherwise similar to the method described above for the exemplary first embodiment.

Figure 11:
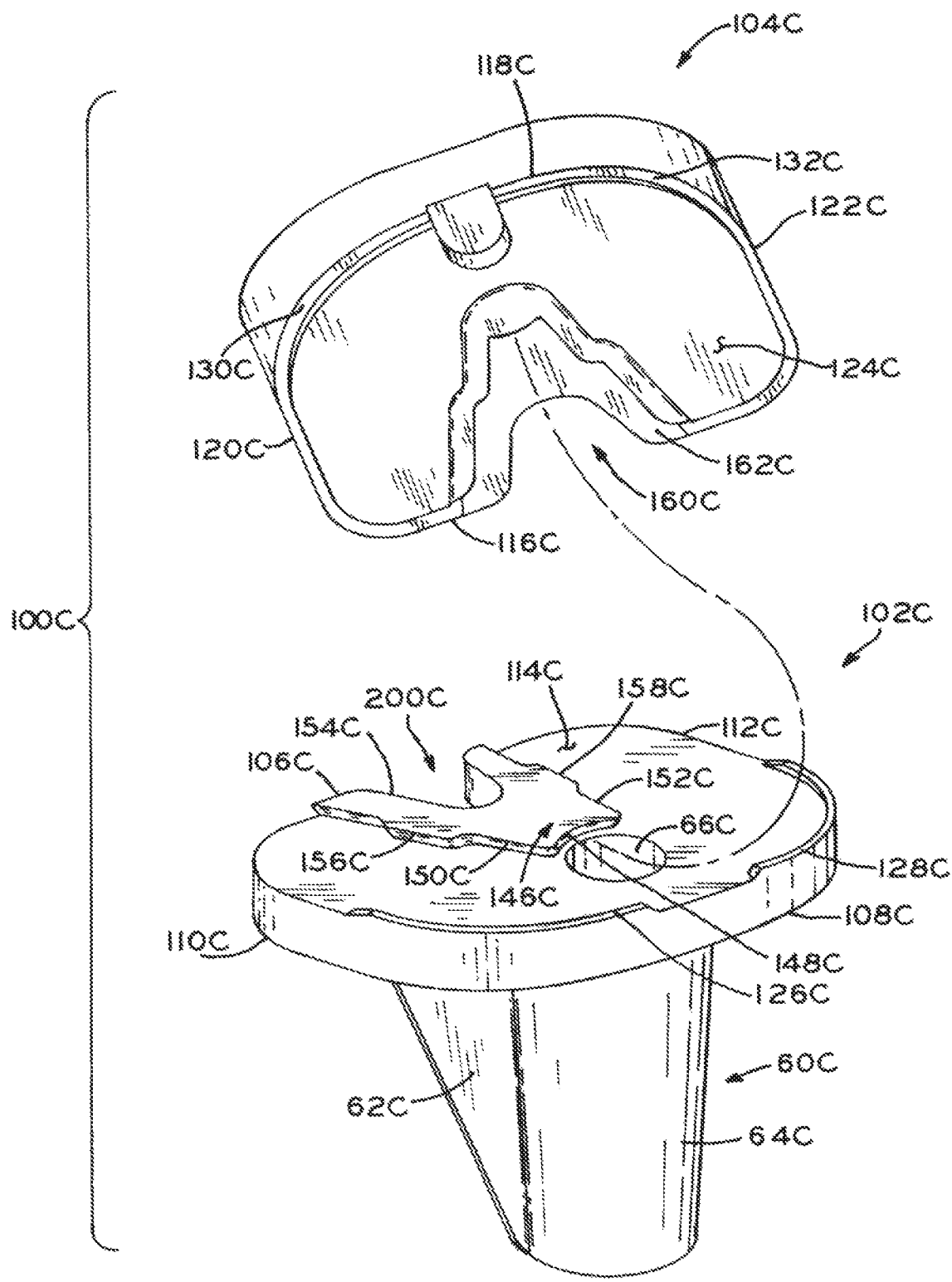
FIG. 11 is an exploded anterior perspective view of a tibial prosthesis made in accordance with an exemplary third embodiment of the present invention, including a bearing component and a tibial tray.
Figure 12:
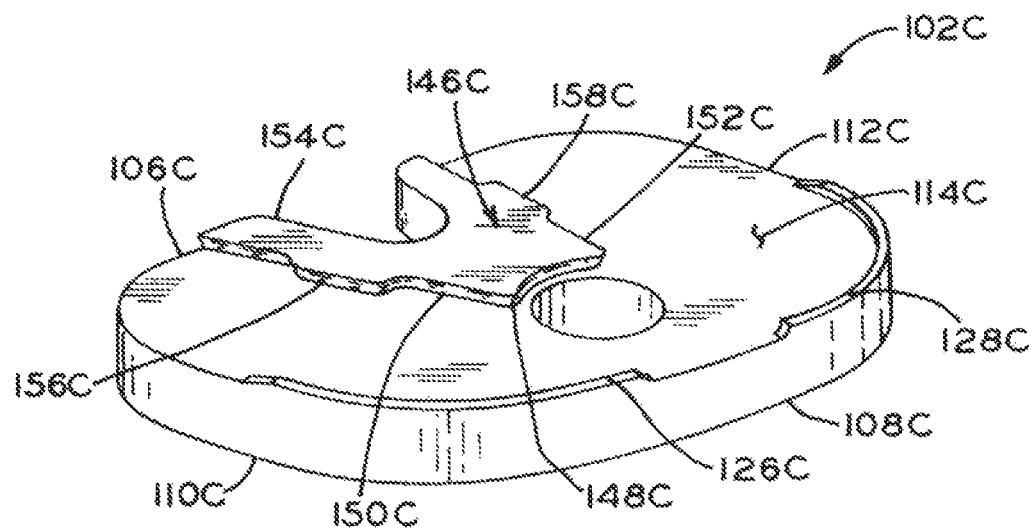
FIG. 12 is a anterior perspective view of the tibial tray of the third embodiment.
Figure 13:
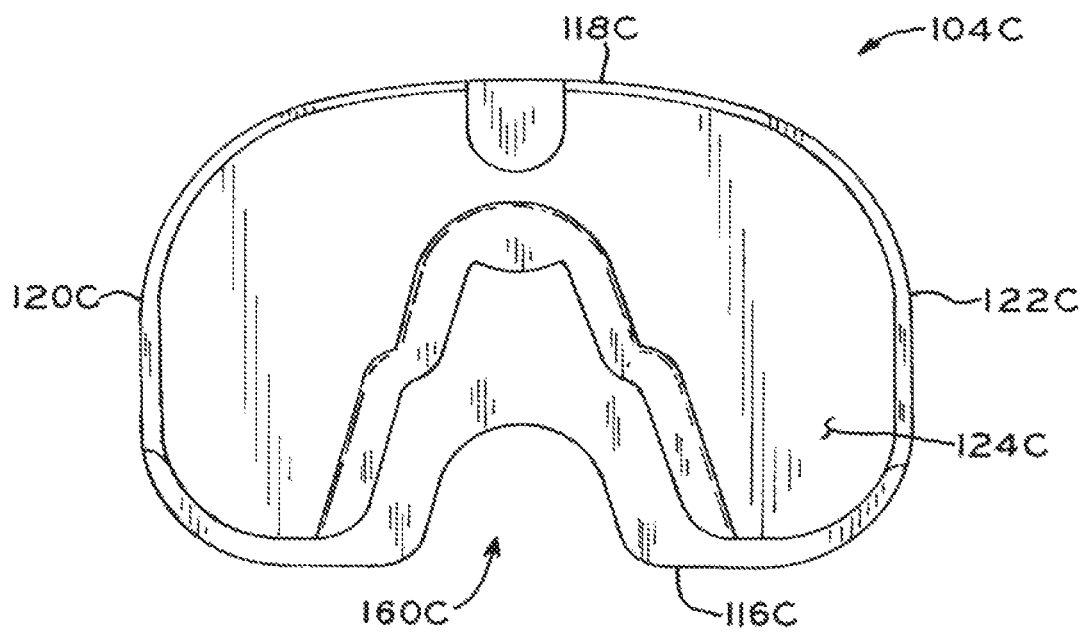
FIG. 13 is a distal plan view of the bearing component of the third embodiment.

FIGS. 11-15 illustrate an exemplary third embodiment. Referring to FIGS. 11 and 12, tibial tray 102C of the exemplary third embodiment is similar to tibial tray 102B of the exemplary second embodiment absent the inclusion of posterior rails on tibial tray 102C and corresponding posterior rail recesses on bearing component 104C. Further, bearing component 104C (FIGS. 11 and 13) does not include anterior wedges on anterior edge 118C and anterior rails 126C and 128C of tibial tray 102C has a substantially similar thickness through the length of the anterior rails. Additionally, the walls forming boss 146C are undercut and are received in an interference fit by corresponding walls of indented recess 162C such that any gaps between the walls forming the surfaces of boss 146C and notch 160C are filled.

The method of insertion of bearing component 104C atop tibial tray 102C along axis AP (FIG. 14) is otherwise similar to the method described above for the exemplary first embodiment. As illustrated in FIG. 15, when bearing component 104C is seated, atop 102C, anterior movement is prevented or minimized by the abutment of anterior face recesses 130C, 132C of anterior edge 118C on bearing component 104C with a posterior face of anterior rails 126C and 128C on tibial tray 102C.

Further, posterior movement is prevented or minimized by the abutment of a wall forming anterior end 148C of boss 146C with an anterior end of recessed indent 162C formed within notch 160C. Further, the elongated width of undercut medial side 150C and undercut lateral side 152C and the elongation of undercut anterior end 148C of boss 146C creates an elongated boss structure sufficient to overcome forces attempting to lift bearing component 104C off tibial tray 102C during natural joint articulation.

Figure 16:
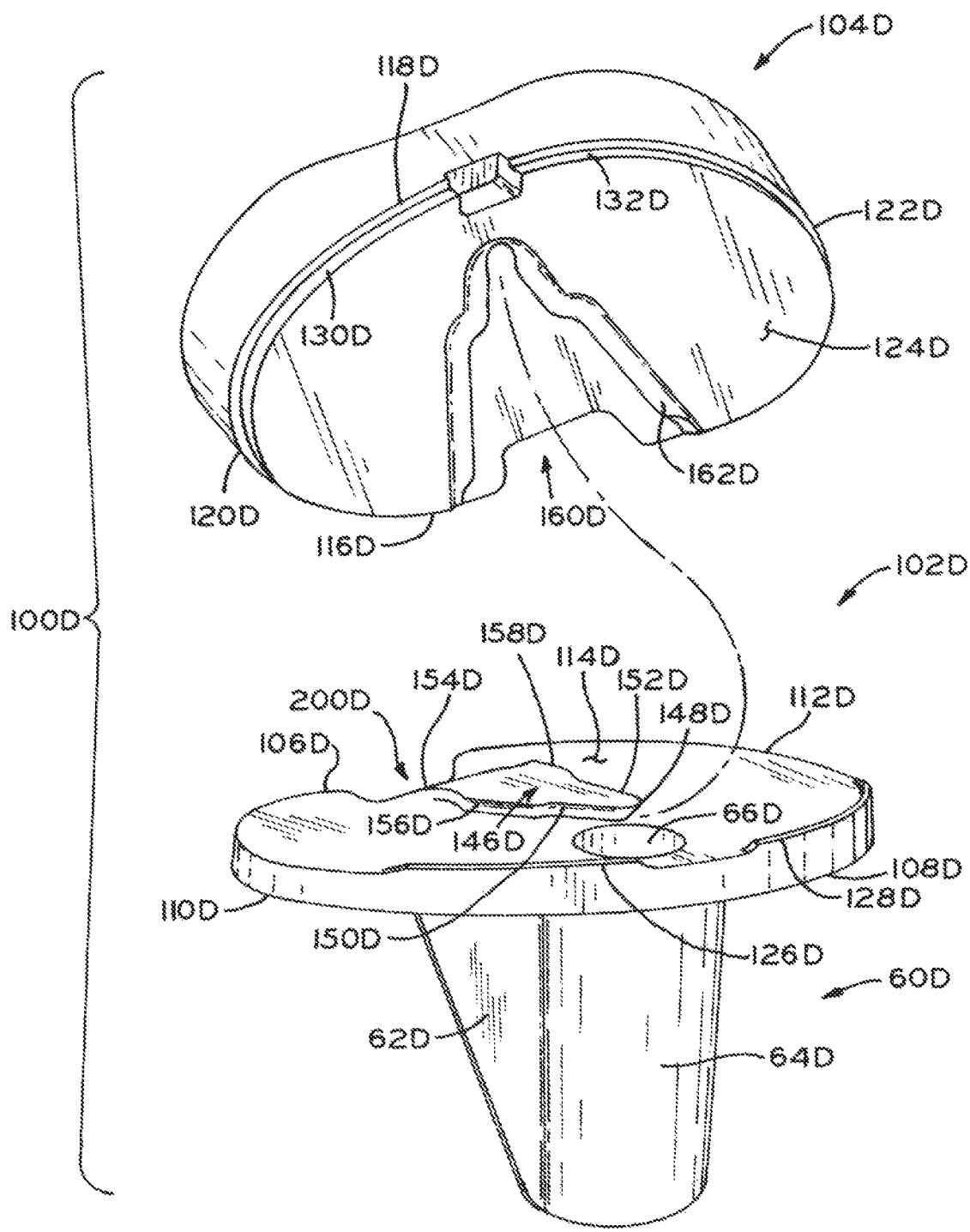
FIG. 16 is an exploded anterior perspective view of a tibial prosthesis made in accordance with an exemplary fourth embodiment of the present invention, including a bearing component and a tibial tray.
Figure 19:
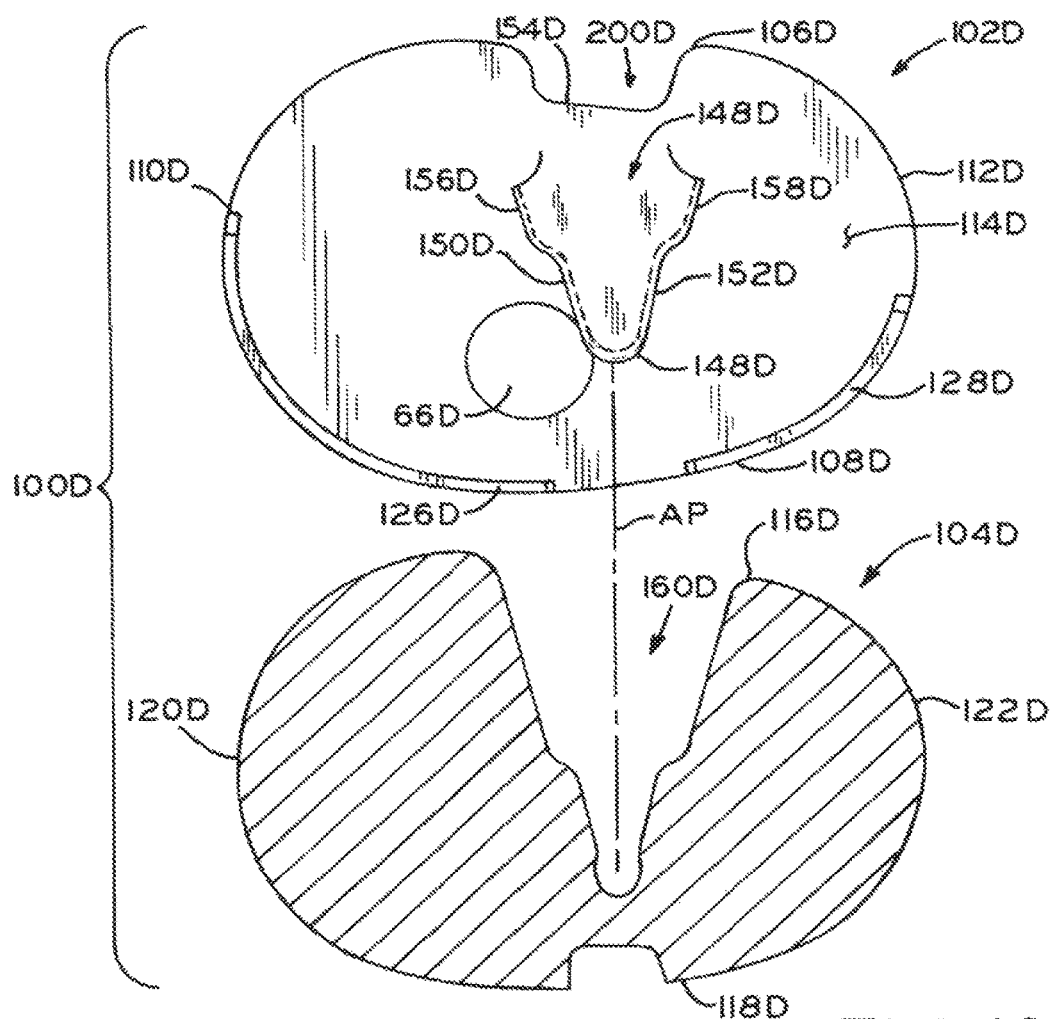
FIG. 19 is a proximal plan, partial sectional view of the tibial prosthesis showing a straight insertion, along a general anterior-posterior axis parallel to a sagittal plane, of the bearing component onto the tibial tray of the fourth embodiment.
Figure 20:
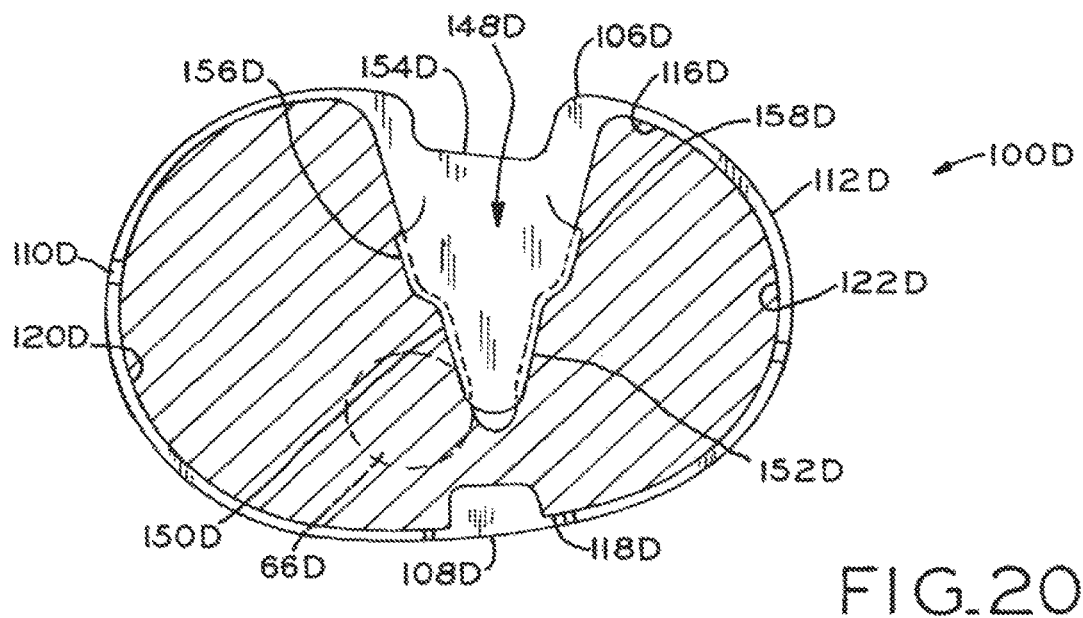
FIG. 20 is a proximal plan, partial sectional view of the tibial prosthesis of FIG. 19, with the bearing component fully seated on the tibial tray.
Figure 21:
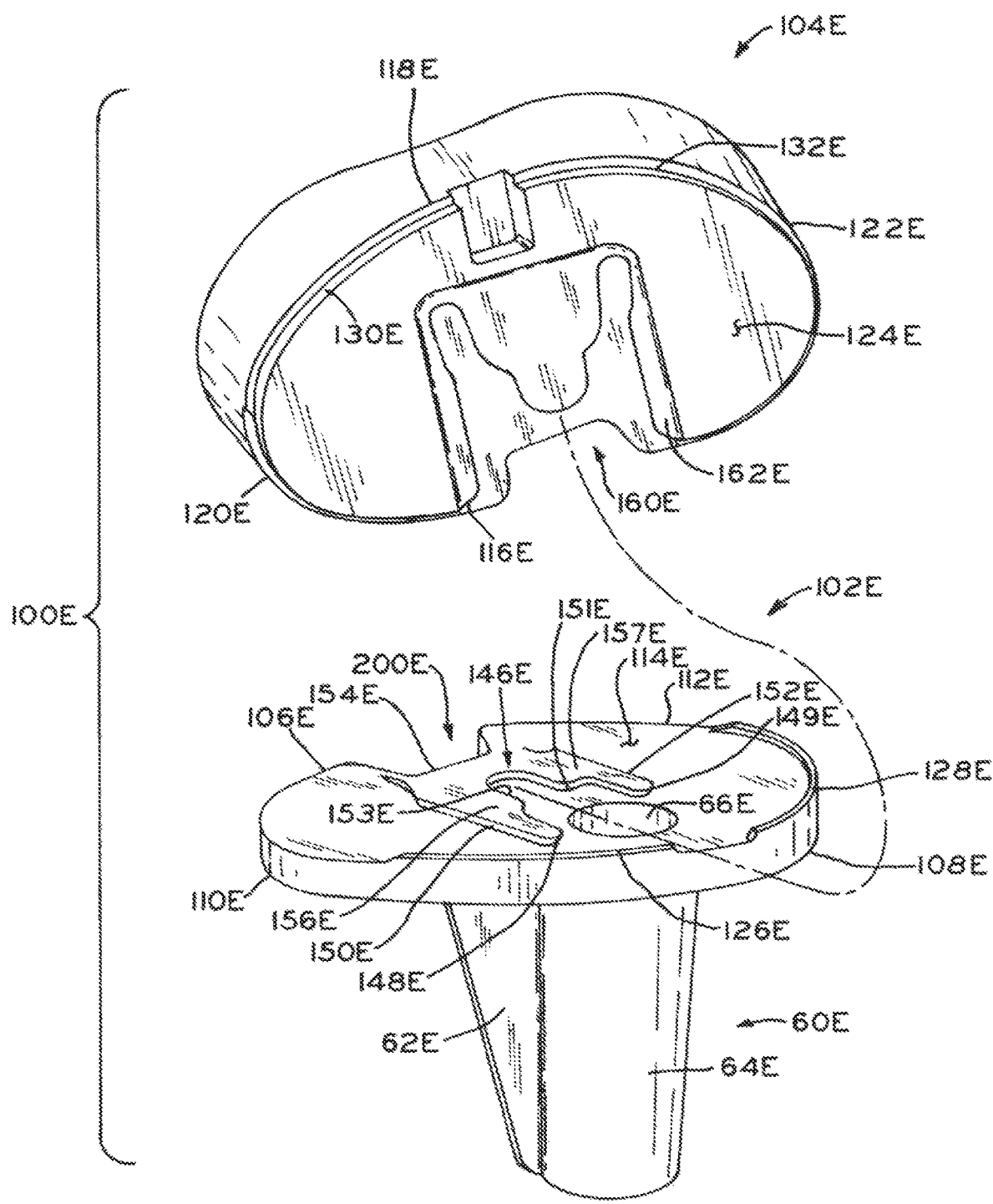
FIG. 21 is an exploded anterior perspective view of a tibial prosthesis made in accordance with an exemplary fifth embodiment of the present invention, including a bearing component and a tibial tray.
Figure 22:
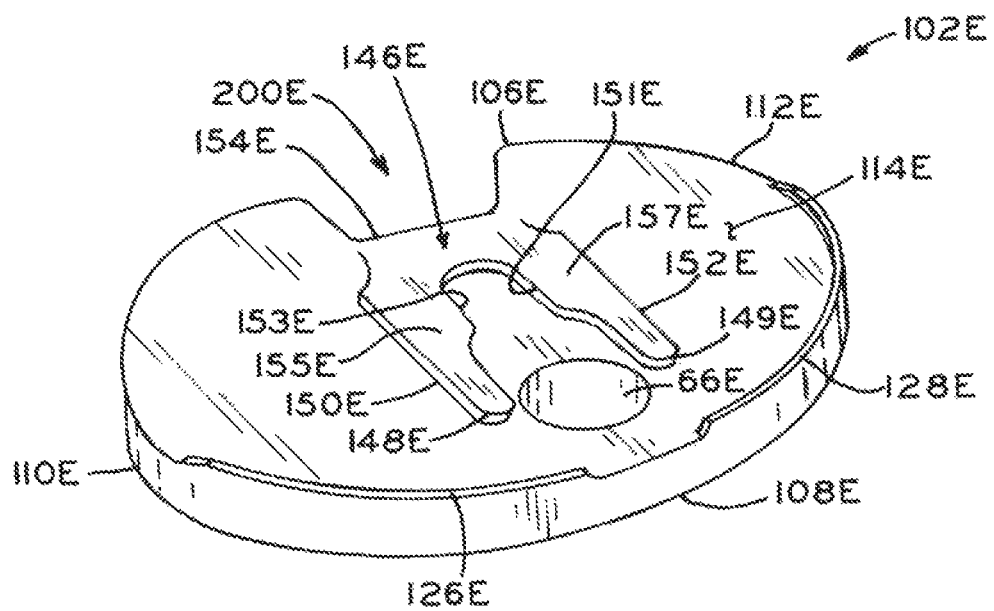
FIG. 22 is a anterior perspective view of the tibial tray of the fifth embodiment.
Figure 23:
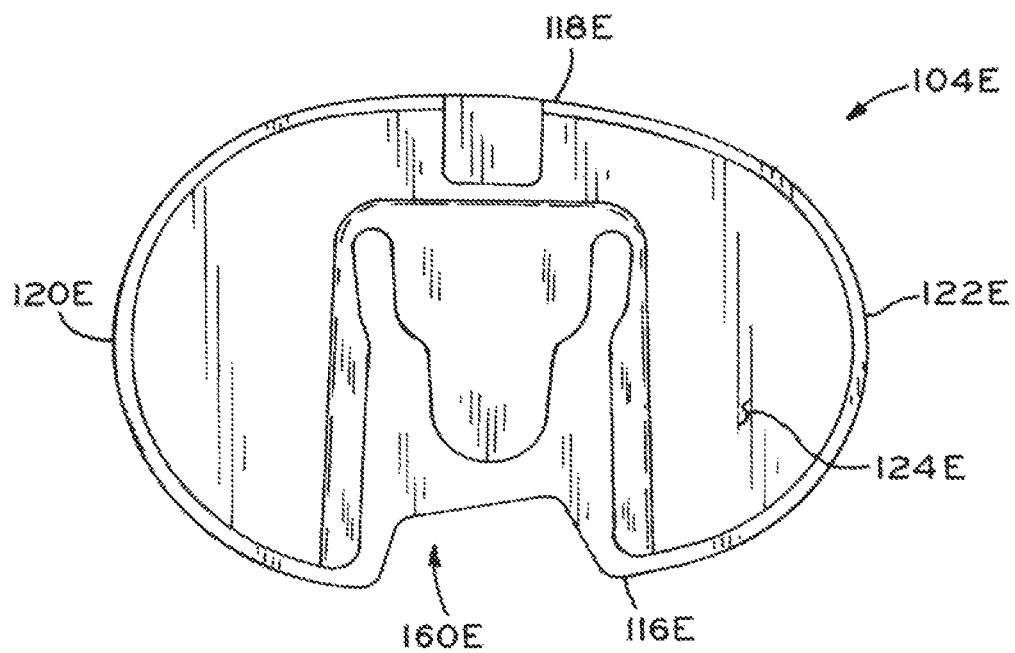
FIG. 23 is a distal plan view of the bearing component of the fifth embodiment.
Figure 24:
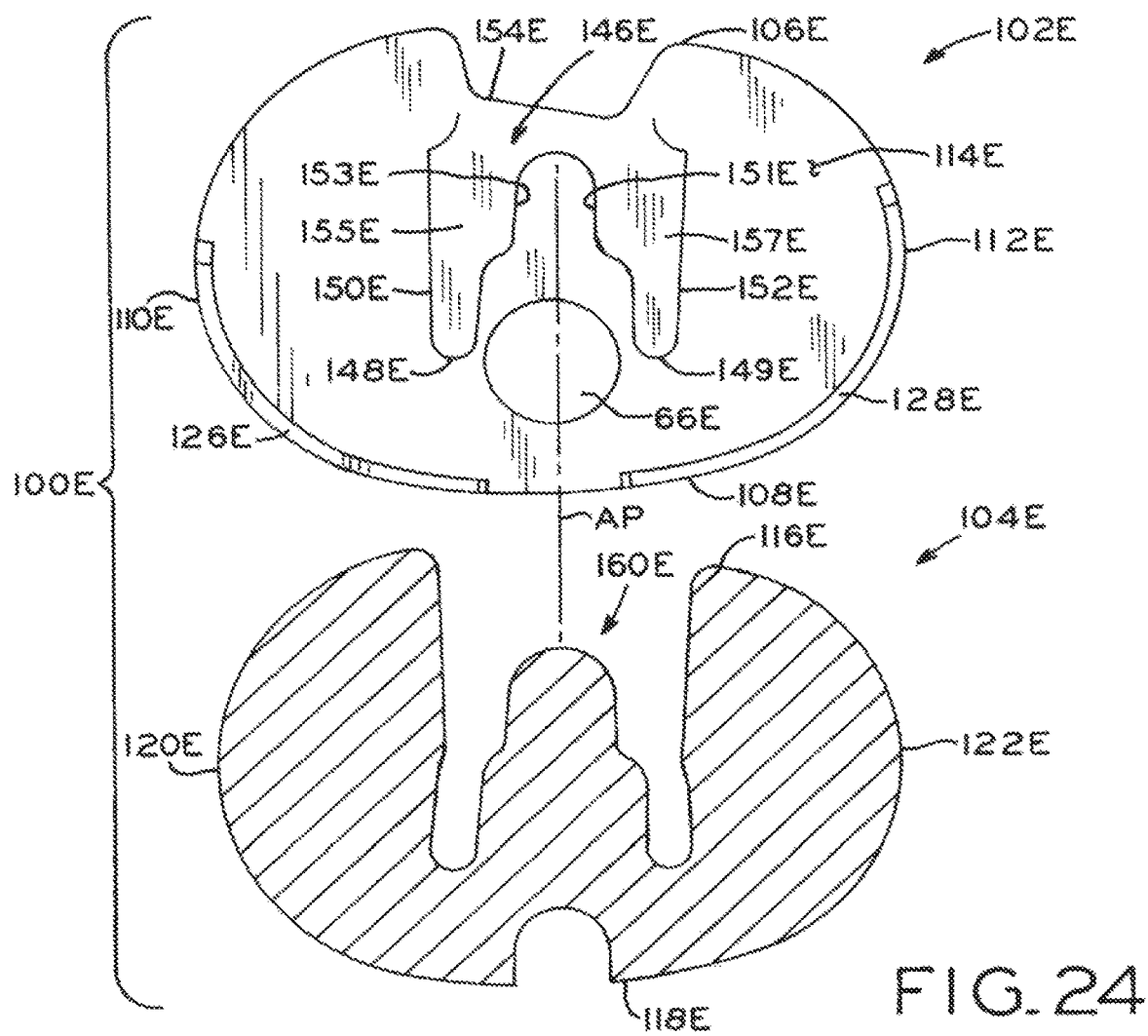
FIG. 24 is a proximal plan, partial sectional view of the tibial prosthesis showing a straight insertion, along a general anterior-posterior axis parallel, to a sagittal plane, of the bearing component onto the tibial tray of the fifth embodiment.
Figure 25:
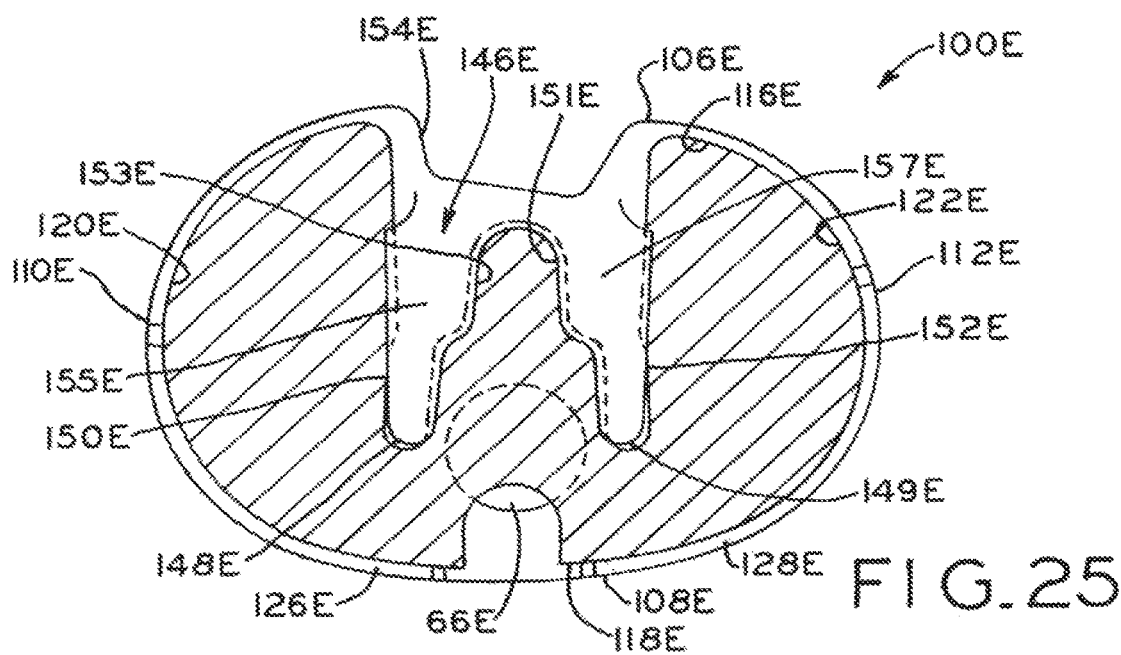
FIG. 25 is a proximal plan, partial sectional view of the tibial prosthesis of FIG. 24, with the bearing component fully seated on the tibial tray.
Figure 26:
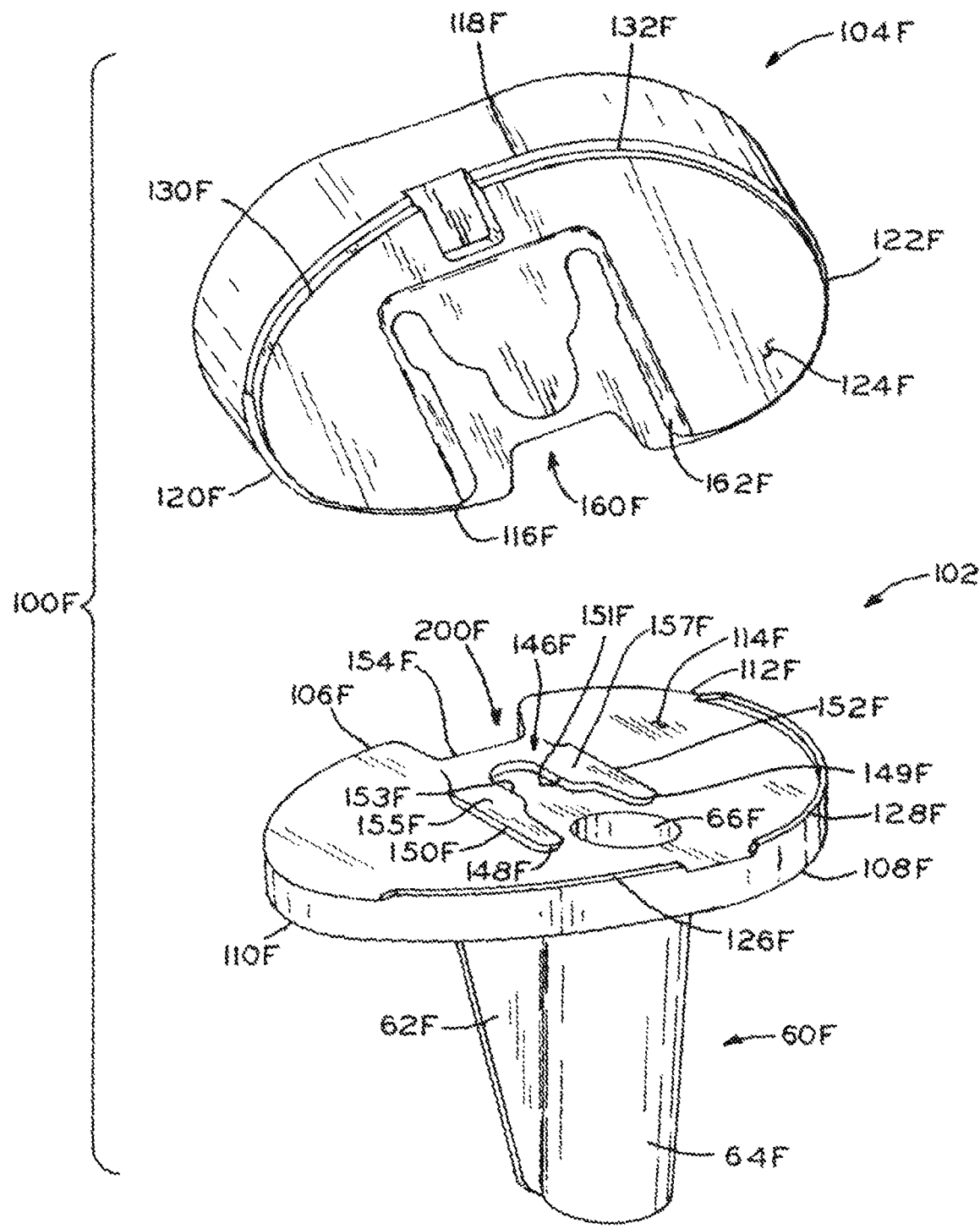
FIG. 26 is an exploded anterior perspective view of a tibial prosthesis made in accordance with an exemplary sixth embodiment of the present invention, including a bearing component and a tibial tray.
Figure 27:
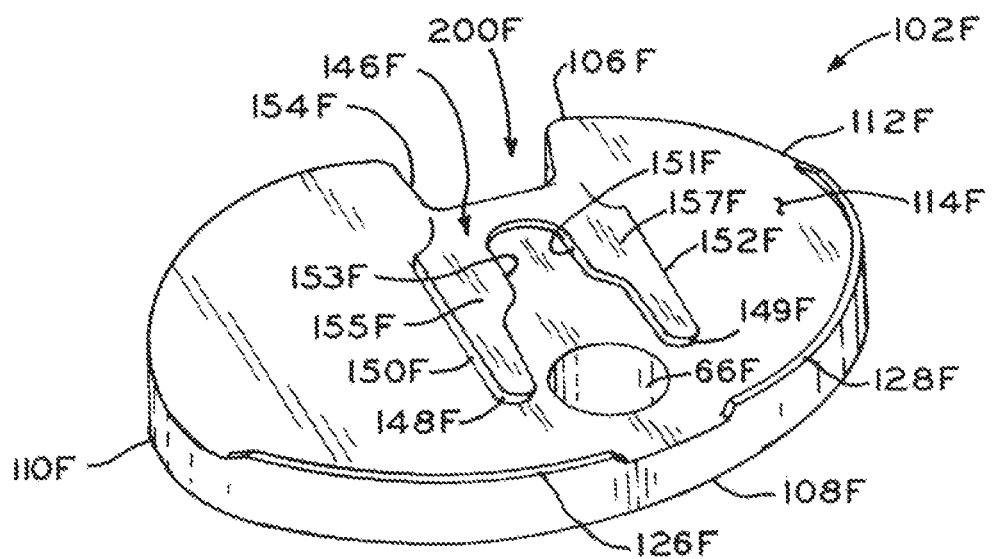
FIG. 27 is a anterior perspective view of the tibial tray of the sixth embodiment.
Figure 28:
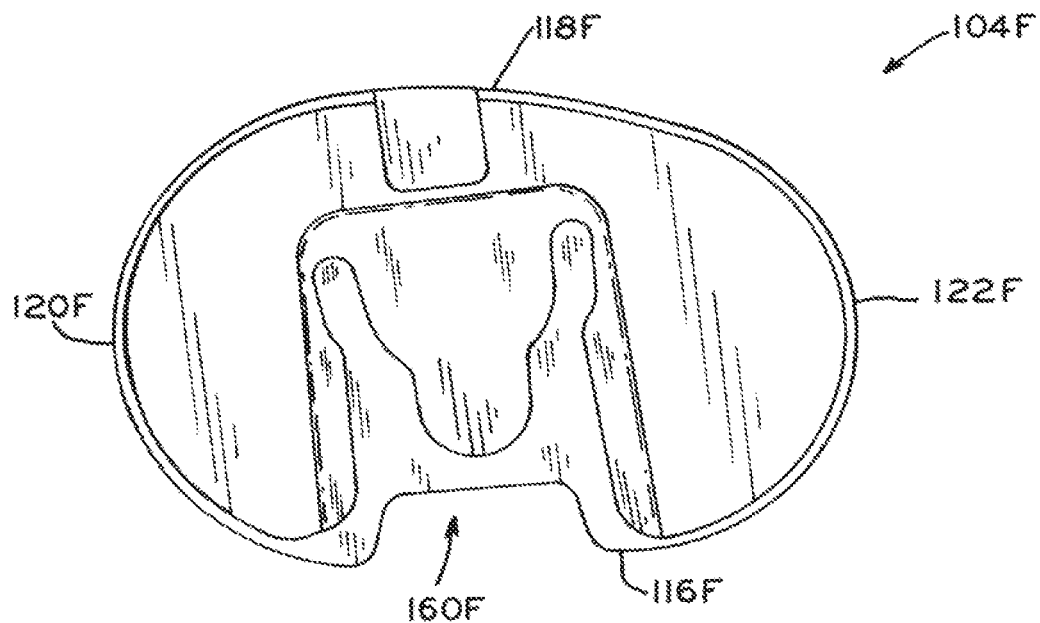
FIG. 28 is a distal plan view of the bearing component of the sixth embodiment.

FIGS. 16-20 illustrate an exemplary fourth embodiment. The exemplary fourth embodiment is similar in structure and method of insertion along axis AP (FIG. 19) to the exemplary third embodiment for securing bearing component 104D atop tibial tray 102D (FIG. 20), similarly including an insertion of hearing component 104D over anterior tails 126D and 128D, but the exemplary fourth embodiment has a different structure for boss 146D (FIGS. 16 and 17) and corresponding notch 160D (FIGS. 16 and 18). Boss 146D has a more V-shaped structure with a more pointed anterior end 148D. Elongated wings 156D and 158D extend from medial side 150D and lateral side 152D, respectively.

Further, boss 146D is laterally offset from a centralized axis of the tibial tray positioned between anterior edge 108D and posterior edge 106D, and accordingly is offset from aperture 66D, to accommodate a medialized stem body and access a drop down screw locking mechanism (not shown), such as a locking screw mechanism used in the Zimmer, Inc. NexGen® LPS-Flex Knee having a 17 mm or greater articular surface assembly. Aperture 66D is used as a secondary lock for a stem extension connected to a distal end of stem shaft 64D, which is machined to have a female taper. The stem extension with a male taper is inserted into the distal end of stem shaft 64D. An axial drop down screw through, aperture 66D threads into the proximal end of the male taper of the stem extension to affix it to stem shaft 64D. Alternatively, such a drop down screw locking mechanism is not included.

Boss 146D, still including undercut anterior end 148D, medial side 150D and lateral side 152D, has anterior end 148D that is elongated towards anterior edge 108D of tibial tray 102D with an elongation sufficient to resist forces attempting to lift bearing component 104D from tibial tray 102D in a final locked position. Medial side 150D and lateral side 152D are not as greatly elongated as disclosed in the exemplary second and third embodiments above.

FIGS. 21-25 illustrate an exemplary fifth embodiment. The exemplary fifth embodiment is more similar to the exemplary third embodiment in that the boss is not offset from a centralized axis positioned between anterior and posterior edges of the tibial tray (such as component home axis M, described in detail above). The exemplary fifth embodiment further follows a method of insertion along axis AP (FIG. 24) that is similar to the described method of the third embodiment.

The shape of boss 146E (FIGS. 21 and 22) differs from boss 146C of the exemplary third embodiment in that, while boss 146E includes posterior end 154E forming a PCL cutout for tibial tray 102E, boss 146E further forms a forked shape extending from posterior end 134E that has a pair of jaws 155E and 157E. Medial jaw 155E laces medial, edge 110B of tibial tray 102E and lateral jaw 157E faces lateral edge 112E of tibial tray 102E. Medial jaw 155E includes medial side 150E, lateral side 153E, and anterior end 148E connecting the sides. Similarly, lateral jaw 157E includes medial side 151E, lateral side 152E, and anterior end 149E connecting the sides. The interior of boss 146E formed by lateral side 153E of medial jaw 155E and medial side 151E of lateral jaw 157E forms a larger U-shaped indent formed anterior to a smaller U-shaped indent, which may be referred to as a "double dovetail" design. The undercut nature of the walls forming boss 146E and the forked formation, along with an elongation of anterior ends 148E and 149E towards anterior edge 108E of tibial tray 102E, allow for an increase in strength to resist forces attempting to lift bearing component 104E from tibial tray 102E in a final seated position (FIG. 25) when boss 146E is received into corresponding notch 160E (FIG. 23) of bearing component 104E.

Alternatively, a tibial prosthesis of the present disclosure may have a tibial tray including a boss having an angled geometry, or rather, a boss that is canted with respect to a generally anterior-posterior axis parallel to the sagittal plane (i.e., axis AP). Such a canted boss advantageously allows for avoidance of the extensor mechanism upon. Implantation of the tibial prosthesis, particularly, the implantation of a bearing component with a notch sized to receive the canted boss of the tibial tray atop the tibial tray.

The angled boss configuration is angled with respect to a sagittal plane to define an offset axis angle. The offset axis angle defines an offset with respect to an axis parallel to the sagittal plane. This angled configuration allows for an anterior-medial inserted, bearing component to be urged atop the tibial tray at the offset axis angle to lock with the tibial tray during an insertion that is conducted along a single anterior-medial insertion trajectory. The bearing component of the canted boss embodiments of the present disclosure may be inserted at an offset axis angle ranged from about 8 degrees to about 10 degrees with respect to a generally anterior-posterior reference axis positioned through an anterior edge of the tibial tray. Alternatively, the bearing component may be inserted at an offset axis angle ranging from about 0 degrees to about 90 degrees, or from about 1 degrees to about 90 degrees, or from about 0 degrees to about 30 degrees, or from about 1 degrees to about 30 degrees from the generally anterior-posterior reference axis. Further as an alternative, the offset axis angle may range from about 0 to 90 degrees may be an angle as small as 0, 1, 2, 3, 4, 5, 6, 7, or 8 degrees, or as great as 9, 10, 20, 30, 40, 50, 60, 70, 80, or 90 degrees, or may be any value within any range defined by any of the foregoing values. The medial and lateral sides of the associated boss will be angled with respect to the offset axis at same or different angles. The medial and lateral side angles may each be selected from a range of about 0 degrees to 15 degrees, or about 5 degrees to 10 degrees.

Figure 29:
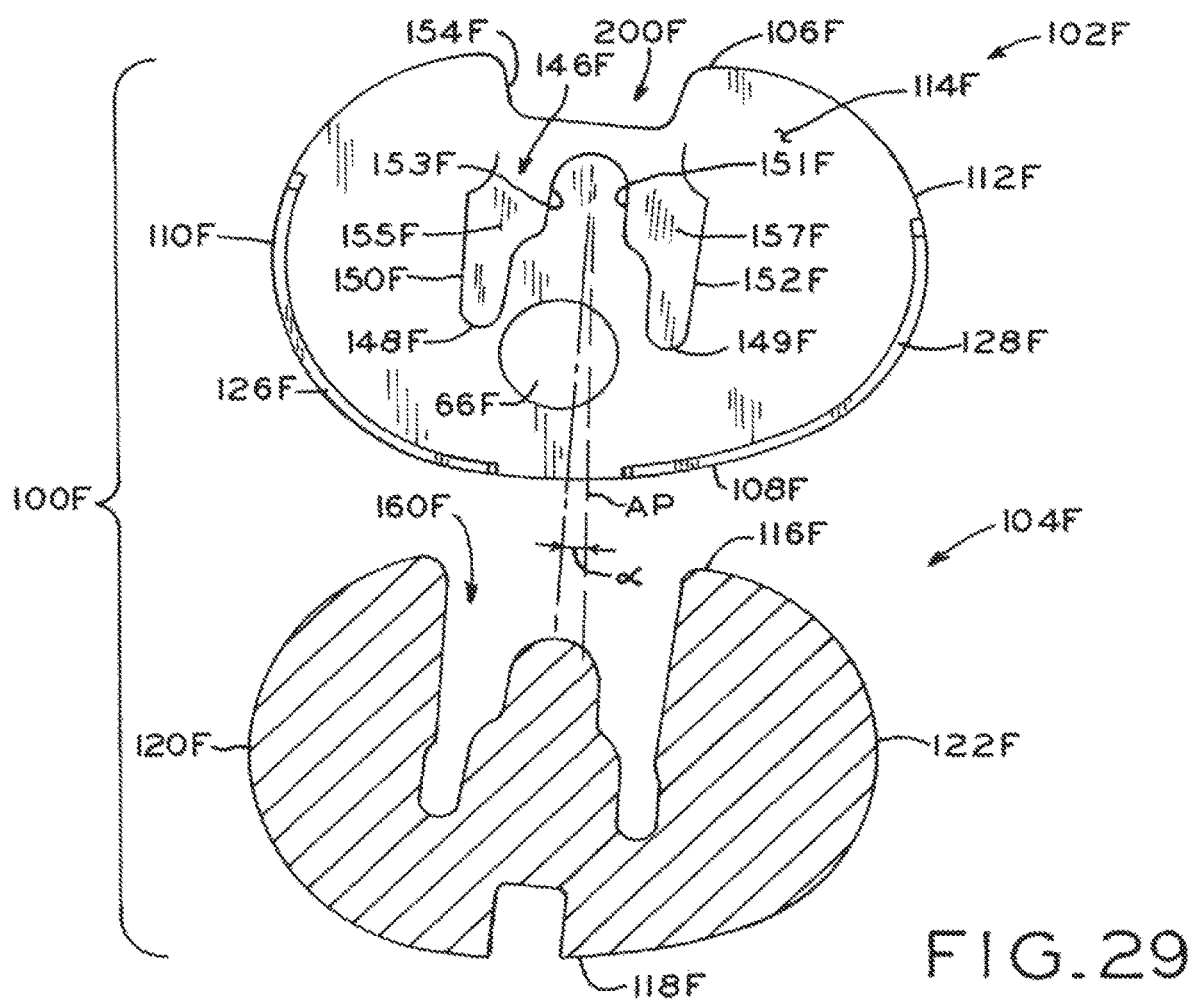
FIG. 29 is a proximal plan partial sectional view of the tibial prosthesis showing an anterior-medial insertion at an angle of the bearing component onto the tibial tray of the sixth embodiment.

For example, FIGS. 26-30 illustrate an exemplary sixth embodiment having a canted boss. As described with respect to the exemplary fifth embodiment, the sixth embodiment includes boss 146F (FIGS. 26 and 27) having forked jaws 155F and 157F. However, boss 146F of the exemplary sixth embodiment is canted with respect to axis AP at angle α (FIG. 29). Boss 146F may be angled at an offset axis angle that is 8 to 10 degrees medial of the sagittal plane.

After tibial tray 102F is positioned within a knee through an incision, such as incision S as shown in FIG. 56, which provides access to the knee during surgery along an anterior-medial insertion angle. Bearing component 104F is inserted atop tibial tray 102F along the anterior-medial insertion path, thereby avoiding the extensor mechanism of the knee as mentioned above. Particularly, bearing component 104F (FIG. 28) is inserted through incision S (FIG. 56) in an anterior-medial insertion direction to an initial reception position where a posterior end of notch 160F of bearing component 104F receives anterior ends 148F and 149F of boss 146F of tibial tray 102F. Recessed indent 162F of notch 160F proceeds to receive the anterior, medial, and lateral walls forming boss 146F along an angle relative to the sagittal plane, which is the same angle at which medial side 150F and lateral side 152F are positioned relative to the sagittal plane.

Recessed indent 162F (FIG. 26) receives the above-mentioned walls of boss 146F. Further, as bearing component 104F is inserted over tibial tray 102F, bearing component 104F is inserted over anterior rails 126F and 128F of tibial tray 102F to engage in a final snap-fit connection with anterior rails 126F and 128F. Alternatively, anterior rails 126F and 128F may include a pair of extended perimeter ends from which a pair of rails project. Bearing component 104F may then include a pair of internal grooves having a thickness for receipt of the respective pair of rails such that the pair of rails have a corresponding thickness that substantially fill the grooves.

If boss 146F has walls which are undercut, the corresponding walls of recessed indent 162F experience elastic deformation similar to the deformation described in detail above with respect to tibial prosthesis 100A. This deformation occurs due to the insertion of bearing component 104F over anterior rails 126F and 128F of tibial tray 102F as distal surface 124F is separated from support surface 114F of tibial tray 102F. When an undercut is provided in the boss rail and/or peripheral rails, the deformation that occurs as described above coupled with frictional forces experienced by the interaction of the described portions of bearing component 104F and tibial tray 102F progressively increases resistance to movement of bearing component 102F along a path defining angle α (FIG. 29) with respect to a reference axis until anterior edge 118F of bearing component 104F passes anterior rails 126F and 128F of tibial tray 102F. Then, bearing component 104F snaps into position in a firm conception created by the operation of anterior edge 118F with an interior side of anterior rails 126F and 128F (FIG. 30).

Additionally, the walls forming boss 146P are undercut and are received by corresponding walls of indented recess 162F such that any gaps between the walls forming the surfaces of boss 146F and notch 160F are filled.

Figure 30:
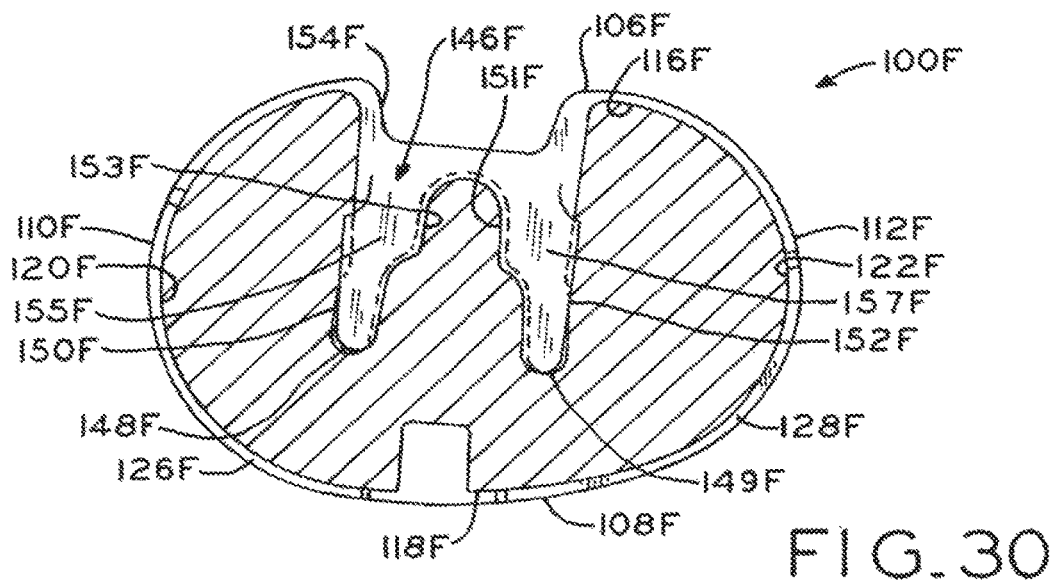
FIG. 30 is a proximal plan, partial sectional view of the tibial prosthesis of FIG. 29, with the bearing component fully seated on the tibial tray.
Figure 31:
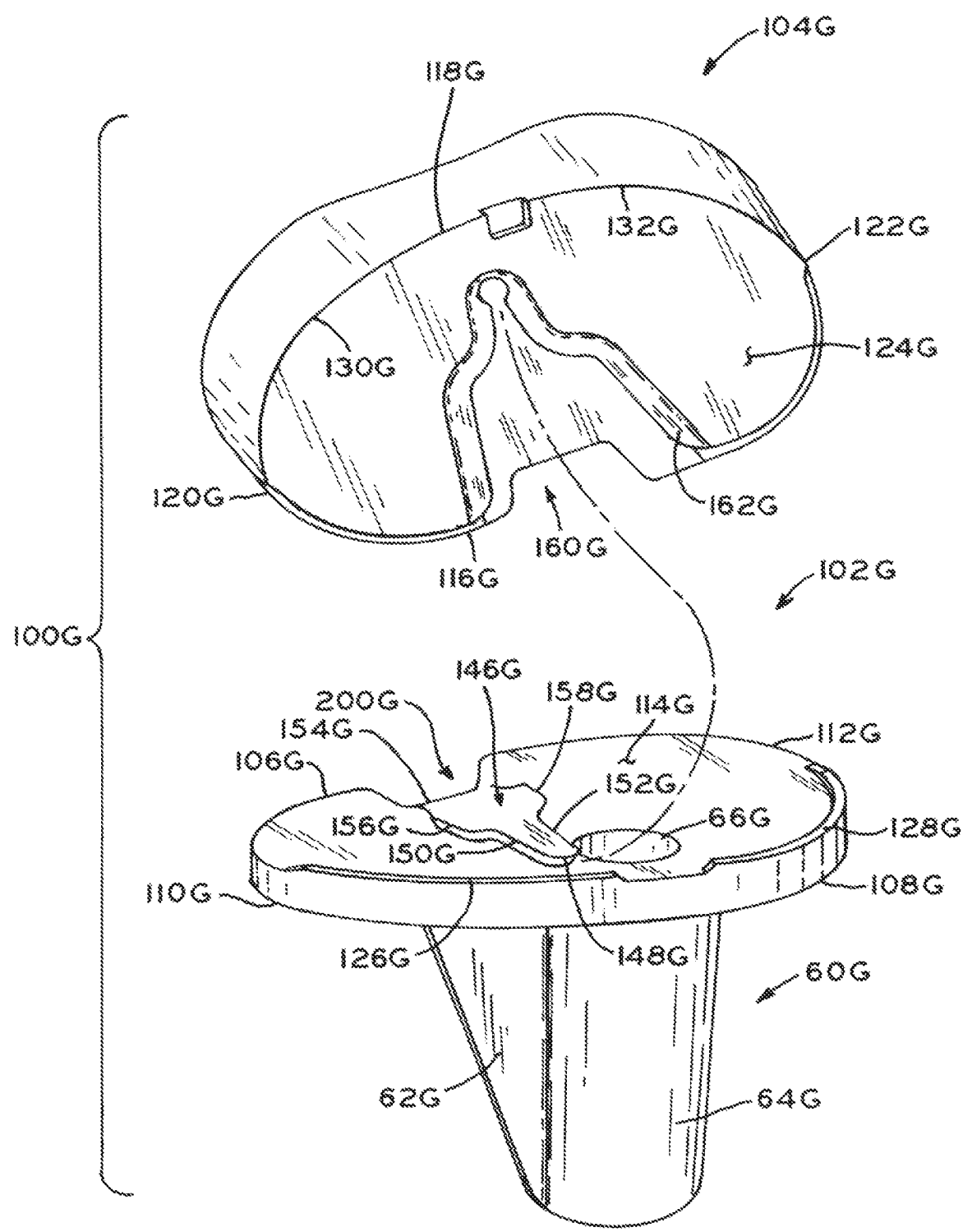
FIG. 31 is an exploded anterior perspective view of a tibial prosthesis made in accordance with an exemplary seventh embodiment of the present invention, including a bearing component, and a tibial tray.
Figure 32:
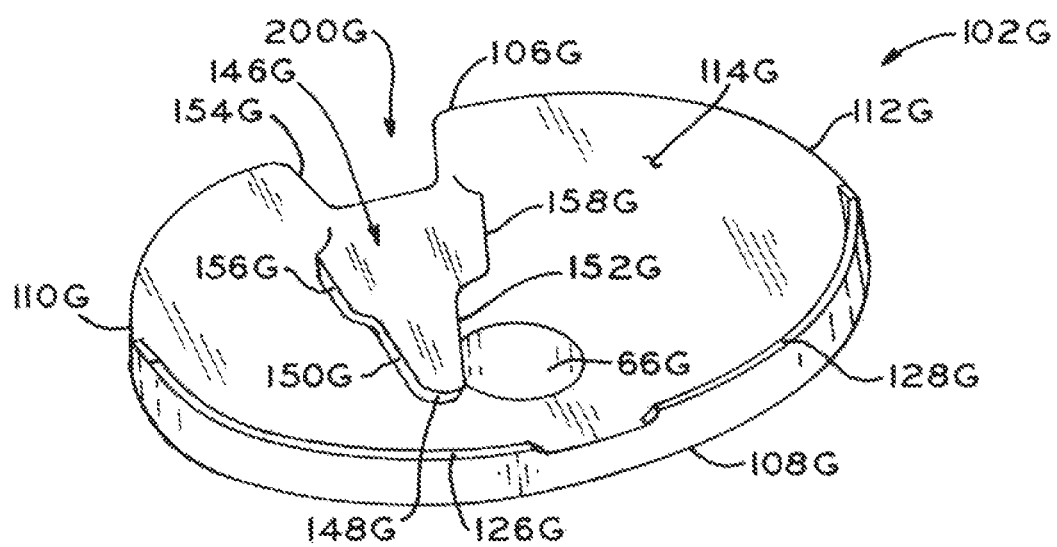
FIG. 32 is a anterior perspective view of the tibial tray of the seventh embodiment.

Referring to FIG. 30, when bearing component 104F is seated atop 102F, anterior movement is prevented by the abutment of anterior edge 118F of bearing component 104F with an interior side of anterior rails 126F and 128F. Further, posterior movement is prevented by the abutment of a wall forming anterior ends 148F and 149F of boss 146F with respective anterior ends of recessed indent 162F (FIG. 26) formed within notch 160F. Further, the elongation of undercut anterior ends 148F and 149F of boss 146F is sufficient to overcome forces attempting to lift bearing component 104F off tibial tray 102F during natural joint articulation.

Figure 33:
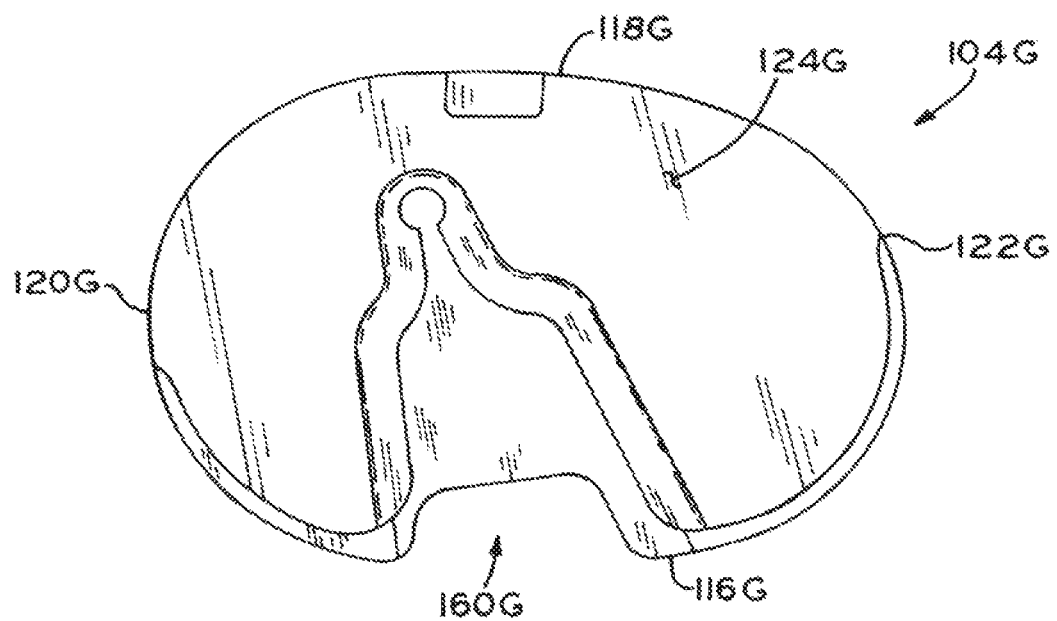
FIG. 33 is a distal plan view of the bearing component of the seventh embodiment.
Figure 36:
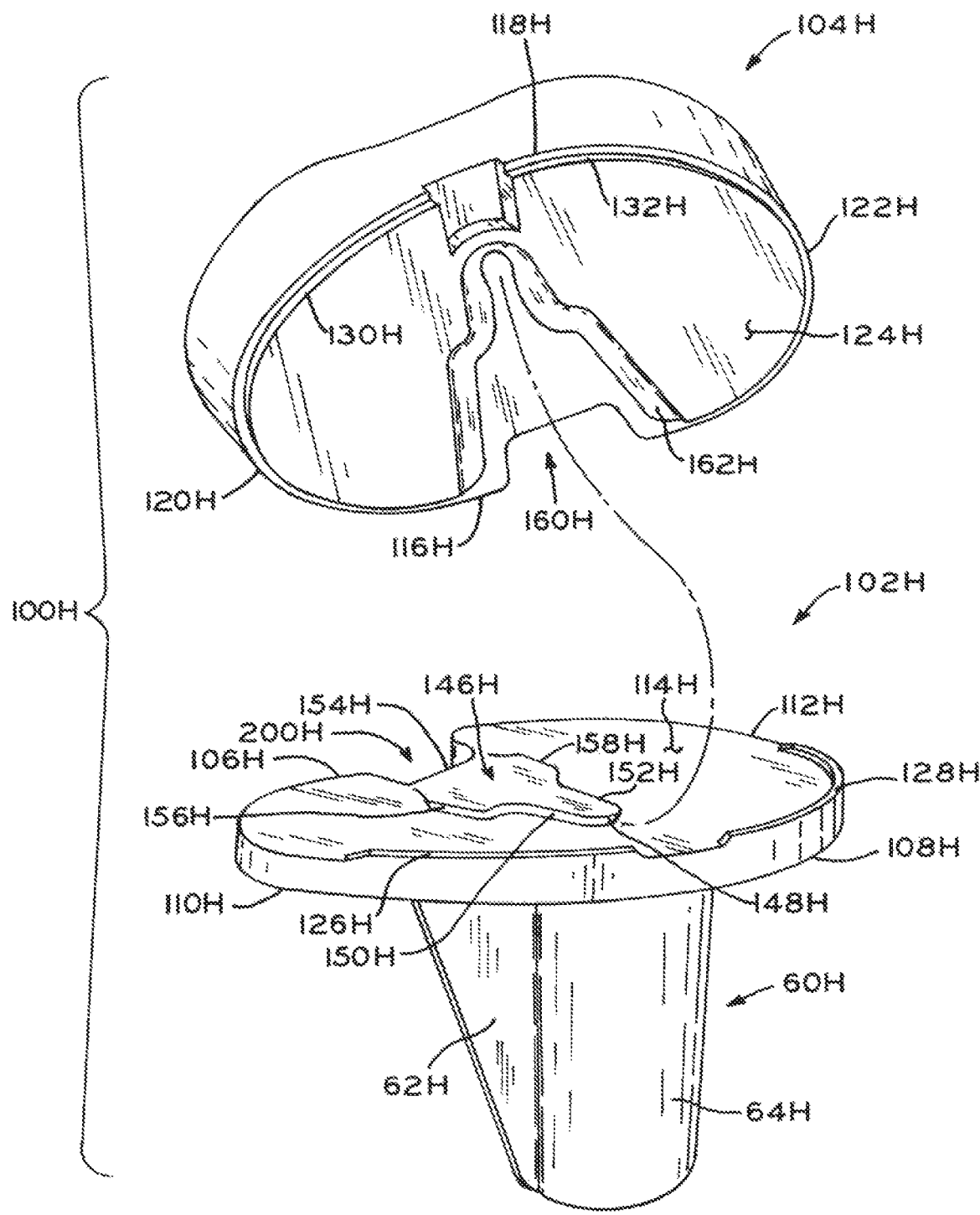
FIG. 36 is an exploded anterior perspective view of a tibial prosthesis made in accordance with an exemplary eighth embodiment of the present invention, including a bearing component and a tibial tray.
Figure 37:
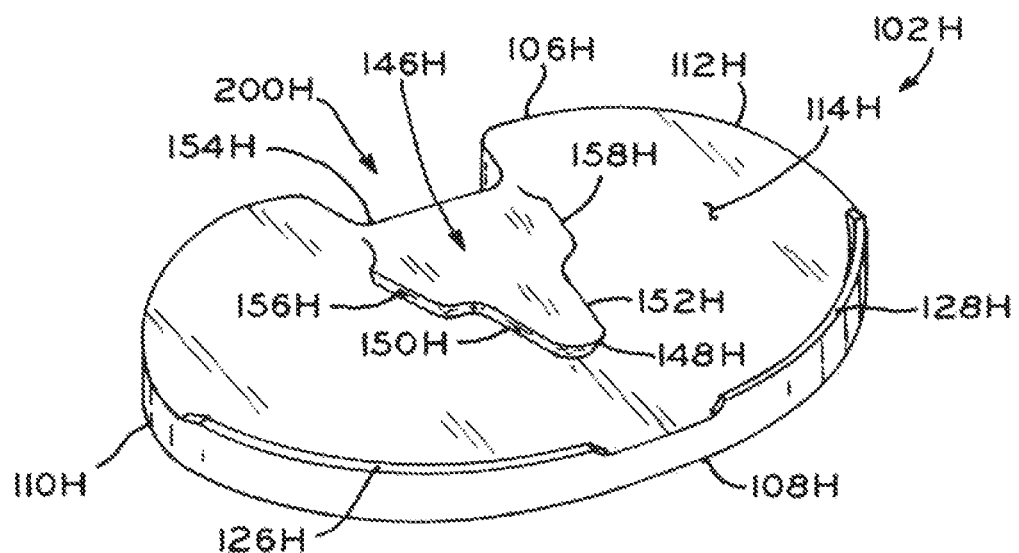
FIG. 37 is a anterior perspective view of the tibial tray of the eighth embodiment.
Figure 38:
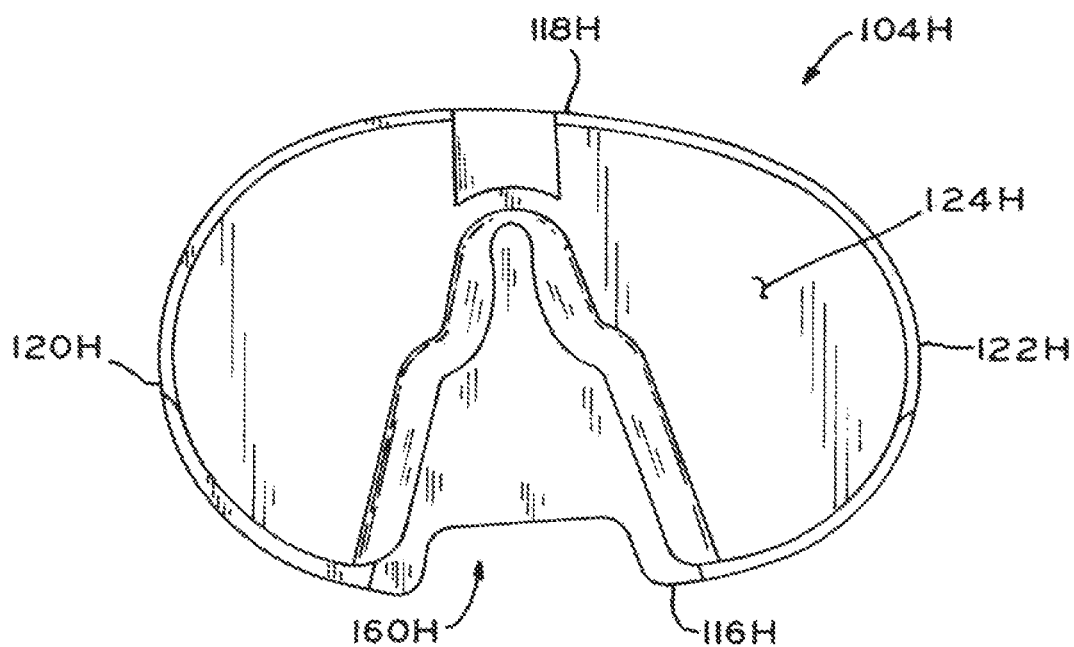
FIG. 38 is a distal plan view of the bearing component of the eighth embodiment.
Figure 39:
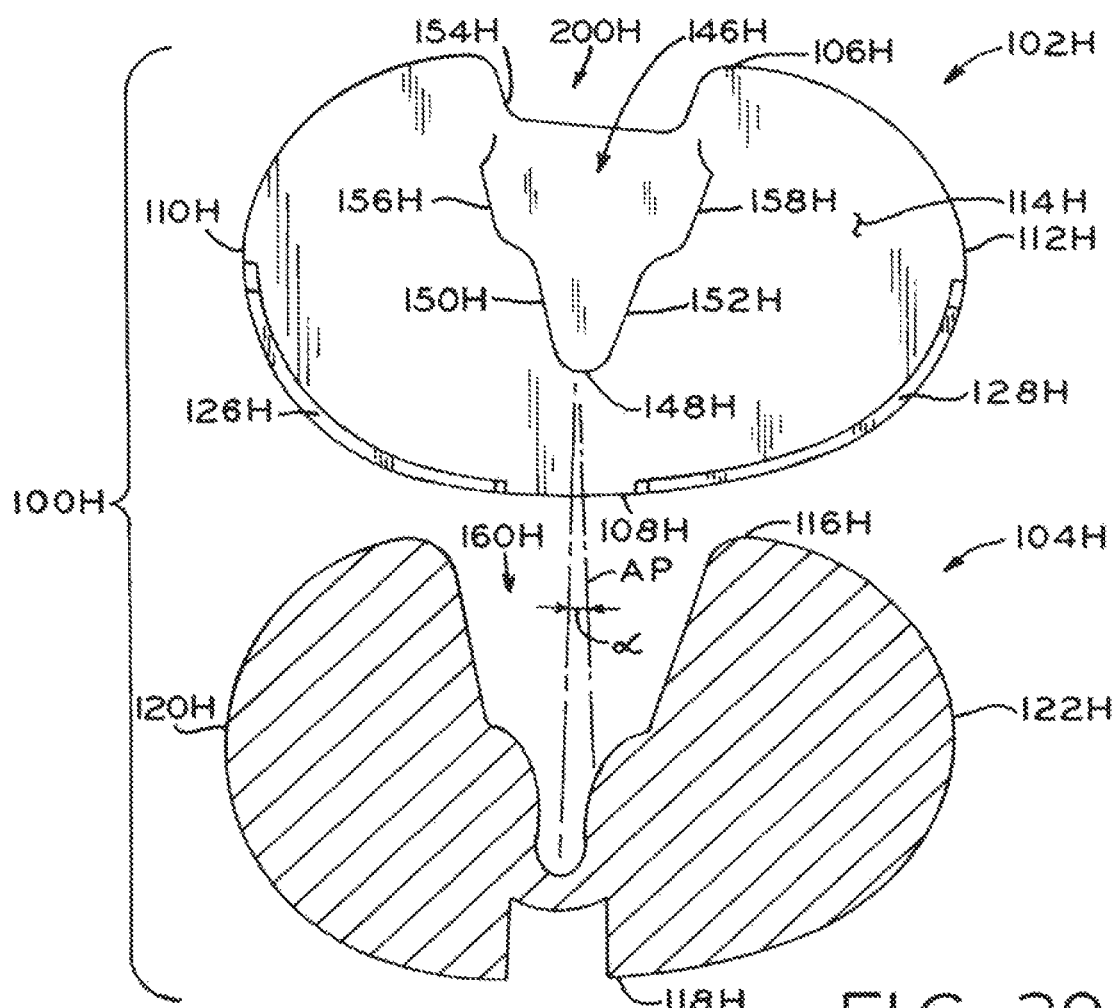
FIG. 39 is a proximal plan, partial sectional view of the tibial prosthesis showing an anterior-medial insertion at an angle of the bearing component onto the tibial tray of the eighth embodiment.
Figure 40:
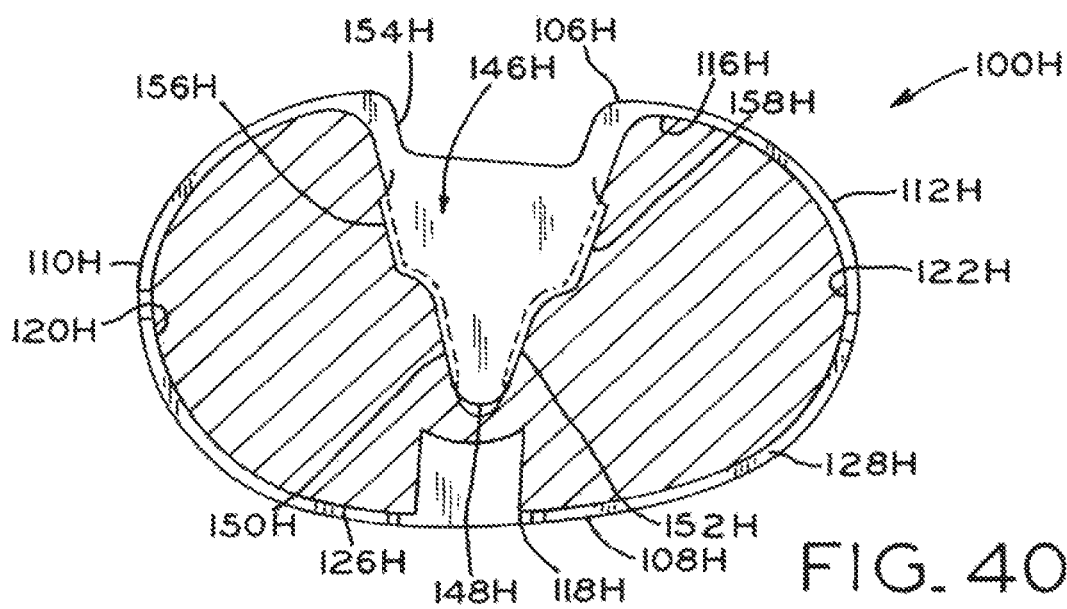
FIG. 40 is a proximal plan, partial sectional view of the tibial prosthesis of FIG. 39, with the bearing component fully seated on the tibial tray.
Figure 41:
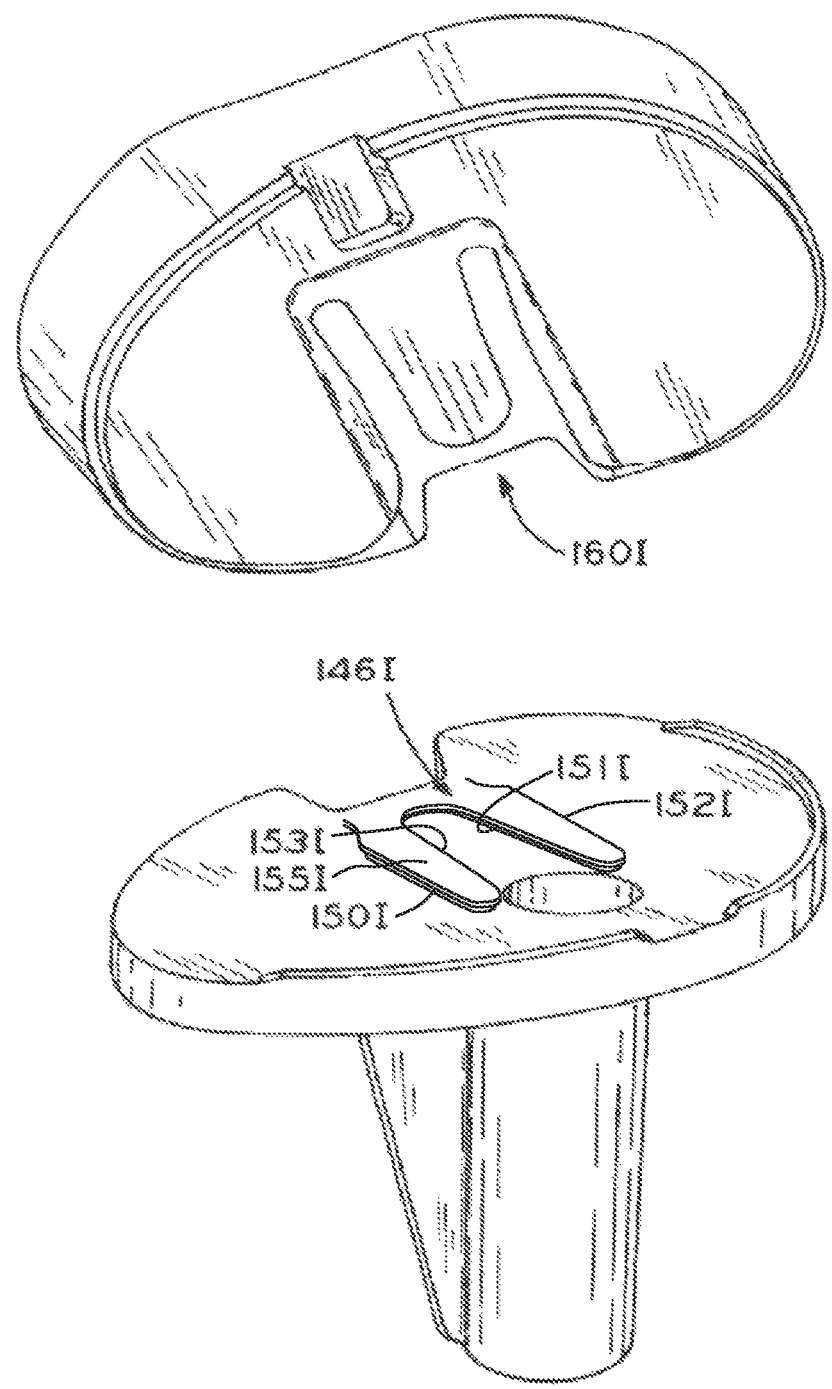
FIG. 41 is an exploded anterior perspective view of a tibial prosthesis made in accordance with an exemplary ninth embodiment of the present invention, including a bearing component and a tibial tray.
Figure 42:
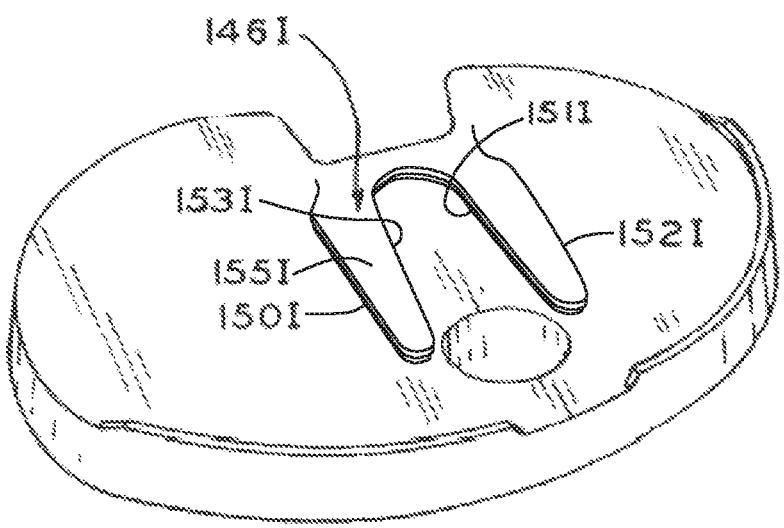
FIG. 42 is a anterior perspective view of the tibial tray of the ninth embodiment.

FIGS. 31-35 illustrate an exemplary seventh embodiment in which a tibial tray includes another canted boss. The manner of insertion of the seventh embodiment along a canted path defined by angle α with respect to axis AP (FIG. 34) is similar to that described for the exemplary sixth embodiment above. However, the exemplary seventh embodiment includes a canted boss that does not include a forked jaw structure. Rather, boss 146G of tibial tray 102G (FIGS. 31, 32, 34, and 35), while including posterior end 154G forming a PCL cutout for tibial tray 102G, includes undercut anterior end 148G, undercut medial side 150G, and undercut lateral side 152G. Lateral side 152G and medial side 150G are elongated towards anterior edge 108G of tibial tray 102G, and anterior end 148G connects lateral side 152G and medial side 150G. In other words, anterior end 148G is elongated towards anterior edge 108G of tibial tray 102G. The shape of boss 146G with wings 156G and 158G on medial side 150G and lateral side 152G, respectively, is similar to the V-shape of boss 146D including wings 156D and 158D on medial side 150D and lateral side 152D, respectively, in the exemplary fourth embodiment. Similarly to the fourth embodiment (shown, in FIGS. 16-20), boss 146G is received into corresponding notch 160G (FIG. 33).

FIGS. 36-40 illustrate an exemplary eighth embodiment in which a tibial tray includes another canted boss. The manner of insertion of the eighth embodiment along a canted path defining angle α with respect to axis AP (FIG. 39) is also similar to that described for the exemplary sixth embodiment above. However, the exemplary eighth embodiment includes boss 146H similarly shaped to the boss of the exemplary fourth embodiment, though boss 146B (FIGS. 36, 37, 39, 40) of the eighth embodiment is larger in shape and includes a greater anterior elongation. Boss 146H includes posterior end 154H forming a PCL cutout for tibial tray 102H, anterior end 148H elongated towards anterior edge 108B of tibial tray 102B, angled and undercut medial side 150H having wing 156H, and angled and undercut lateral side 152H having wing 158H. Boss 146H may be angled along medial side 150H and lateral side 152H, for example, at an angle that is 5 degrees medial of the sagittal plane. Similar to the method described above for the sixth embodiment, boss 146H is received into corresponding notch 160H (FIG. 38) of bearing component 104H.

Figure 43:
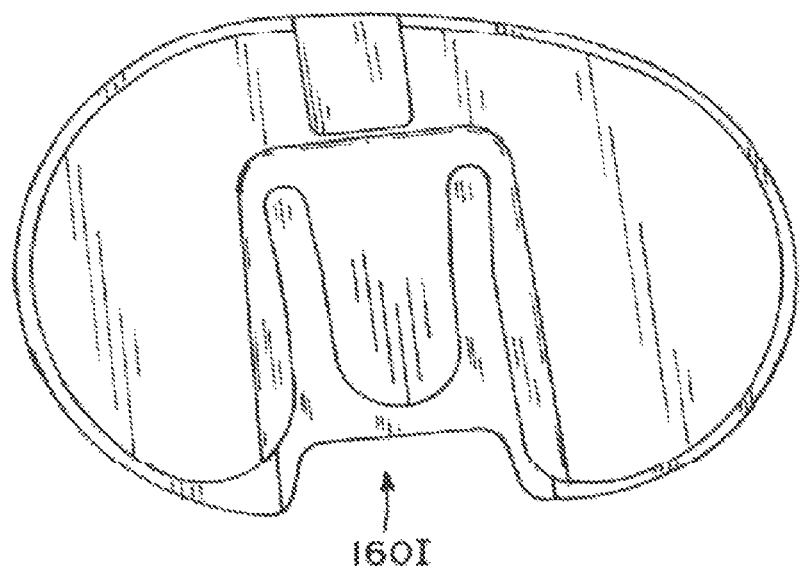
FIG. 43 is a distal plan, view of the bearing component of the ninth embodiment.
Figure 44:
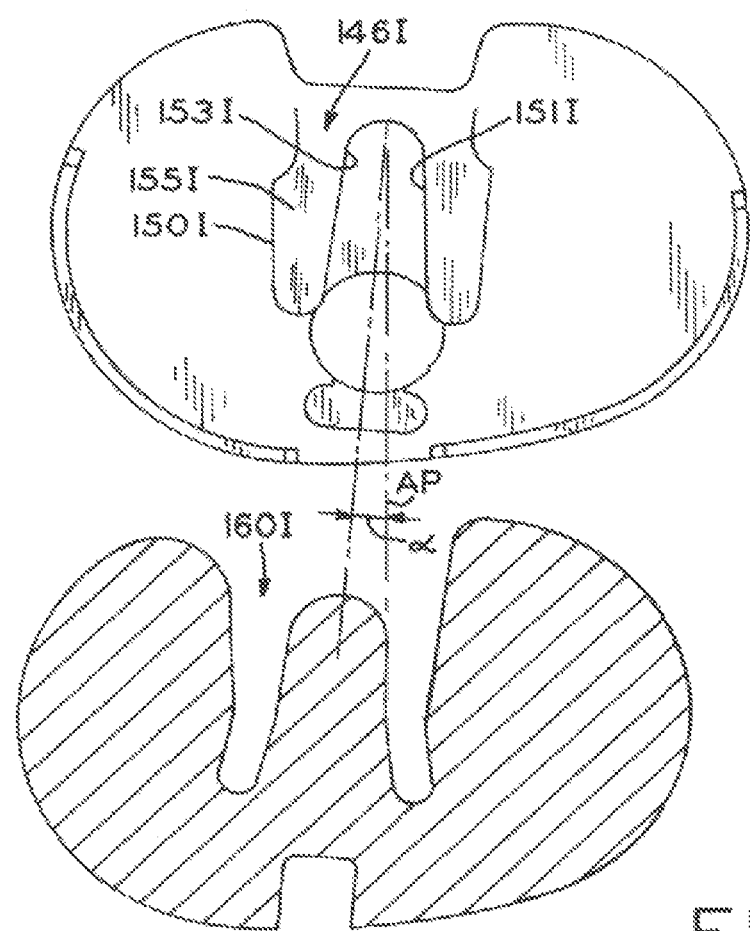
FIG. 44 is a proximal plan, partial sectional view of the tibial prosthesis showing an anterior-medial insertion at an angle of the bearing component onto the tibial tray of the ninth embodiment.
Figure 45:
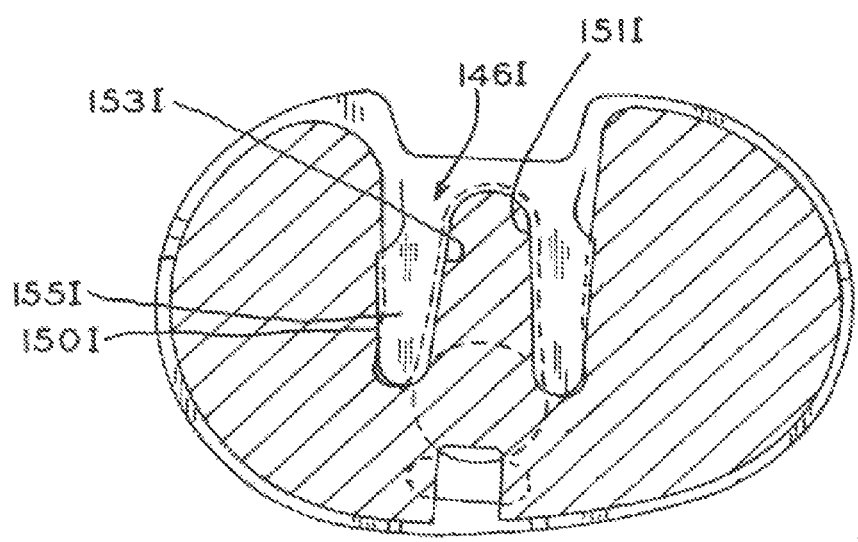
FIG. 45 is a proximal plan, partial sectional view of the tibial prosthesis of FIG. 44, with the bearing component fully seated on the tibial tray.

FIGS. 41-45 illustrate an exemplary ninth embodiment in which a tibial tray includes another form of a canted boss. The manner of insertion of the ninth embodiment along a canted path defined by angle α with respect to axis AP (FIG. 44) is also similar to that described for the exemplary sixth embodiment above. Further, boss 146I is similarly received into corresponding notch 160I (FIG. 43). However, the exemplary ninth embodiment includes boss 146I (FIGS. 41, 42, 44, and 45) that is similar to boss 146F of the exemplary sixth embodiment but includes a slimmer form with less of a measurable width between medial sides 150I and 151I and lateral sides 153I and 152I, respectively. Further, an interior recess formed between medial side 151I and lateral side 153I includes a singular U-shape. Medial side 150I and lateral side 152I of boss 146I may be angled by an offset axis angle that is 8 to 10 degrees medial of the sagittal plane.

The following exemplary embodiments of the present disclosure are shown and described herein with specific reference to a right knee application, although the associated tibial prostheses may also be configured for use in a left knee application.

Figure 49:
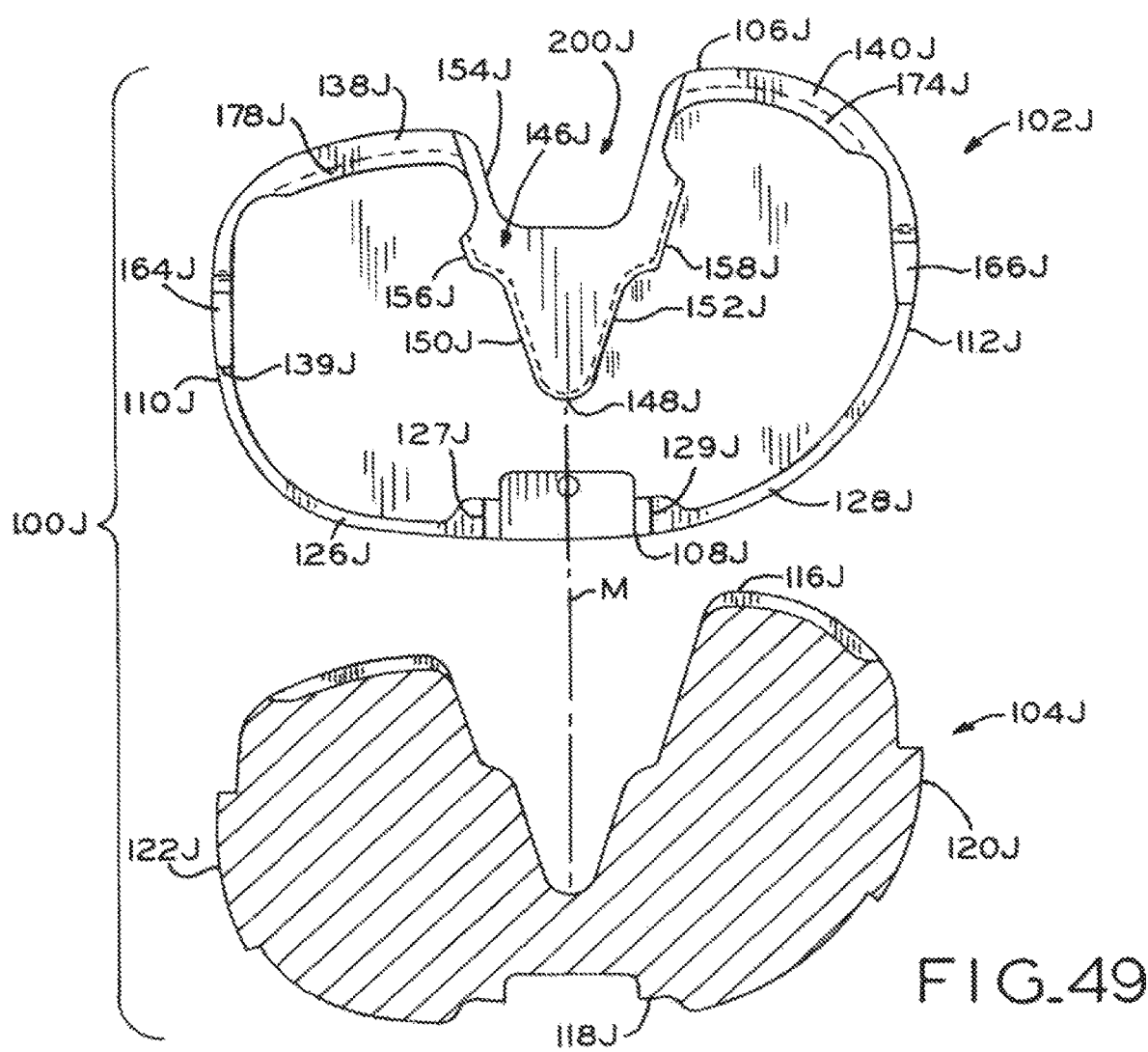
FIG. 49 is a proximal plan, partial sectional view of the tibial prosthesis showing a straight insertion, along an anatomic home axis, of the bearing component onto the tibial tray of the tenth embodiment.

FIGS. 46-50 illustrate an exemplary tenth embodiment having an axis of the PCL cutout of the tibial tray aligned with home axis M. While boss 146J (FIG. 46) of the exemplary tenth embodiment is similar to boss 146H of the exemplary eighth embodiment, boss 146J is no longer canted but is positioned parallel to an axis referred to herein as the home axis, or rather, axis M (FIG. 49). Specifically, an axis of the PCL cutout of tibial tray 102J is oriented along, aligned with and symmetrical with respect to axis M. Orientation about axis M advantageously assists with preventing rotation of tibial tray 102J when implanted in the tibia (not shown) and assists with the creation of a tibial tray that matches the profile of the bone at points of attachment.

Figure 46:
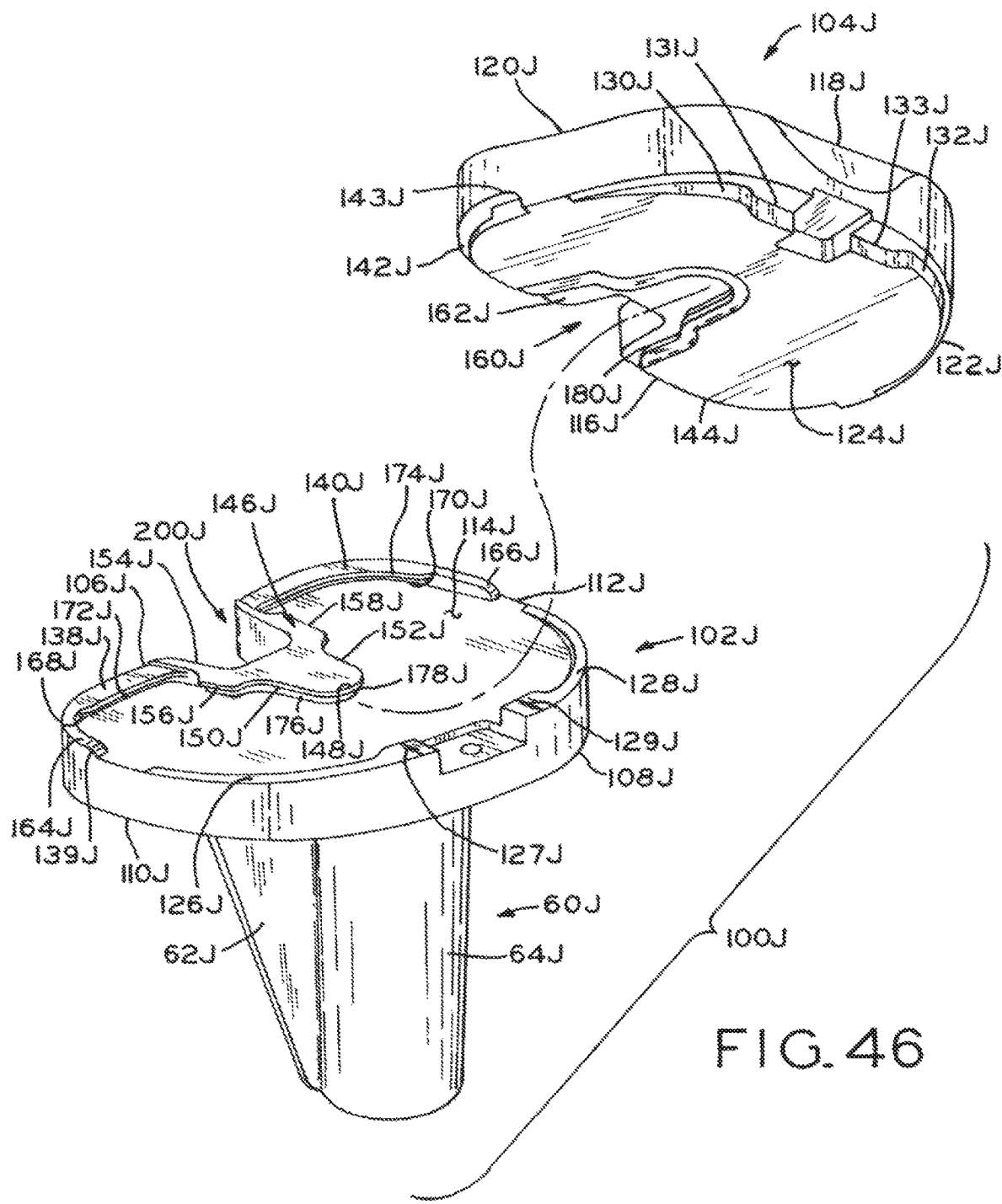
FIG. 46 is an exploded anterior perspective view of a tibial prosthesis made in accordance with an exemplary tenth embodiment of the present invention, including a bearing component and a tibial tray.
Figure 47:
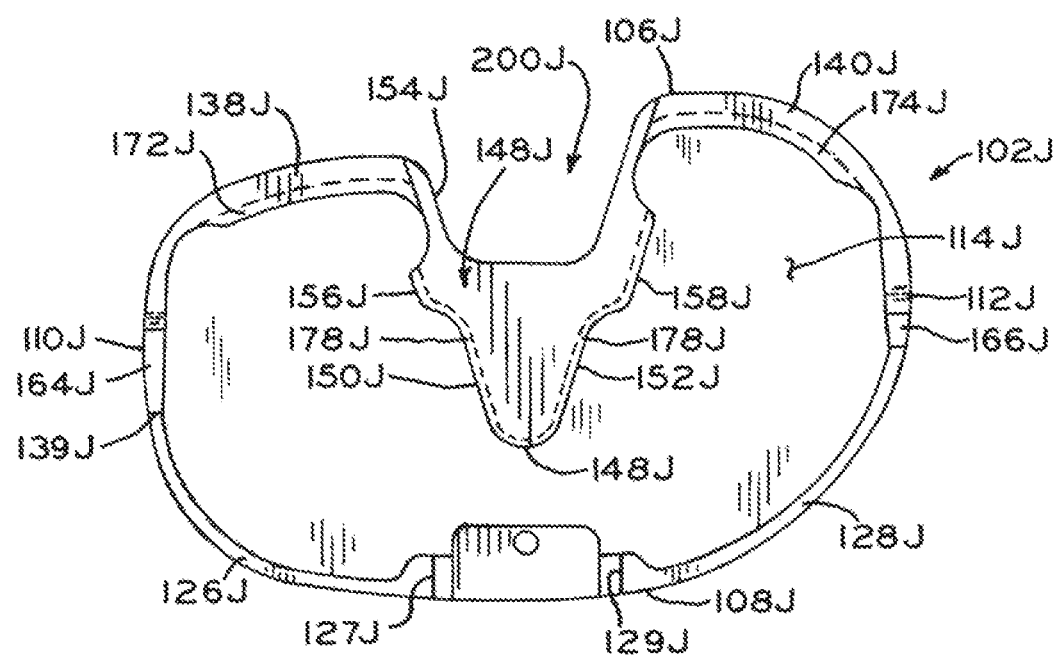
FIG. 47 is a proximal plan view of the tibial tray of the tenth embodiment.
Figure 48:
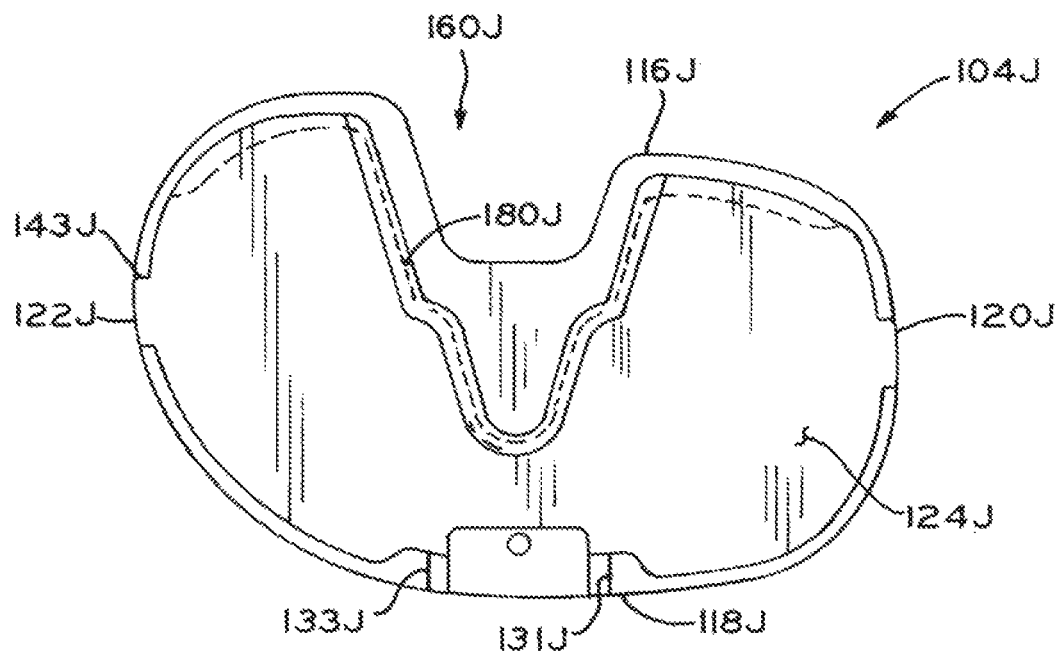
FIG. 48 is a distal, plan view of the bearing component of the tenth embodiment.

Referring to FIGS. 46, 47, and 49, the exemplary tenth embodiment further includes a pair of posterior rails 138J and 140J that extend into lateral containment rail 164J and medial containment rail 166J, respectively. Posterior rails 138J and 140J include extended perimeter ends 168J and 170J from which perimeter rails 172J and 174J respectively project towards anterior edge 108J of tibial tray 102J. Perimeter rails 172J and 174J have a substantially similar thickness. Alternatively, perimeter rails 172J and 174J may have an increasing thickness towards posterior edge 106J of tibial tray 102J. As posterior rails 138J and 140J include a pair of extended perimeter ends from which a pair of perimeter rails project, bearing component 104J includes a pair of internal grooves having a thickness for receipt of the respective pair of rails such that the pair of rails have a corresponding thickness that substantially fill the grooves.

A pair of anterior rails 126J and 128J each include thicker portions 127J and 129J (relative to the rest of the rail) at anterior most ends which are received into corresponding thicker anterior rail recessed portions 131J and 133J of respective anterior rail recesses 130J and 132J. Anterior rails 126J and 128J each include an interior wall facing an opposite direction from the edge on which the respective anterior rail is positioned. Anterior rails 126J and 128J are additionally containment rails in the sense that the respective interior walls include a straight edge from proximal from support surface 114J which do not include an undercut. Such containment rails resist rotation of bearing component 104J atop tibial tray 102J and simultaneously inhibits micromotion in the anterior and posterior directions. Anterior rails 126J and 128J are ramped with a greater spaced distance near anterior edge 108J than near lateral and medial edges 110J and 112J, respectively. Similarly, lateral containment rail 164J includes an interior wall facing medial containment rail 166J, and medial containment rail 166J includes an interior wall facing lateral containment rail 164J. Each of the interior walls include a straight edge projecting proximally from support surface 114J and do not include art undercut. Further, lateral containment rail 164J and medial containment rail 166J are vertically ramped or stepped towards support surface 114J at ends closer to anterior edge 108J. The containment rails 166J and 164J may additionally may horizontally ramped such that each rail may have a greater transverse thickness at the stepped portion than at a portion closer to a respective posterior end.

Boss 146J includes posterior end 154J, anterior end 148J, lateral side 150J, and medial side 152J. Lateral and medial sides 150J and 152J each include wings 156J and 158J, respectively. Anterior end 148J is elongated towards anterior edge 108J of tibial tray 102J with an elongation sufficient to resist forces attempting to lift bearing component 104J from 102J upon a final seating. Anterior end 148J, lateral side 150J and medial side 152J include an edge 176J from which boss rail 178J projects. Boss rail 178J is received into boss rail recess 180J (FIGS. 46 and 48) of notch 160J and the walls forming edge 176J are similarly received into a recess of notch 160J such that any gaps between the walls forming boss 146J and notch 160J are substantially filled.

After tibial tray 102J is positioned within a knee through an incision made to provide access to the knee during surgery, bearing component 104J is inserted atop tibial tray 102J, which has a PCL cutout that is positioned along anatomic home axis M. Alternatively, a PCL cutout may not be present, such as in a posterior stabilized or ultra congruent component in a prosthesis application as noted above.

Bearing component 104J is inserted through the incision to an initial reception position where a posterior end of notch 160J of bearing component 104J receives anterior end 148J of boss 146J of tibial tray 102J. Boss rail recess 180J of notch 160J proceeds to receive boss rail 178J, while a recess of notch 160J receives the anterior, medial, and lateral walls forming edge 176J of boss 146J from which boss rail 178J projects. Such action occurs as bearing component 104J is inserted onto tibial tray 102J along axis M. Medial and lateral sides 150J and 152J of boss 146J are positioned substantially parallel to axis M.

Figure 50:
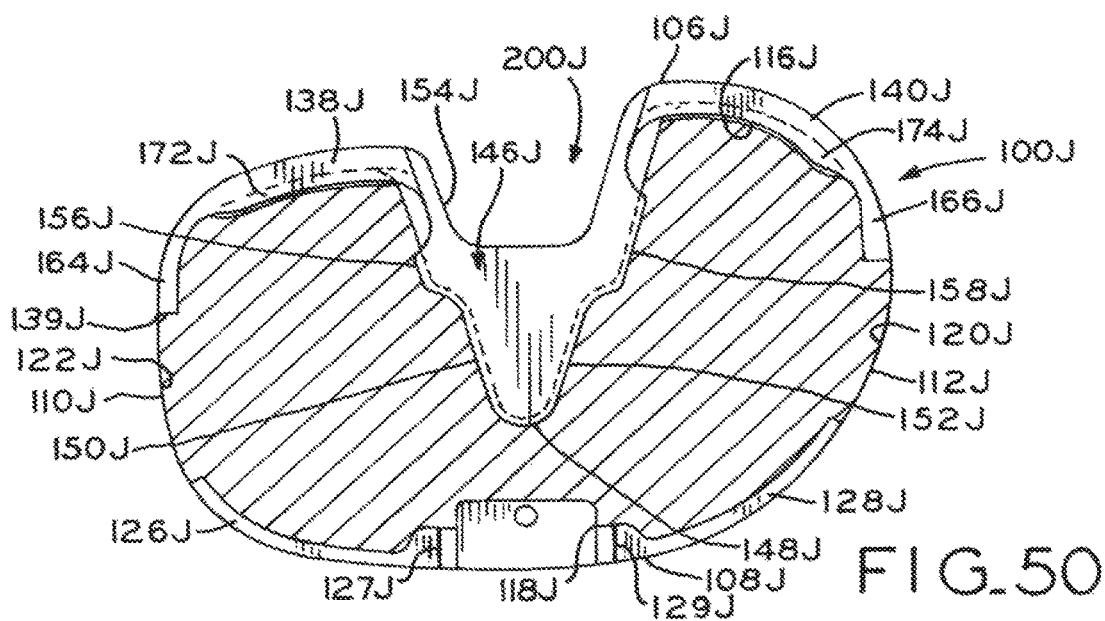
FIG. 50 is a proximal plan, partial, sectional view of the tibial prosthesis of FIG. 49, with the bearing component fully seated on the tibial tray.
Figure 51:
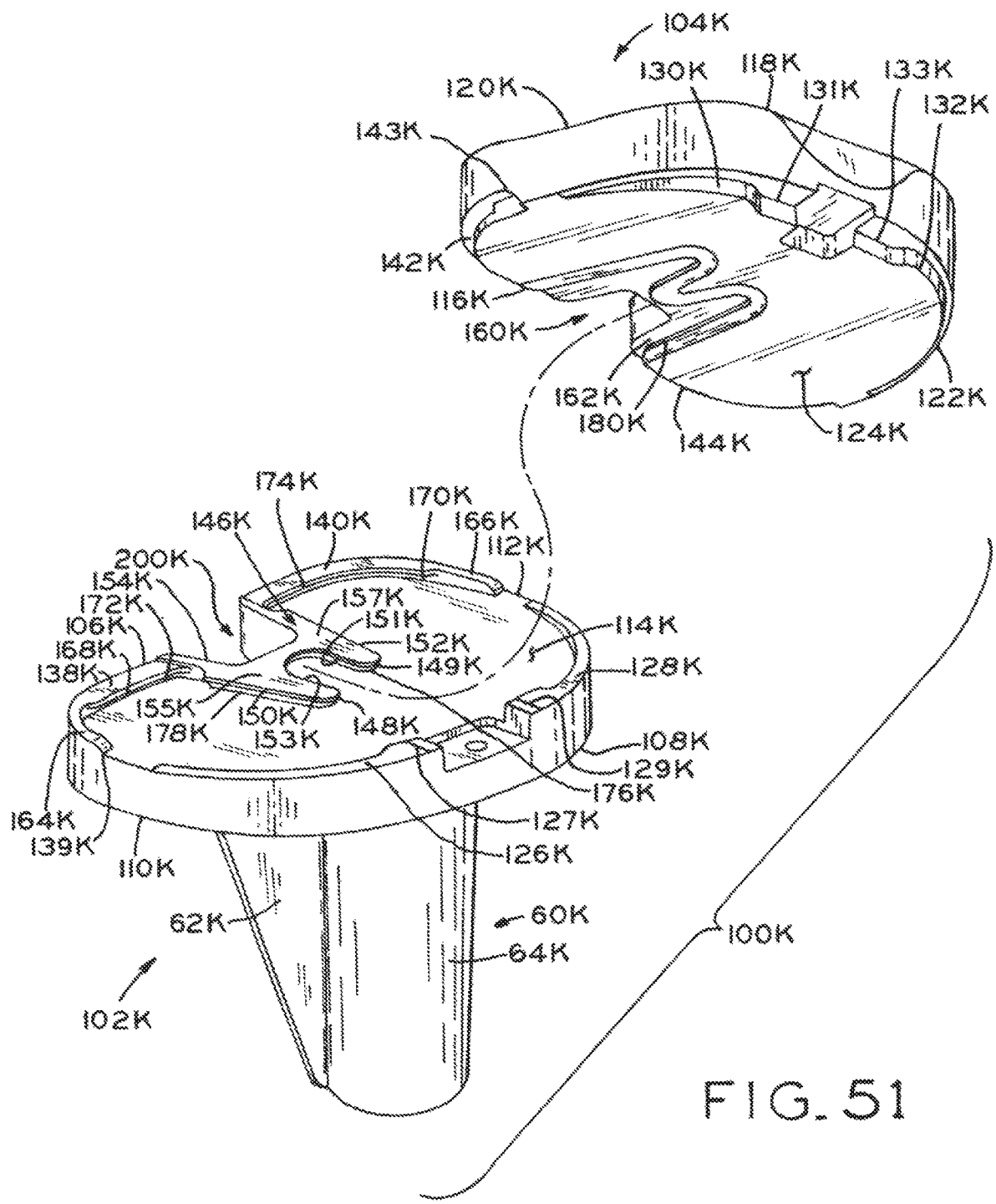
FIG. 51 is an exploded anterior perspective view of a tibial prosthesis made in accordance with an exemplary eleventh embodiment of the present invention, including a bearing component and a tibial tray.
Figure 52:
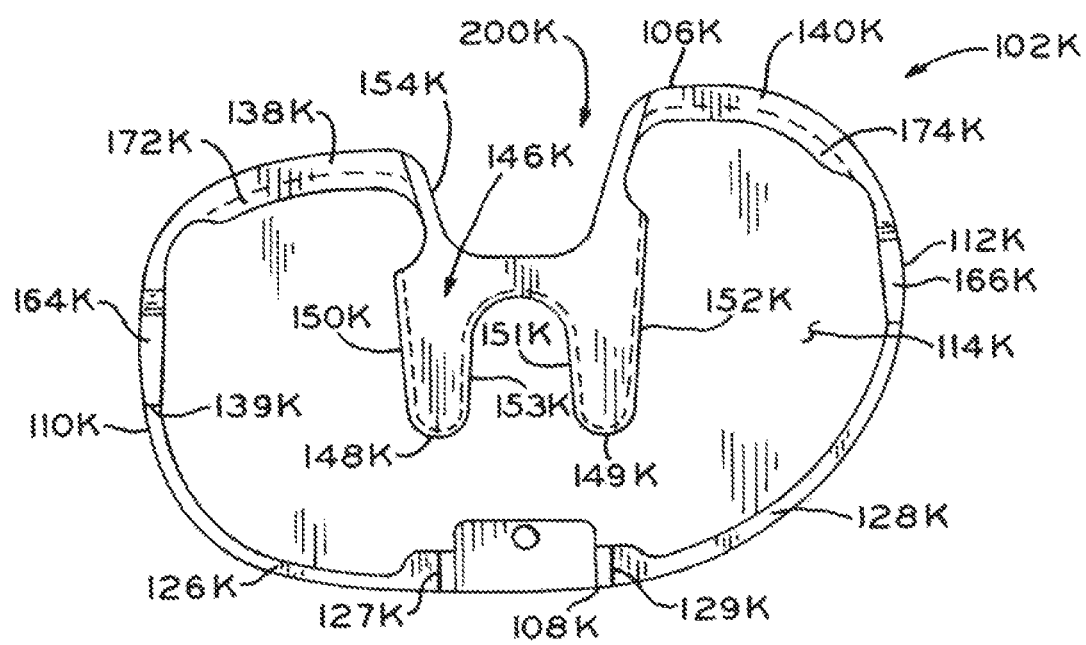
FIG. 52 is a proximal plan view of the tibial tray of the eleventh embodiment.
Figure 53:
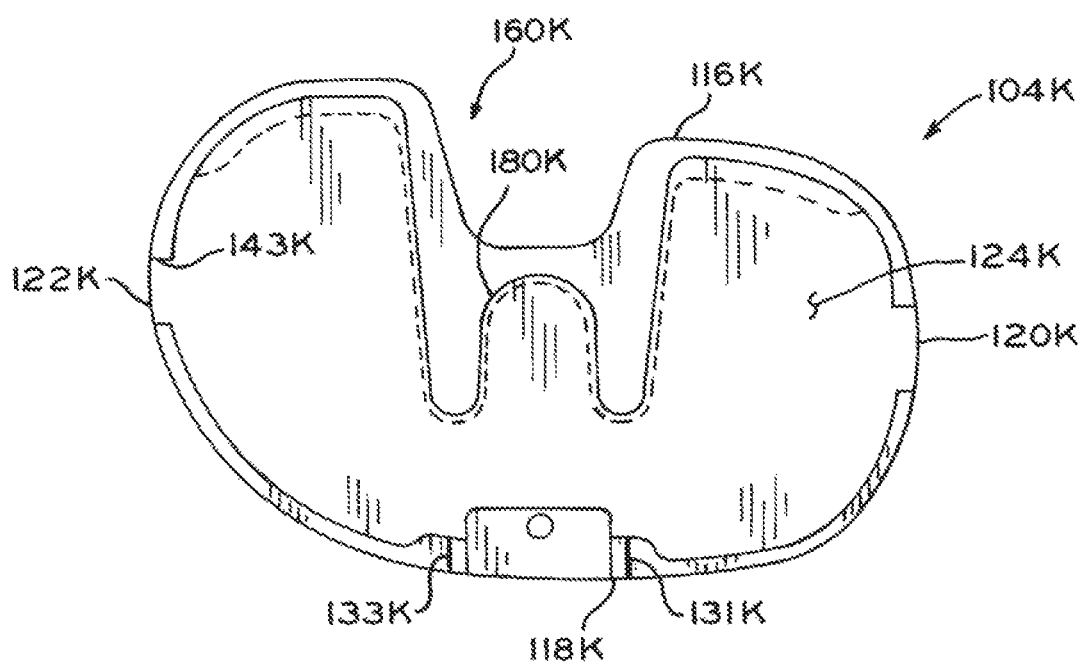
FIG. 53 is a distal plan view of the bearing component of the eleventh embodiment.

Boss rail recess 180J receives boss rail 178J and another recess of notch 160J receives the above-mentioned walls of boss 146J. Further, posterior rail, recesses 142J and 144J experience elastic deformation while receiving undercut posterior rails 138J and 140J, respectively. Further, as bearing component 104J is inserted over tibial tray 102J, bearing component 104J is inserted over anterior rails 126J and 128J of tibial tray 102J to engage in a final snap-fit connection with anterior rails 126J and 128J (FIG. 50). Due the insertion over anterior rails causing a separation between distal surface 124J and support surface 114A, the walls forming the recesses of notch 160J experience elastic deformation if boss rail 178J is undercut.

The deformation described above coupled with frictional forces experienced by the interaction of the described portions of hearing component 104J and tibial tray 102J increases resistance to movement of bearing component 102J along axis M until anterior edge 118J of bearing component 104J passes anterior rails 126J and 128J of tibial tray 102J. Then, bearing component 104J snaps into position in a firm connection created by the operation of anterior edge 118J with an interior side of anterior rails 126J and 128J, and in a firm connection created by the operation of posterior rails 138J and 140J with posterior edge 116J of hearing component 104J.

An additional firm connection occurs between the receipt of boss 146J within notch 160J. Additionally, posterior rails 138J and 140J and boss 146J include projecting perimeter rails 172J and 174J and boss rail 178J, respectively, received into a pair of internal grooves at posterior edge 116K of bearing component 104J and boss rail recess 180J of notch 160J, respectively. Upon a final seating of beating component 104J upon tibial tray 102J, any gaps between the walls forming projecting perimeter rails 172J and 174J and the walls forming the corresponding internal grooves in posterior edge 116J that receive the rails are substantially filled. Similarly, any gaps between the walls forming boss rail 178J and corresponding boss rail recess 180J are substantially filled. The firm connections created by the projecting perimeter rails of posterior rails 138J and 140J and the boss rail of boss 146J assist to prevent lift-off of bearing component 104J from tibial tray 102J in a final seated position (FIG. 50), in which bearing component 104J is locked to tibial tray 102J.

Advantageously, an increase of over 62% of engagement forces occurs between boss 146J and notch 160J to resist rotational micromotion of bearing component 104J and lift-off of bearing component 104j when seated upon and lock to tibial tray 102j, the increase occurring over a design similar to that of the first embodiment but which does not include anterior wedges projecting from an anterior edge of a bearing component.

FIGS. 51-55 illustrate an exemplary eleventh embodiment. Referring to FIGS. 51, 52, 54, and 55, boss 146K of the exemplary eleventh embodiment is similar to boss 146I of the exemplary ninth embodiment. However, similar to the tenth embodiment, boss 146K is aligned along axis M (FIG. 54) rather than canted with respect to anteroposterior axis AP. Further, similar to those described above for the exemplary tenth embodiment, the eleventh embodiment includes a pair of posterior rails 138K and 140K (FIG. 51) that extend to include lateral containment rail 164K and medial containment rail 166K. Further, tibial tray 102K includes anterior rails 126K and 128K which are similar to those described above for the tenth embodiment. Tibial prosthesis 100K also has an asymmetric geometry (FIGS. 52 and 53) similar to that disclosed below for the twelfth amendment, and tibial prosthesis 100K is inserted in a manner similar to that described for the exemplary tenth amendment above such that similar disclosed advantages result upon implantation of bearing component 104K atop tibial tray 102K.

Advantageously, an increase of over 100% of engagement forces occurs between boss 146K and notch 160K to resist rotational micromotion of bearing component 104K and lift-off of bearing component 104K when seated upon and locked to tibial tray 102K, the increase occurring over a design similar to that of the first embodiment but which does not include anterior wedges projecting from an anterior edge of a bearing component.

Turning now to FIGS. 57-62, a twelfth embodiment of a knee prosthesis in accordance with the present disclosure is shown. Knee prosthesis 100L includes tibial tray 102L including a two-pronged boss 146L aligned with home axis M (FIG. 61), similar in structure and orientation to boss 146K of the eleventh embodiment described above. Medial prong 157L extends from an anterior end 149L toward posterior end 154L of tibial tray 102L, and blends smoothly into medial posterior rail 140L. Posterior rail 140L extends around the medial-posterior periphery of support surface 114L, and blends smoothly with medial containment rail 166L. Medial containment rail 166L extends anteriorly to end 139L (FIG. 58), which angles downwardly for a "soft" transition as distinct from the "stepped" transition described above with respect to other embodiments.

Similarly, lateral prong 155L extends posteriorly from anterior end 148L, through lateral posterior rail 138L and anteriorly via lateral containment rail 164L, and to end 139L. A dovetail undercut runs continuously from lateral containment rail 164L to medial containment rail 166L around the entire posterior periphery of support surface 114L and around the periphery of two-pronged boss 146L. Thus, the structures of tibial tray 102L including an undercut extending from lateral containment rail 164L, to lateral posterior rail 138L, to lateral side 150L of lateral prong 155L, around anterior end 148L, along medial side 153L of lateral prong 155L, back up lateral side 151L of medial prong 157L, around lateral anterior end 149L, along medial side 152L of medial prong 157L, to medial posterior rail 140L, and finally to medial containment rail 166L.

When bearing component 104L is mounted to tibial tray 102L, a corresponding undercut formed in notch 160L and around posterior, lateral and medial edges 116L, 120L, 122L forms an interference fit with the undercut in tibial tray 102L at certain locations for optimal securement characteristics. More particularly, all the anteroposteriorly-extending regions of interaction between respective undercuts of tibial tray 102L and tibial bearing component 104L define interference fits.

Figure 61:
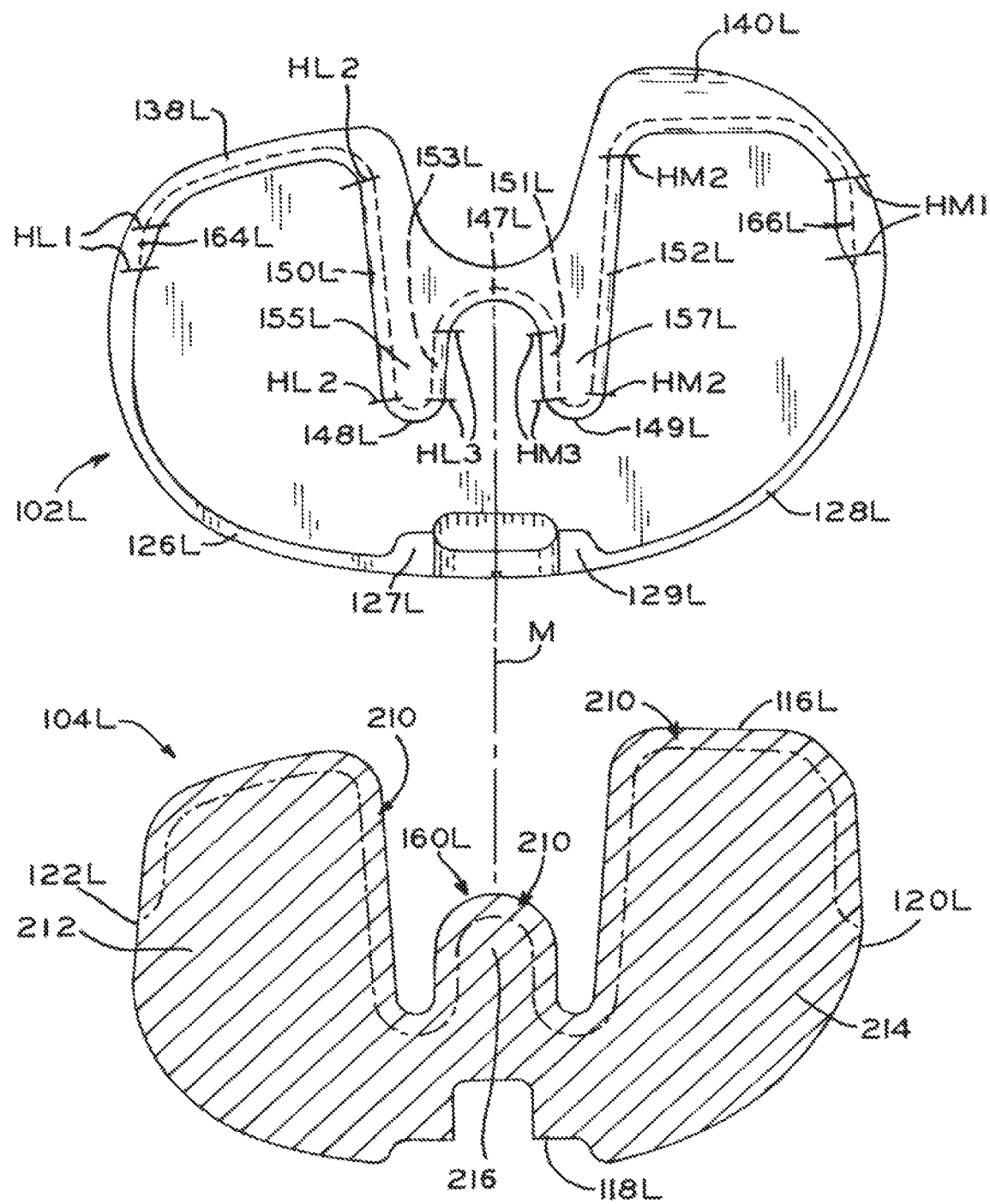
FIG. 61 is a proximal plan, partial sectional view of the tibial prosthesis showing a straight insertion, along an anatomic home axis, of the bearing component onto the tibial tray of the twelfth embodiment.

Turning to FIG. 61, for example, it can be seen that lateral and medial containment rails 164L, 166L define anteroposteriorly extending undercuts, shown bounded at anterior and posterior ends by respective pairs of lateral and medial hash marks HL1, HM1. Similarly, lateral-facing and medial-facing sides 150L, 152L of lateral and medial prongs 155L, 157L, respectively, define anteroposterior extents illustrated between pairs of lateral and medial hash marks HL2, HM2, respectively. Finally, the "inside" faces of lateral and medial prongs 155L, 157L, i.e., medial-facing and lateral-facing sides 153L, 151L respectively, define anteroposterior extents between pairs of hash marks HL3, HM3, respectively.

Figure 62:
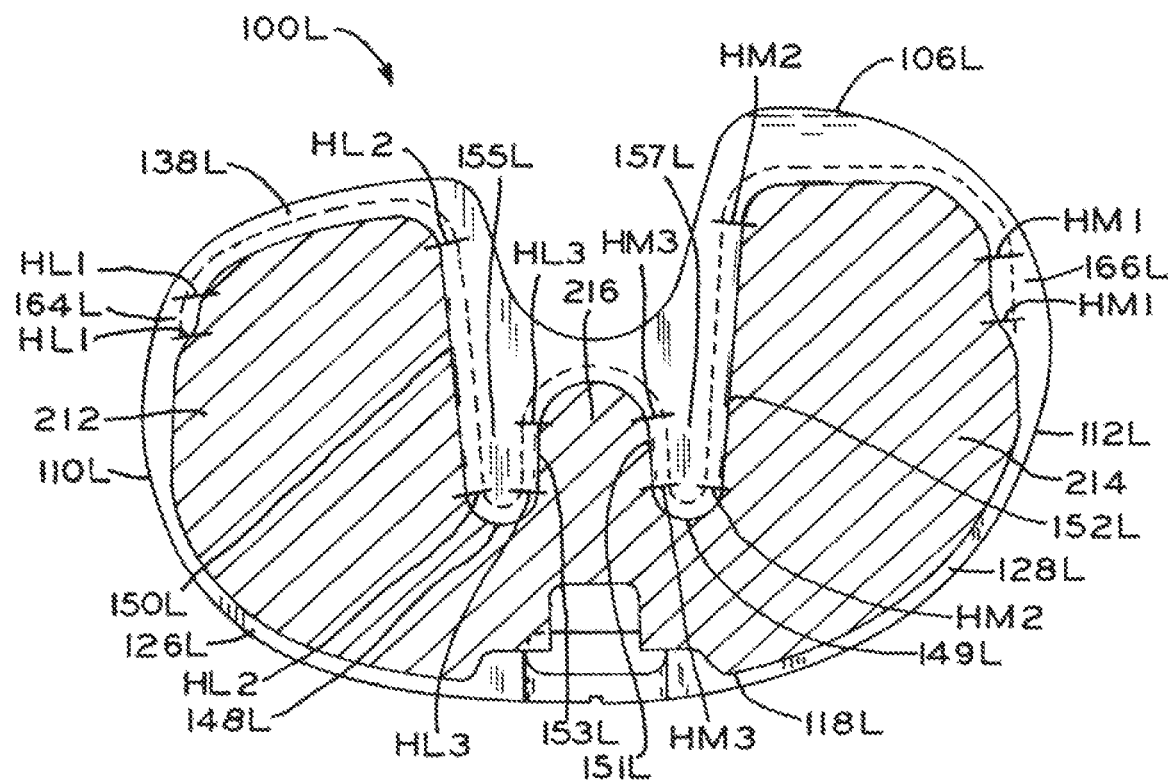
FIG. 62 is a proximal plan, partial sectional view of the tibial prosthesis of FIG. 61, with the bearing component fully seated on the tibial tray.

Referring now to FIG. 62, a cross-section of tibial bearing component 104L is shown assembled to tibial tray 102L. Tibial bearing component includes a dovetail undercut 210 (FIG. 61) which mates with the corresponding dovetail undercut formed in tibial tray 102L as described above. When so mated, lateral compartment 212 of tibial baseplate is slightly compressed in a medial-to-lateral direction between lateral-facing side 150L of lateral prong 155L and lateral containment rail 164L, thereby defining a first interference fit. Similarly, medial compartment 214 if tibial bearing component is slightly compressed between medial-facing side 152L of medial prong 157L and medial containment rail 166L, thereby defining a second interference fit. Finally, central protrusion 216 of tibial bearing component, which cooperates with lateral and medial compartments 212, 214 to define two-pronged notch 160L, is compressingly received between sides 153L, 151L of lateral and medial prongs 155L, 157L to define a third interference fit.

Advantageously, the interference fits described above introduce some elastic deformation into tibial bearing component 104L, which is made of a softer, more resilient material (e.g., polyethylene) as compared to the harder, more rigid material of tibial tray 102L (e.g., cobalt-chrome-molybdenum or titanium). This introduces some tension within the material of tibial bearing component 104L, which contributes to the rotational stability of bearing component 104L with respect to tibial tray 102L. More particularly, micromotion of tibial bearing component 104L is minimized by these interference fits.

At the same time, clearance fits are provided at the medial-lateral interactions between undercut 212 of bearing component 104L and the corresponding structures of tibial tray 102L (e.g., posterior rails 138L, 140L, anterior ends 148L, 149L, and arcuate space 147L between interior sides 151L, 153L). This eases the snap-fit of bearing 104L into place upon tibial tray 102L, as described above with respect to other embodiments, thereby keeping insertion forces low enough to prevent and permanent deformation or damage to tibial bearing component 104L upon assembly.

Figure 59:
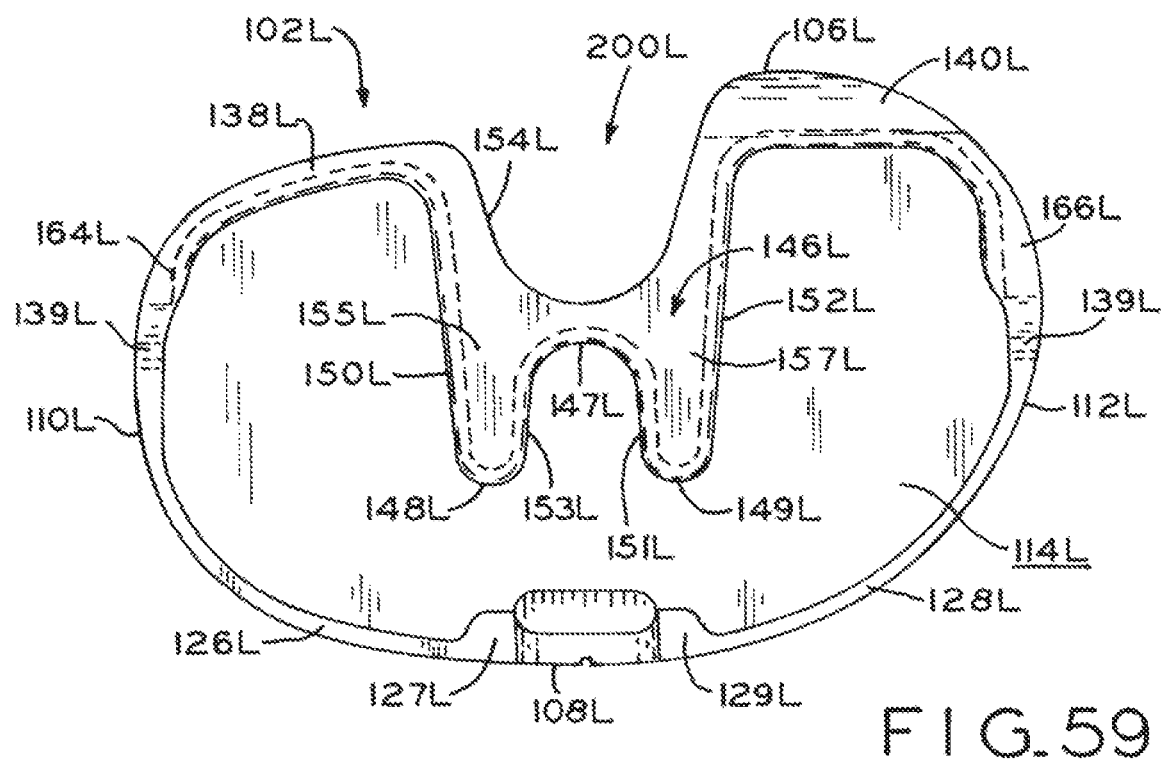
FIG. 59 is a proximal plan view of the tibial tray of the twelfth embodiment.
Figure 60:
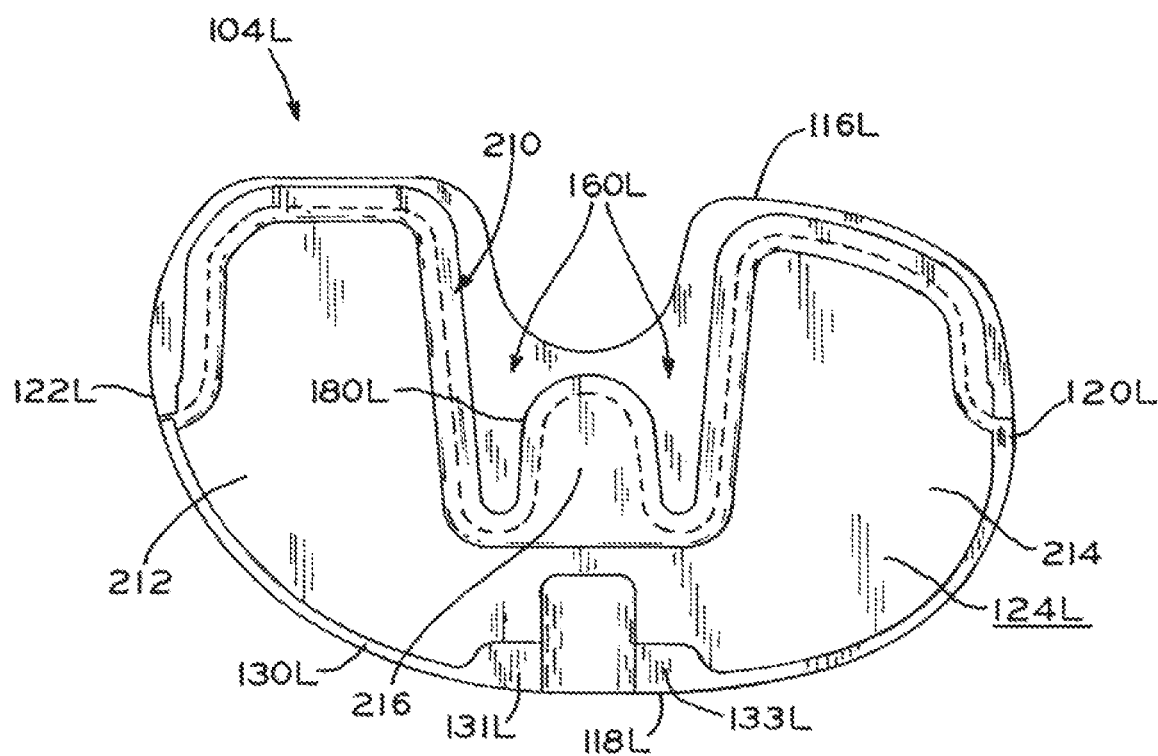
FIG. 60 is a distal plan view of the bearing component of the twelfth embodiment.

Assembly of tibial bearing component 104L to tibial tray 102L may also be facilitated by providing undercut profiles which converge and/or diverge in certain respects. Turning to FIG. 59, for example, it can be seen that sides 150L, 152L (which face outwardly, away from one another) converge with respect to one another toward anterior ends 148L, 149L. On the other hand, sides 151L, 153L (which face inwardly, toward one another) diverge toward anterior ends 148L, 149L. Similarly, medial containment rail 166L diverges anteriorly with respect to medial side 152L of medial prong 157L (which face inwardly), and lateral containment rail 164L diverges anteriorly with respect to lateral side 150L of lateral prong 155L (also inwardly facing).

Upon assembly, the anterior convergence of outwardly facing sides and divergence of inwardly facing sides presents a profile which "opens" to the advancing notch 160L of bearing component 104L. Thus, undercut 210 of bearing component 104L, does not firmly engage the corresponding anteroposterior undercuts of tibial tray 102L throughout the anterior-to-posterior advancement on assembly, as would happen if such undercuts were parallel. Rather, full and firm engagement of such undercuts only occurs as tibial bearing component 104L advances into its final engaged and locked position with respect to tibial tray 102L. Advantageously, this "short-stroke" engagement allows distal surface 124L to be easily passed over support surface 114L, and facilitates the initial engagement of the interference-fit anteroposterior undercuts.

Tibial tray 102L further includes a pair of anterior rails 126L and 128L having thicker portions 127J and 129J (relative to the rest of the rail) at anterior most ends, similar to certain other embodiments described in detail above (e.g., the tenth embodiment). Thicker portions 127J and 129J interrupt what would otherwise be a continuous arcuate profile defined by anterior rails 126L, 128L. When tibial bearing component 104L is assembled to tibial tray 104L in the manner discussed herein, thicker portions 127J and 129J are received into corresponding thicker anterior rail recessed portions 131L and 133L, respectively, of anterior rail recesses 130L, 132L. When so received, thicker portions 127J and 129J interfit with recessed portion 131L, 133L to present a barrier to rotation along the otherwise smooth arcuate profiles of anterior rails 126L, 128L. Advantageously, this barrier to rotation further inhibits rotational micromotion of tibial bearing component 104L with respect to tibial tray 102L.

Any of the embodiments described herein may include an asymmetric tibial tray and/or asymmetric tibial bearing component. For example, As best seen in FIG. 57, a posteriorlateral edge of tibial tray 102I has a relatively shorter distance DL from an anterior-lateral edge of tibial tray 102I, as compared to longer distance DM from a posterior-medial edge to an anterior-medial edge. This disparity of medial and lateral anteroposterior extents results in an asymmetric periphery of tibial tray 102I. A corresponding asymmetry of bearing component 104I is shown in FIG. 47. Such asymmetry is described in greater detail in U.S. patent application Ser. Nos. 13/189,336, 13/189,338 and 13/189,339, incorporated by reference above.

The above-described exemplary embodiments are generally directed to a "primary" prosthesis, i.e., a prosthesis which is designed to be implanted, in a natural knee which retained natural articular surfaces prior to the implantation. However, it is also contemplated that prosthetic knee components made in accordance with the present disclosure may also be used in a revision procedure, in which one or more previously-implanted knee prosthesis components are removed and replaced. For example, the exemplary tibial trays described above are amenable to reuse in a revision procedure, such that the tibial tray is left in its originally-implanted position on the tibia and only the tibial bearing component is replaced. Advantageously, leaving the tibial tray in place allows the tibial bearing component to be replaced without further resection of the tibia, which might otherwise be required where the tibial tray is removed.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A tibial prosthesis, comprising:
   a tibial tray comprising:
   a posterior edge;
   an anterior edge;
   a support surface; and
   a peripheral wall disposed above the support surface, the peripheral wall including a two-pronged boss, wherein the two-pronged boss includes a medial prong extending from a posterior portion of the peripheral wall along the posterior edge toward the anterior edge and having a medially facing side and a laterally facing side, and a lateral prong extending from a posterior portion of the peripheral wall along the posterior edge toward the anterior edge having a medially facing side and a laterally facing side, wherein the peripheral wall defines a tray undercut; and
   a bearing component comprising:
   an articulating surface;
   a distal surface opposing the articulating surface and configured to interface with the support surface; and
   a peripheral wall extending between the articulating surface and the distal surface, wherein one or more portions of at least one of the peripheral wall of the bearing component and the distal surface form a notch that defines a bearing undercut, wherein the bearing undercut is configured to engage with the tray undercut to retain the bearing component with the tibial tray.

2. The tibial prosthesis of claim 1, wherein the tray undercut extends generally anteroposteriorly along four sections of the two-pronged boss and the four sections engage with corresponding sections of the bearing undercut to define three interference fits between the bearing component and the tibial tray.

3. The tibial prosthesis of claim 2, wherein the bearing component is configured such that during the three interference fits a lateral compartment is compressed in a medial-to-lateral direction between the laterally facing side of the lateral prong and a lateral containment rail, a medial compartment is compressed in a lateral-to medial direction between the medially facing side of the medial prong and a medial containment rail and a two-pronged notch of the bearing component is compressed by reception between the laterally facing side of the medial prong and the medially facing side of the lateral prong.

4. The tibial prosthesis of claim 2, wherein the four sections connect with two additional sections to form six anteroposteriorly extending sections defined by a medial containment rail, a lateral containment rail, the laterally facing side of the lateral prong, the medially facing side of the lateral prong, the laterally facing side of the medial prong and the medially facing side of the medial prong.

5. The tibial prosthesis of claim 4, wherein the medial containment rail terminates more anteriorly than the lateral containment rail.

6. The tibial prosthesis of claim 1, wherein the tray undercut extends generally medial-laterally for at least three sections that engage with corresponding sections of the bearing undercut to define clearance fits between the bearing component and the tibial tray, and wherein the at least three sections are defined by one or more of a recess formed between at least a portion of the laterally facing side of the medial prong and at least a portion of the medially facing side of the lateral prong, a medial posterior rail, a lateral posterior rail, a medial anterior rail and a lateral anterior rail.

7. The tibial prosthesis of claim 1, wherein the tray undercut and the bearing undercut are shaped as a wedge.

8. The tibial prosthesis of claim 1, wherein the tray undercut extends continuously an entire length of a periphery of the two-pronged boss.

9. The tibial prosthesis of claim 1, wherein a lateral tray edge and the laterally facing side of the lateral prong anteriorly diverge, a medial tray edge and the medially facing side of the medial prong anteriorly diverge, the laterally facing side of the medial prong and the medially facing side of the lateral prong anteriorly diverge and the medially facing side of the medial prong and the laterally facing side of the lateral prong anteriorly converge.

10. The tibial prosthesis of claim 1, wherein the tray undercut extends along a medial tray edge, a posterior tray edge, a lateral tray edge, the medially facing side and the laterally facing side of the medial prong, and the medially facing side and the laterally facing side of the lateral prong.

11. The tibial prosthesis of claim 1, wherein the two-pronged boss defines a recess formed between at least a portion of the laterally facing side of the medial prong and at least a portion of the medially facing side of the lateral prong.

12. A tibial prosthesis, comprising:
a tibial tray comprising:
a posterior edge;
an anterior edge;
a support surface; and
a peripheral wall disposed above the support surface, the peripheral wall including a two-pronged boss, wherein the two-pronged boss includes a medial prong extending from posterior portion of the peripheral wall along the posterior edge toward the anterior edge and having a medially facing side and a laterally facing side, and a lateral prong extending from a posterior portion the peripheral wall along the posterior edge toward the anterior edge having a medially facing side and a laterally facing side, wherein the peripheral wall defines a tray undercut that is shaped as wedge; and
a bearing component comprising:
an articulating surface;
a distal surface opposing the articulating surface and configured to interface with the support surface; and
a peripheral wall extending between the articulating surface and the distal surface, wherein one or more portions of at least one of the peripheral wall of the bearing component and the distal surface form a notch that defines a bearing undercut, wherein the bearing undercut is configured to engage with the tray undercut to retain the bearing component with the tibial tray.

13. The tibial prosthesis of claim 12, wherein the tray undercut that extends generally anteroposteriorly along four sections of the two-pronged boss and medial-laterally along one section of the two-pronged boss, wherein the four sections engage with corresponding sections of the bearing undercut to define three interference fits between the bearing component and the tibial tray.

14. The tibial prosthesis of claim 13, wherein the bearing component is configured such that during the three interference fits a lateral compartment is compressed in a medial-to-lateral direction between the laterally facing side of the lateral prong and a lateral containment rail, a medial compartment is compressed in a lateral-to-medial direction between the medially facing side of the medial prong and a medial containment rail and a two-pronged notch of the bearing component is compressed by reception between the laterally facing side of the medial prong and the medially facing side of the lateral prong.

15. The tibial prosthesis of claim 12, wherein the tray undercut extends generally medial-laterally for at least three sections that engage with corresponding sections of the bearing undercut to define clearance fits between the bearing component and the tibial tray, and wherein the at least three sections are defined by one or more of a recess formed between at least a portion of the laterally facing side of the medial prong and at least a portion of the medially facing side of the lateral prong, a medial posterior rail, a lateral posterior rail, a medial anterior rail and a lateral anterior rail.

16. The tibial prosthesis of claim 12, wherein a lateral tray edge and the laterally facing side of the lateral prong anteriorly diverge, a medial tray edge and the medially facing side of the medial prong anteriorly diverge, the laterally facing side of the medial prong and the medially facing side of the lateral prong anteriorly diverge and the medially facing side of the medial prong and the laterally facing side of the lateral prong anteriorly converge.

17. A tibial prosthesis, comprising:
a tibial tray comprising:
a support surface; and
a peripheral wall disposed above the support surface, the peripheral wall including a two-pronged boss, wherein the two-pronged boss includes a medial prong having a medially facing side and a laterally facing side, and a lateral prong having a medially facing side and a laterally facing side; and
a bearing component comprising:
an articulating surface;
a distal surface opposing the articulating surface and configured to interface with the support surface; and
a peripheral wall extending between the articulating surface and the distal surface, wherein one or more portions of at least one of the peripheral wall of the bearing component and the distal surface form a notch that defines a bearing undercut, wherein the bearing undercut is configured to engage with the peripheral wall to retain the bearing component with the tibial tray; and
wherein the peripheral wall engages with the bearing undercut to define three interference fits, and wherein the bearing component is configured such that during the three interference fits a lateral compartment is compressed in a medial-to-lateral direction, a medial compartment is compressed in a lateral-to-medial direction and a two-pronged notch of the bearing component is compressed.

18. The tibial prosthesis of claim 17, wherein the lateral compartment is compressed between the laterally facing side of the lateral prong and a lateral containment rail, the medial compartment is compressed between the medially facing side of the medial prong and a medial containment rail and the two-pronged notch of the bearing component is compressed by reception between the laterally facing side of the medial prong and the medially facing side of the lateral prong.

19. The tibial prosthesis of claim 17, wherein the peripheral wall and the bearing undercut are shaped as a wedge.

20. The tibial prosthesis of claim 17, wherein the peripheral wall extends generally medial-laterally for at least three sections that engage with corresponding sections of the bearing undercut to define clearance fits between the bearing component and the tibial tray, and wherein the at least three sections are defined by one or more of a recess formed between at least a portion of the laterally facing side of the medial prong and at least a portion of the medially facing side of the lateral prong, a medial posterior rail, a lateral posterior rail, a medial anterior rail and a lateral anterior rail.

* * * * *

UNITED STATES PATENT AND TRADEMARK OFFICE
CERTIFICATE OF CORRECTION

PATENT NO. : 10,543,099 B2
APPLICATION NO. : 15/703678
DATED : January 28, 2020
INVENTOR(S) : Sanford et al.

Page 1 of 1

It is certified that error appears in the above-identified patent and that said Letters Patent is hereby corrected as shown below:

On the Title Page

On page 6, in Column 1, item (56), under "Other Publications", Line 34, delete "May" and insert --Mar.-- therefor On page 7, in Column 1, item (56), under "Other Publications", Line 2, delete "Feb. 2," and insert --Dec. 2,-- therefor On page 7, in Column 1, item (56), under "Other Publications", Line 41, delete "Feb. 12," and insert --Dec. 12,-- therefor On page 8, in Column 1, item (56), under "Other Publications", Line 20, delete "Feb. 24," and insert --Nov. 24,-- therefor In the Claims In Column 25, Line 39, in Claim 12, after "as", insert --a--

Signed and Sealed this
First Day of September, 2020

Andrei Iancu
*Director of the United States Patent and Trademark Office*